United States Patent
Allard et al.

(10) Patent No.: US 9,066,816 B2
(45) Date of Patent: Jun. 30, 2015

(54) SPINAL NUCLEUS REPLACEMENT IMPLANTS

(75) Inventors: Randall Allard, Issaquah, WA (US); Robert S. Biscup, Fort Lauderdale, FL (US); Thomas Carls, Memphis, TN (US); Jason Eckhardt, Memphis, TN (US); Tom Francis, Memphis, TN (US); Clayton G. Leroux, Westlake, OH (US); Robert B. Rice, Warsaw, IN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1563 days.

(21) Appl. No.: 12/356,713

(22) Filed: Jan. 21, 2009

(65) Prior Publication Data

US 2010/0185287 A1 Jul. 22, 2010

(51) Int. Cl.
*A61F 2/44* (2006.01)
*A61F 2/46* (2006.01)
*A61B 19/00* (2006.01)
(Continued)

(52) U.S. Cl.
CPC ............. *A61F 2/4611* (2013.01); *A61B 19/201* (2013.01); *A61B 2017/00261* (2013.01); *A61F 2/30744* (2013.01); *A61F 2/442* (2013.01); *A61F 2002/30014* (2013.01); *A61F 2002/3008* (2013.01); *A61F 2002/30131* (2013.01); *A61F 2002/30242* (2013.01); *A61F 2002/30383* (2013.01); *A61F 2002/3052* (2013.01); *A61F 2002/30561* (2013.01); *A61F 2002/30563* (2013.01); *A61F 2002/30579* (2013.01); *A61F 2002/30604* (2013.01); *A61F 2002/30611* (2013.01); *A61F 2002/30673* (2013.01); *A61F 2002/30733* (2013.01); *A61F 2002/30975* (2013.01); *A61F 2002/444* (2013.01); *A61F 2002/4495* (2013.01); *A61F 2002/4627* (2013.01); *A61F 2002/4629* (2013.01); *A61F 2002/4677* (2013.01); *A61F 2220/0025* (2013.01); *A61F 2230/0013* (2013.01); *A61F 2230/0071* (2013.01); *A61F 2250/0018* (2013.01); *A61F 2250/0063* (2013.01); *A61F 2250/0098* (2013.01);
(Continued)

(58) Field of Classification Search
USPC ........................................................ 623/17.11
See application file for complete search history.

(56) References Cited

U.S. PATENT DOCUMENTS 4,777,947 A 10/1988 Zwick
4,936,848 A 6/1990 Bagby
(Continued)

FOREIGN PATENT DOCUMENTS

CA 2441384 A1 11/2002
DE 2804936 A1 8/1979
(Continued)

OTHER PUBLICATIONS

Dept. of Surgery, Arthroplasty with Intercorporal Endoprothesis in Herniated Disc and in Painful Disc, from , Uddevalla, Sweden, Suppl. 357, 1966.
(Continued)

*Primary Examiner* — Thomas J Sweet
*Assistant Examiner* — Matthew Schall

(57) ABSTRACT

A multi-piece intervertebral disc augmentation implant that may be assembled within the annulus fibrosus is disclosed. The implant may be guided into a precise location through a relatively small opening in the annulus fibrosus with the aid of an elongated guide.

18 Claims, 32 Drawing Sheets

(51) Int. Cl.
  *A61B 17/00* (2006.01)
  *A61F 2/30* (2006.01)
(52) U.S. Cl.
  CPC .......... *A61F 2310/00017* (2013.01); *A61F 2310/00023* (2013.01); *A61F 2310/00029* (2013.01)

(56) References Cited

U.S. PATENT DOCUMENTS

| | | | |
|---|---|---|---|
| 5,059,193 | A | 10/1991 | Kuslich |
| 5,250,061 | A | 10/1993 | Michelson |
| 5,458,611 | A | 10/1995 | Resnick et al. |
| 5,472,010 | A | 12/1995 | Gonzalez |
| 5,645,596 | A | 7/1997 | Kim et al. |
| 5,743,918 | A | 4/1998 | Calandruccio et al. |
| 5,888,226 | A | 3/1999 | Rogozinski |
| 6,102,950 | A | 8/2000 | Vaccaro |
| 6,120,509 | A | 9/2000 | Wheeler |
| 6,436,101 | B1 | 8/2002 | Hamada |
| 6,478,822 | B1 | 11/2002 | Leroux et al. |
| 6,517,580 | B1 | 2/2003 | Ramadan et al. |
| 6,638,310 | B2 | 10/2003 | Lin et al. |
| 6,648,917 | B2 | 11/2003 | Gerbec et al. |
| 6,652,534 | B2 | 11/2003 | Zucherman et al. |
| 6,726,720 | B2 | 4/2004 | Ross et al. |
| 6,733,531 | B1 | 5/2004 | Trieu |
| 6,733,534 | B2 | 5/2004 | Sherman |
| 6,749,608 | B2 | 6/2004 | Garito et al. |
| 6,794,960 | B2 | 9/2004 | Chiu et al. |
| 7,001,433 | B2 | 2/2006 | Songer et al. |
| 7,267,692 | B2 | 9/2007 | Fortin et al. |
| 2002/0120283 | A1 | 8/2002 | Holmes |
| 2002/0156528 | A1 | 10/2002 | Gau |
| 2003/0023308 | A1 | 1/2003 | Leroux et al. |
| 2003/0204261 | A1 | 10/2003 | Eisermann et al. |
| 2003/0220691 | A1 | 11/2003 | Songer et al. |
| 2004/0024461 | A1 | 2/2004 | Ferree |
| 2004/0030391 | A1 | 2/2004 | Ferree |
| 2004/0093082 | A1 | 5/2004 | Ferree |
| 2004/0176773 | A1 | 9/2004 | Zubok et al. |
| 2004/0186576 | A1 | 9/2004 | Biscup et al. |
| 2005/0015151 | A1 | 1/2005 | Fortin et al. |
| 2005/0055097 | A1 | 3/2005 | Grunberg |
| 2005/0149188 | A1 | 7/2005 | Cook et al. |
| 2006/0095132 | A1 | 5/2006 | Kirschman |
| 2006/0106462 | A1 | 5/2006 | Tsou |
| 2006/0224240 | A1 | 10/2006 | Allard et al. |
| 2008/0086127 | A1 | 4/2008 | Patterson et al. |
| 2008/0122017 | A1 | 5/2008 | Parks |

FOREIGN PATENT DOCUMENTS

| | | |
|---|---|---|
| EP | 1354572 A2 | 10/2003 |
| WO | WO9531948 | 11/1995 |
| WO | WO02087480 A1 | 11/2002 |
| WO | WO03024368 A1 | 3/2003 |
| WO | WO03099172 A1 | 12/2003 |
| WO | WO2005081884 A2 | 9/2005 |
| WO | WO2005086067 A1 | 9/2005 |

OTHER PUBLICATIONS

Alvin H. McKenzie, MD, Fernstrom Intervertebral Disc Arthroplasty: A Long-Term Evaluation, Orthopedics International Ed., Jul./Aug. 1995, vol. 3, No. 4.

Hjalmar Reitz and Mauritius J. Joubert, Intractable Headache and Cervico-Brachialgia Treated by Complete Replacement of Cervical Intervertebral Discs With a Metal Prosthesis", Reprinted S.A. Medical Journal", vol. 38, Nov. 7, 1964, pp. 881-884.

Medtronoic Sofamor Danek, USA, Inc., Satellite Interdiscal Stabilization Sphere Surgical Technique, 2004, 5 pages.

Lippincott Williams & Wilkins, Inc., Intervertebral Disc Prostheses, Guyer and Ohnmeiss, Spine vol. 28, No. 15S, Copyright 2003, pp. S15-S23.

Casey et al. "Heterostructure Lasers", Academic Press, p. 21-79, 1978.

Cheng et al. "Vertical-Cavity Surface-Emitting Lasers: Technology and Applications", Gordon and Breach Science Publishers, 10: 1-31,2000.

Dietrich "Reflection Loss of Laser Mode from Tilted and Mirror", Journal of Lightwave Technology, 7(2): 336-346, 1989.

Jaskorzyrtska et al. "Modal Reflectivity of Uptapered, Tilted-Facet, and antireflection-Coated Diode-Laser Amplifiers", Journal of Optical Soc. Am.,8(2): 484-493, 1991.

Karachinsky et al. "High Power GaAs/AlGaAs Lasers (X ~ 850 nm) With ultranarrow Vertical Beam Divergence", Applied Physics Letters, 89(231114): 1-3, 2006.

Kettler etal. Single Transverse Mode 850 nm GaAs/AlGaAs Lasers With Narrow Beam Divergence, Electronics Letters, 42(20), 2006.

Ledentsov "Nanostructures How Nature Does It", http://edu.ioffe.ru/lectures/leden/index en.html, 2000.

Ledentsov et at. "Novel Approaches to Semiconductor Lasers", Proceedings of SPIE, 4905: 222-233,2002.

Ledentsov et al. "Novel Concepts for Injection Lasers", Optical Engineers, 41(12): 3193-3203,2002.

Maximov et al. "High Power 645 nm Lasers With Narrow Vertical Beam Divergence (8° FWHM)", Nanostructures: Physics and Technology, p. 89-90, 2005.

Maximov et at. "High Power GaInP/AlGaInP Visible Lasers (X=646 nm) With Narrow Circular Shaped Far-Field Pattern", Electronics Letters, 41(13): 1-2,2005.

Maximov et al. "High-Performance 640-nm-Range GaInP-ALGaInP Lasers Based on the Longitudinal Photonic Bandgap Crystal With Narrow Vertical Beam Divergence", IEEE Journal of Quantum Electronics, 41(11): 1341-1348,2005.

Maximov et al. "Longitudinal Photonic Bandgap Crystal Laser Diodes With Ultra-Narrow Vertical Beam Divergence", Proc. of SPIE, 6115: 1-13,2006.

Maximov et al. "Low Divergence Edge-Emitting Laser With Asymmetric Waveguide Based on One-Dimensional Photonic Crystal", Phys. Stat. Sol., 2(2): 919-922,2005.

Maximov et al. "Narrow Vertical Beam Divergence Laser Diode Based on Longitudinal Photonic Band Crystal Waveguide", Electronics Letters, 39(24): 2.P, 2003.

Meade et al. "Accurate Theoretical Analysis of Photonic Band-Gap Materials", Physical Review, 48(11): 8434-8437, 1993.

Novikov et al. "Single Mode CW Operation of 658 NM AlGaInP Lasers Based on Longitudinal Photonic Band Gap Crystal", Applied Physics Letters, 88: 1-3,2006.

Shchukin et al. "High Brilliance Photonic Band Crystal lasers", Proc. ofSPIE, 6350: 1-15,2006.

Shchukin et al. "Nanoface ting and Alloy Decomposition: From Basic Studies to Advanced Photonic Devices", Microelectronics Journal, 37: 1451-1460, 2006.

"A Compact Optical Isolator With a Piano-Convex YIG Lens for Laser-to-Fiber Coupling", Journal of Linhtwave Technology, 7(2);340-346, Feb. 1989.

Office Action Dated Dec. 2, 2009 From the Israel Patent Office Re.: Application No. 183250 and Its Translation Into English.

Response Dated Jan. 13, 2010 to Office Action of Sep. 18, 2009 From the State Intellectual Property Office Re.: Application No. 200580046301.7.

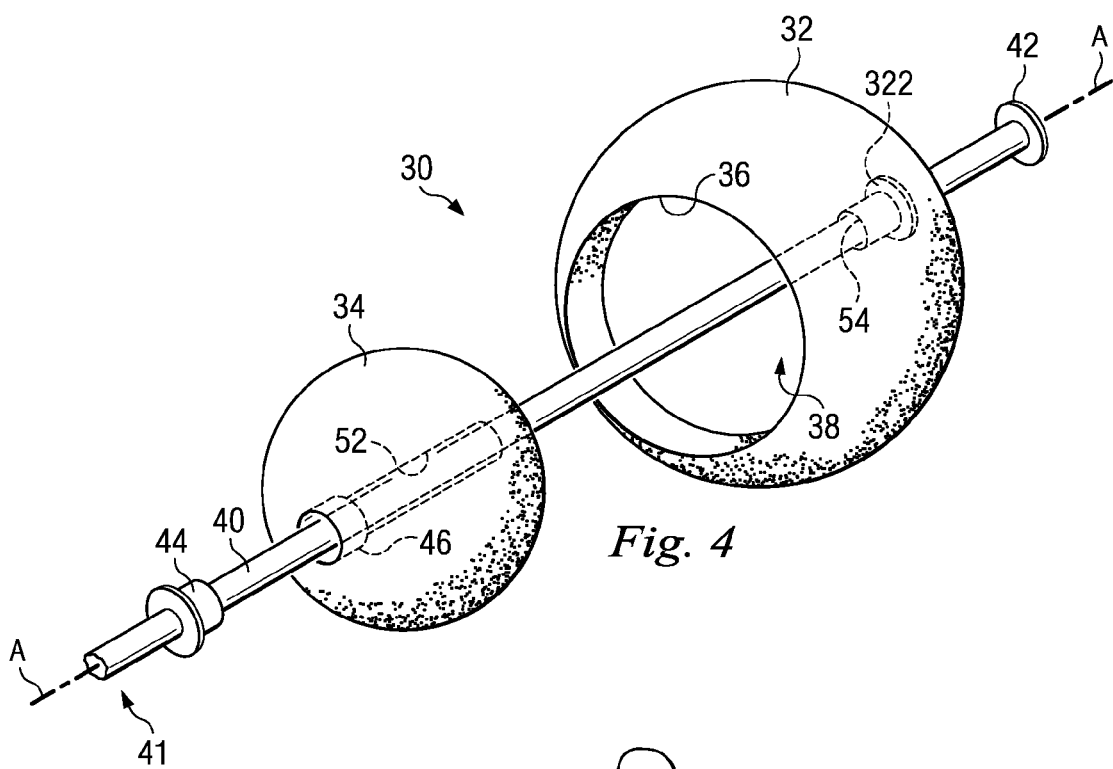
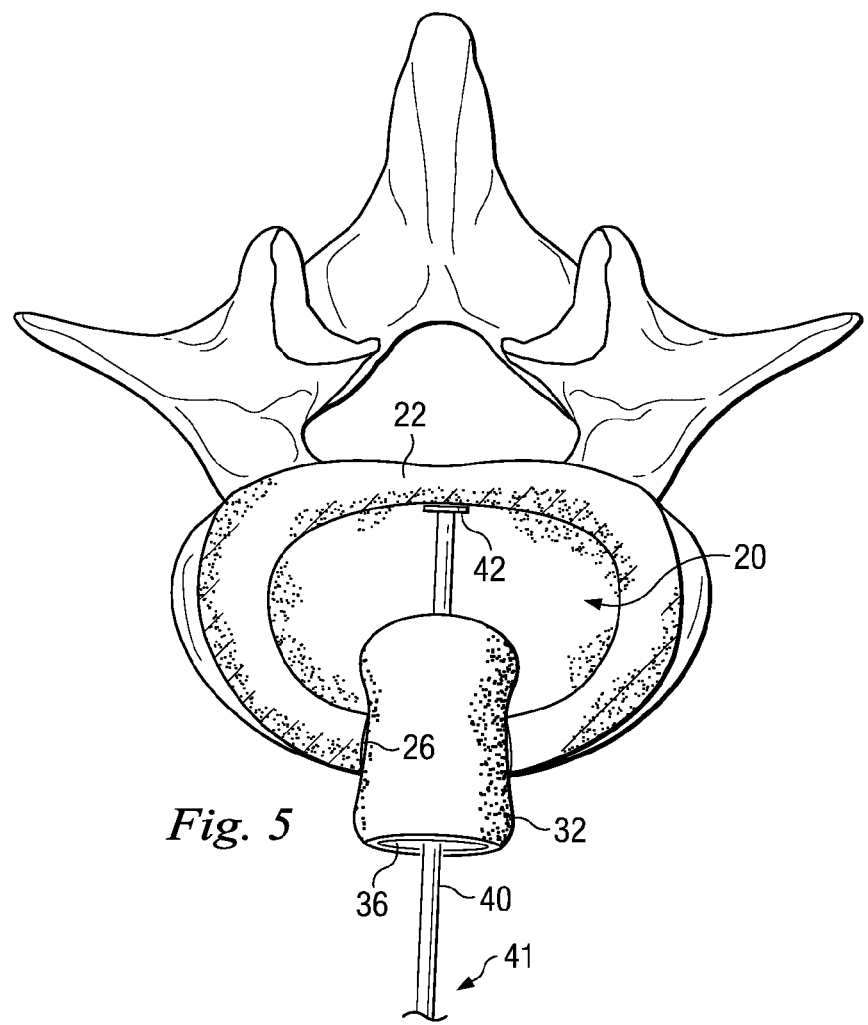

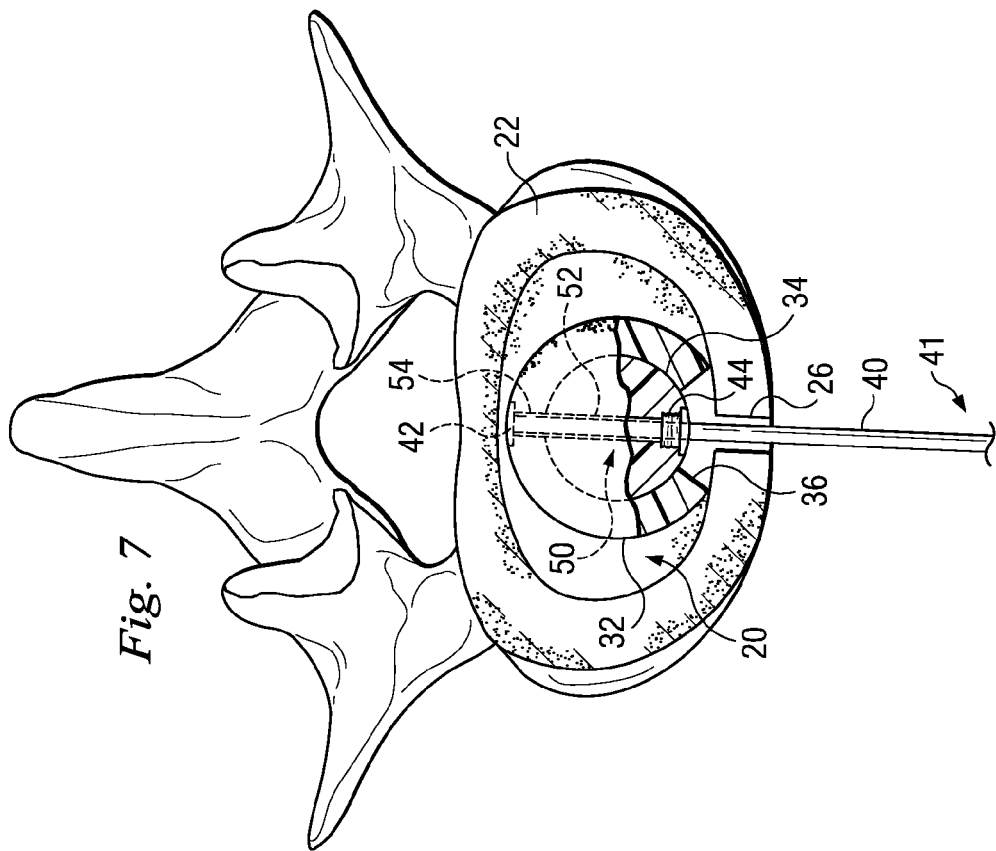
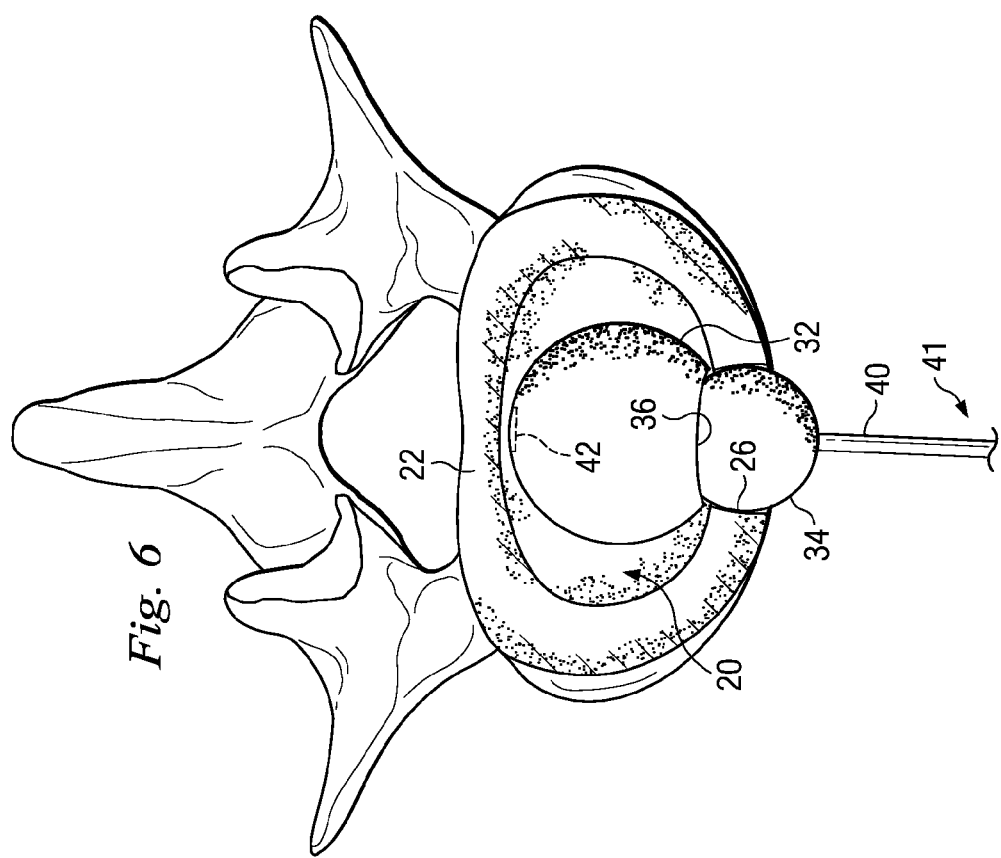

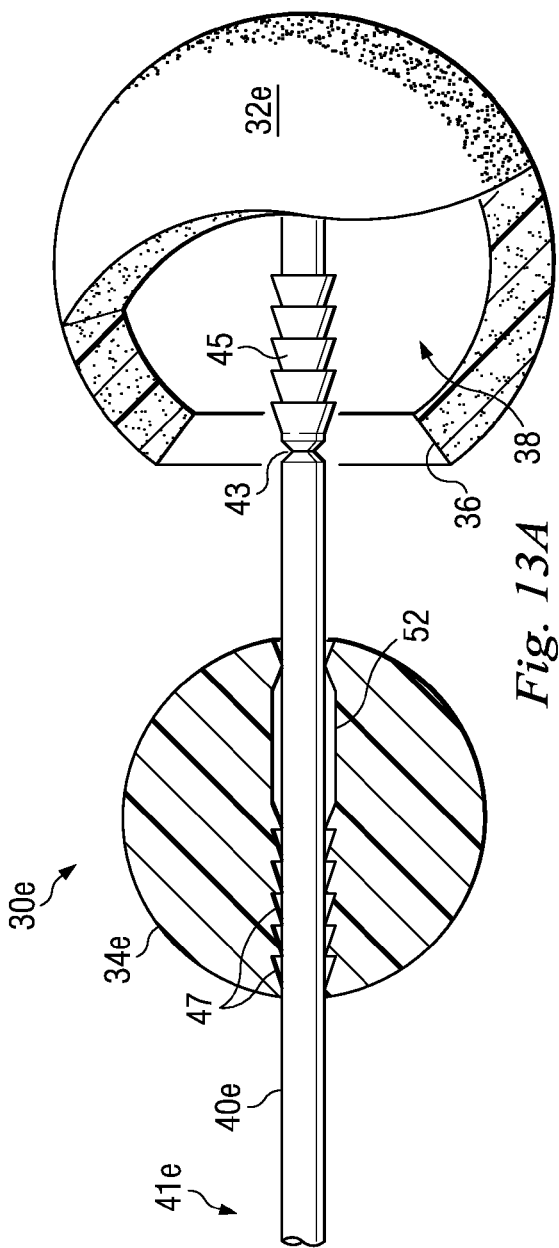
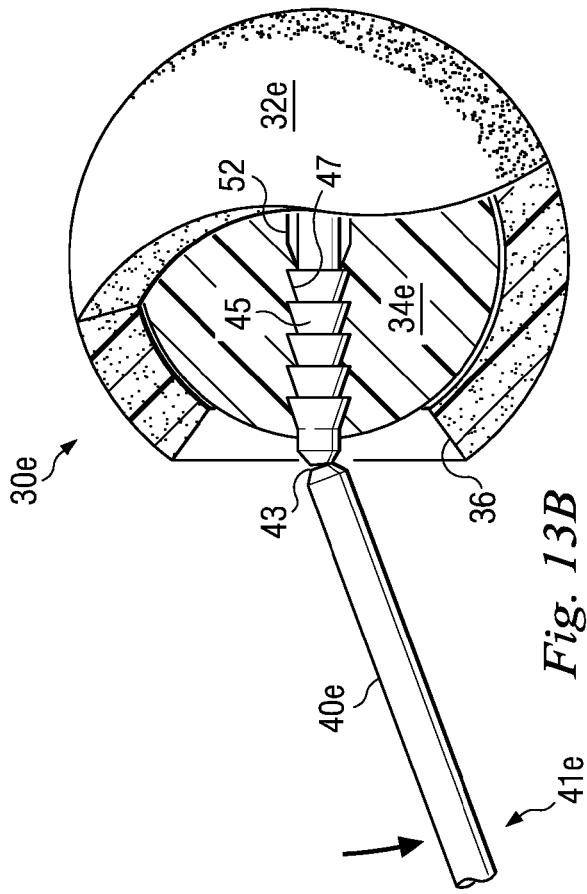
Fig. 13A
Fig. 13B

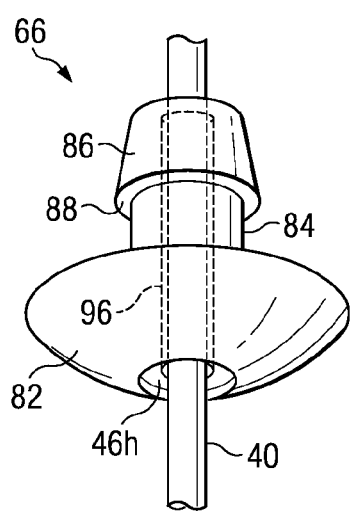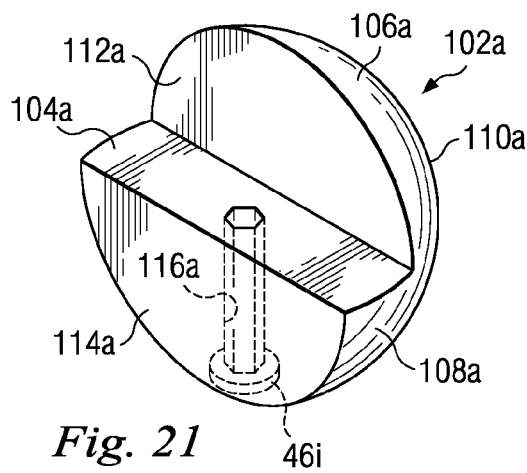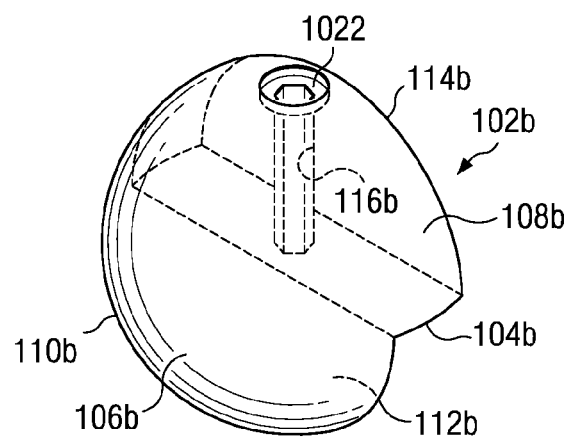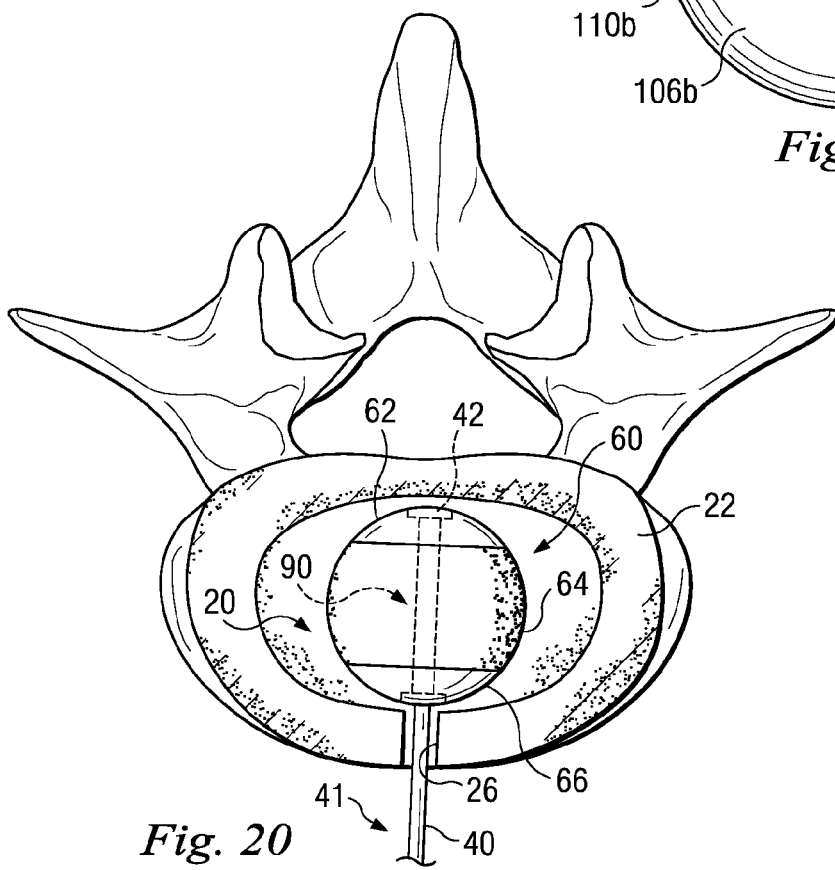

SPINAL NUCLEUS REPLACEMENT IMPLANTS

BACKGROUND

This disclosure is related to application Ser. No. 12/356,702, having the same filing date as this disclosure, titled, "Spinal Nucleus Replacement Methods".

The present disclosure relates generally to devices and methods for relieving disc degeneration or injury, and more particularly, to devices and methods for augmenting or replacing a nucleus pulposus. Within the spine, the intervertebral disc functions to stabilize and distribute forces between vertebral bodies. The intervertebral disc comprises a nucleus pulposus which is surrounded and confined by the annulus fibrosis.

Intervertebral discs are prone to injury and degeneration. For example, herniated discs typically occur when normal wear, or exceptional strain, causes a disc to rupture. Degenerative disc disease typically results from the normal aging process, in which the tissue gradually loses its natural water and elasticity, causing the degenerated disc to shrink and possibly rupture.

Intervertebral disc injuries and degeneration may be treated by fusion of adjacent vertebral bodies or by replacing the intervertebral disc with a prosthetic. To maintain as much of the natural tissue as possible, the nucleus pulposus may be supplemented or replaced while maintaining all or a portion of the annulus.

It would be advantageous to keep any incision into the annulus minimal, in order to avoid injuring healthy tissue. As such, it would be an addition to the field of art to provide a multi-piece device that may be assembled within the annulus.

SUMMARY OF THE INVENTION

In one exemplary aspect, the present disclosure is directed to an intervertebral prosthesis apparatus implantable within a disc space, disposed between upper and lower vertebral endplates, via an opening in the annulus extending around the disc space. The prosthesis may include a plurality of prosthesis modules insertable in a direction through the opening into the disc space, the modules having at least one set of complementarily-shaped and sized surfaces. The surfaces may be configured to engage within the disc space in a manner that the modules form an assembled prosthesis of a size substantially preventing it from being outwardly expelled from the disc space through the opening. The modules may have bearing surfaces slidably engageable with the endplates to permit articulation between upper and lower vertebral endplates.

In another exemplary aspect, the present disclosure is directed to an intervertebral prosthesis apparatus implantable within a disc space between two vertebra endplates. The apparatus may include a plurality of prosthesis modules each having a guide passage extending therethrough along an axis. The modules may be configured to be assembled within the disc space, to form the prosthesis, in a nested relationship in which the guide passages are coaxially aligned with one another.

In another exemplary aspect, the present disclosure is directed to a system for implantation of an intervertebral prosthesis within a disc space, between a first vertebra endplate and a second vertebra endplate, via an opening in the annulus extending around the disc space. The system may include a plurality of prosthesis modules insertable in a direction through the opening into the disc space. The modules may have at least one set of complementarily-shaped and sized surfaces. The modules may be configured to engage at least one set of complementarily-shaped and sized surfaces within the disc space to form an assembled prosthesis of a size substantially preventing it from being outwardly expelled from the disc space through the opening. The modules may have bearing surfaces slidably engageable with the endplates. The system also may include an elongated guide for inserting the modules into the disc space.

In yet another exemplary aspect, the present disclosure is directed to a system for implantation of an intervertebral prosthesis within a disc space, between two vertebra endplates. The system may include first and second modules having a first guide passage and a second a guide passage respectively extending therethrough along an axis, the modules being configured in a manner to be assembled within the disc space, to form the prosthesis, in an interfacing relationship in which the guide passages are coaxially aligned with one another. The modules may have bearing surfaces slidably engageable with the endplates to permit articulation between upper and lower vertebral endplates. The system also may include an elongated guide for inserting the modules into the disc space.

In another exemplary aspect, the present disclosure is directed to a method of implanting an intervertebral prosthesis within a disc space, between an upper vertebra endplate and a lower vertebra endplate. The method may include inserting a first end of a guide into the disc space; positioning a portion of a first prosthesis module about the guide; guiding the first prosthesis module into the disc space along the guide; and guiding a second prosthesis module into the disc space along the guide.

In another exemplary aspect, the present disclosure is directed to a method of providing separation and relative movement within a disc space between a first vertebra endplate and an adjacent second vertebra endplate. The method may include inserting first and second components for assembly into a prosthesis in the disc space; assembling the first and second components into the prosthesis so that a first load-bearing surface slidably engages the first vertebra endplate, and a second, generally opposed, load-bearing surface slidably engages the second vertebra endplate.

In another exemplary aspect, the present disclosure is directed to a method of implanting an intervertebral prosthesis between upper and lower vertebral endplates. The method may include introducing a first module through an opening in an annulus extending around the disc space, the first module having a bearing surface configured to allow sliding of one of the upper and lower endplates along the bearing surface; introducing a second module through the opening in the annulus, the first and second modules having complementary surfaces; engaging the complimentary surface of the first module with the complementary surface of the second module to form an assembled prosthesis of a size substantially preventing it from being outwardly expelled from the disc space through the opening so that the one of the upper and lower endplates slides along the bearing surface.

BRIEF DESCRIPTION OF THE DRAWINGS

FIG. 4 is a perspective view of a nucleus replacement prosthesis assembly embodying principles of the present invention.

FIGS. 5-7 sequentially illustrate a method, embodying principles of the present invention, of inserting the FIG. 4 prosthesis into the disc space shown in FIG. 2.

FIGS. 13A-B collectively illustrate a partially cut-away orthogonal view of a fourth alternate embodiment of the FIG. 4 assembly and an associated method of inserting its prosthesis portion into the disc space shown in FIG. 2.

FIGS. 17-20 collectively illustrate a fifth alternate embodiment of the FIG. 4 assembly and an associated method of inserting its prosthesis portion into the disc space shown in FIG. 2.

FIGS. 21 and 22 illustrate prosthesis module portions of a sixth alternate embodiment of the FIG. 4 assembly.

DETAILED DESCRIPTION

Figure 1:
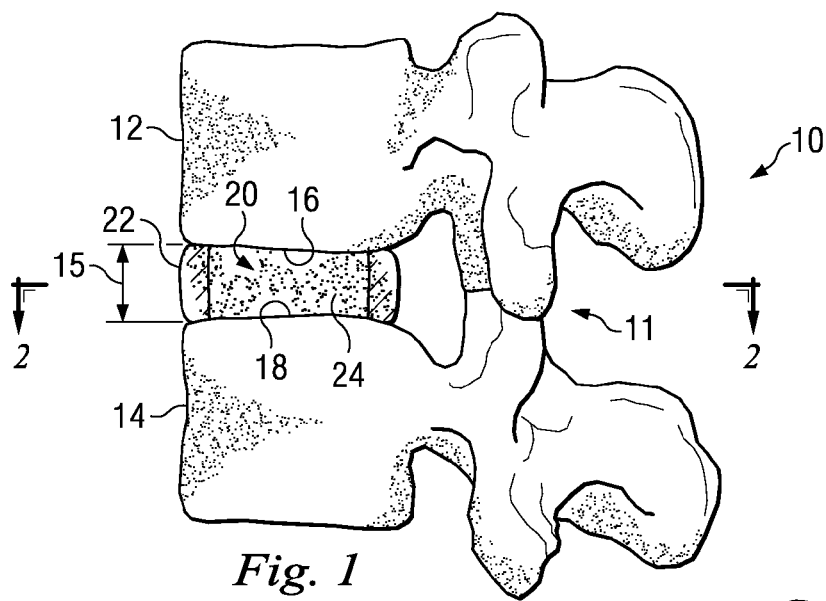
FIG. 1 is a partially cut-away lateral side elevation view of a section of a vertebral column.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Referring first to FIG. 1, the reference numeral 10 refers to a vertebral joint section or a motion segment of a vertebral column. The joint section 10 includes adjacent vertebral bodies 12, 14. The vertebral bodies 12, 14 include endplates 16, 18, respectively. An intervertebral disc space 20 is located between the endplates 16, 18, and an annulus fibrosus 22 surrounds the space 20. In a healthy joint, the space 20 contains a nucleus pulposus 24 within the disc space 20, which helps maintain the distance between endplates 16, 18, known as the disc height 15. Proper disc height 15 may vary for a particular patient, but medical experts understand how to determine a range of desired disc height 15. The nucleus pulposus 24 may degenerate with age, disease, or trauma, permitting the endplates 16, 18, to move closer together.

Figure 2:
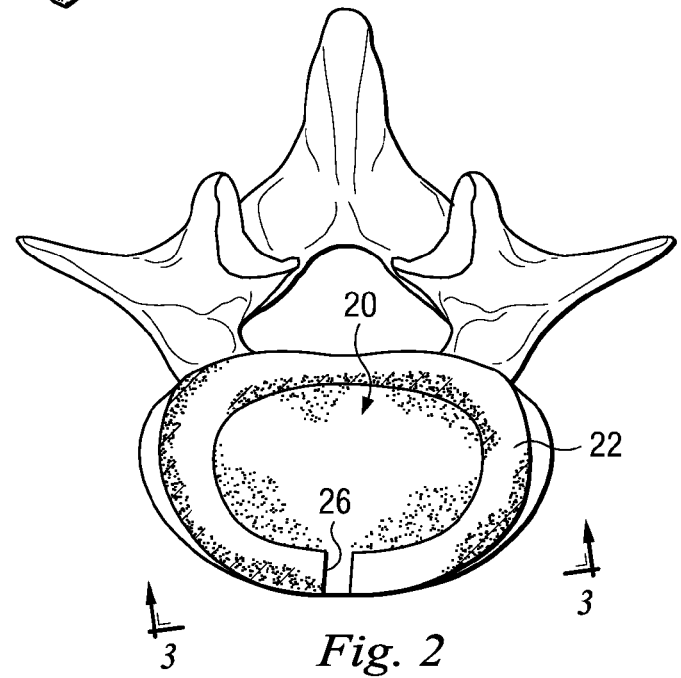
FIG. 2 is a transverse cross-sectional view through the vertebral column taken generally along line 2-2 of FIG. 1.
Figure 3:
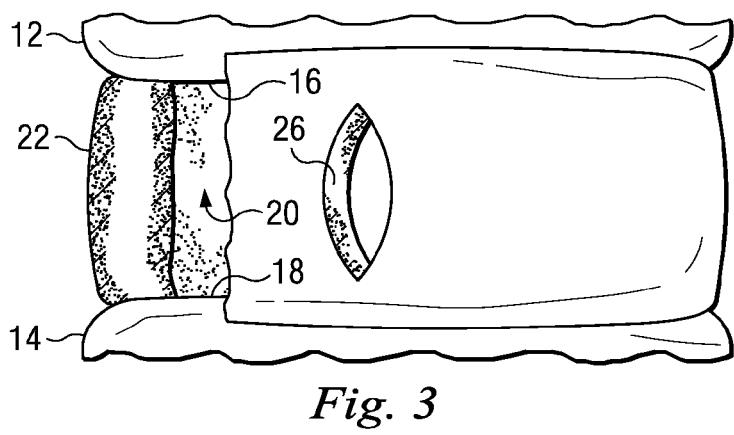
FIG. 3 is an enlarged scale, partially cut-away and vertically foreshortened anterior side elevation view of the vertebral column section taken generally along line 3-3 of FIG. 2.

Referring now to FIGS. 2 and 3, an exemplary disc incision 26 is shown in the anterior wall of the annulus fibrosus 22. Disc incision 26 breaches the annulus fibrosus 22 to the disc space 20. As necessary, nucleus pulposus 24 may be removed from the disc space 20 in order to accommodate the insertion of a prosthesis. Illustratively (representatively shown empty in FIG. 2), the disc incision 26 is longitudinal in order to attempt to minimize trauma to the annulus fibrosus 22. The anterior wall of the annulus fibrosus 22 is shown, but the depicted procedure and device are not limited by the example. The particular surgical expert performing the procedure may choose to enter the annulus fibrosus 22 from anterior oblique, posterior, posterior oblique, lateral, transforaminal, or any other approach judged suitable with regard to other factors. The particular surgical expert may also choose to orient the disc incision 26 differently.

A dilator may be used to dilate the disc incision 26, making it large enough to deliver the implant to replace or augment the disc nucleus. The dilator may stretch the disc incision 26 temporarily and avoid tearing so that the disc incision 26 can return back to its undilated size after the dilator instrument is removed. Although some tearing or permanent stretching may occur, the dilation may be accomplished in a manner that allows the disc incision 26 to return to a size smaller than the dilated size after the implantation is complete.

Referring now to FIG. 4, a specially designed prosthesis 30 embodying principles of the present invention is depicted therein and includes a generally spherical outer body 32, with a generally spherical outer body cavity 38 therein. The outer body 32 and the outer body cavity 38 have generally the same center. The outer body 32 includes an outer body opening 36 that provides access to the outer body cavity 38 from outside the outer body 32. The outer body opening 36 is generally circular in a plane normal to an axis A through the center of the outer body 32, with the axis passing through the center of the outer body opening 36. The diameter of the outer body opening 36 is less than the maximum diameter of the outer body cavity 38.

Outer body 32 may be formed from a material having a relatively low modulus of elasticity. The material forming the outer body 32 should perform essentially similarly to the elastic properties of an intervertebral disc. The material should resist deformation, yet slightly yield to distribute the encountered forces uniformly to the endplates 16, 18. A suitable material may possess a limited degree of elastic compliance or compressibility; while still being sufficiently rigid to substantially maintain the same general geometry. A suitable material may measure around 80 Shore A. Potentially suitable materials may include polyurethane, silicone, polyurethane-silicon copolymers, polyolefins, such as polyisobutylene rubber and polyisoprene rubber, neoprene rubber, nitrile rubber, vulcanized rubber, and combinations thereof.

The outer body 32 also includes an outer body guide passage 54, opposite the center of the outer body opening 36 that provides access to the outer body cavity 38 from outside the outer body 32. The outer body guide passage 54 has a generally circular cross-section and is generally centered on the axis A.

The prosthesis 30 also includes a generally spherical inner body 34, which is nestable within the outer body 32, as subsequently described herein. The diameter of inner body 34 is slightly smaller than the diameter of the outer body cavity 38, such that when positioned within outer body cavity 38, the outer surface of inner body 34 generally uniformly abuts with the surface of outer body cavity 38. Inner body 34 also includes a diametrically extending inner guide passage 52, which extends completely through the inner body and has a circular cross-section.

The system for employing prosthesis 30 also includes a cylindrical, elongated guide 40 of a diameter slightly less than outer body guide passage 54 and inner body guide passage 52. One end of guide 40 has a guide end cap 42 that is generally circular normal to the length of the guide 40. Guide end cap 42 is greater in diameter than guide 40, effectively preventing outer body 32 from moving off the length of guide 40. Exemplary outer body 32 has a guide end cap recess 322, so as to permit guide end cap 42 to lay relatively flush to the surface of outer body 32. The end surface of guide end cap 42 may be curved to approximately match the curvature of the outer surface of the ball-shaped outer body 32. Recesses and curved surfaces reduce the likelihood of injury to tissue the device components may contact.

The other end of guide 40 is the guide free end 41. An annular flanged anchor 44 may be disposed over guide free end 41. The annularity of anchor 44 permits anchor 44 to slide along the length of guide 40. Anchor 44 is illustratively formed to be plastically deformed against guide 40 so as to be fixable at any point along the length of guide 40. Coaxially disposed within one end of the inner body guide passage 52 is a tubular anchor receiver 46 that provides an interface with inner body 34 for anchor 44, so that anchor 44 may rest relatively flush to the outer surface of inner body 34. Anchor 44 and anchor receiver 46 are described and shown in greater detail below.

The diameter of the inner body 34 is slightly greater than the diameter of the outer body opening 36, such that with slight elastic deformation outer body opening 36 can expand to permit the passage of inner body 34 from outside of the outer body 32 into the outer body cavity 38. After the inner body 34 passes through the outer body opening 36, the outer body opening 36 reverts generally to its original diameter. As such, the migration of the inner body 34 outwardly through the outer body opening 36 will not occur under conditions generally experienced during the functional operation of the nested prosthesis 30.

The inner body 34 may be formed from a material having a relatively high modulus of elasticity. The material forming the inner body 34 should provide rigidity and support to outer body 32 when inserted therein, and resist compressive forces applied thereto by the end plates 16 and 18 in order to maintain the disc height 15. A suitable material may measure around 50 Shore D. Potentially suitable materials may include polyethylene, polyester, and polyetheretherketone (PEEK), among others. A suitable material may incorporate fibers, non-woven mesh, woven fabric, or braided structures. In a further alternative, inner body 34 is formed of a metal such as stainless steel, cobalt chrome or titanium, among others.

Referring now to FIGS. 3-7, prosthesis 30 may be operatively positioned within the disc space 20 by inserting the guide end cap 42 end of guide 40 through the annulus 22 at disc incision 26 and into disc space 20. Considering that the vertebral column is positioned dorsally, the guide 40 may be sufficiently long to extend from the disc space 20, through disc incision 26 and through the neck or abdomen of the body. With the guide in place, the other components may be directed to the exact location in the vertebral column by being placed on the guide at the guide free end 41, and moved along the length of the guide 40.

The next component installed is the outer body 32. Outer body 32 is placed on guide 40 by inserting the guide free end 41 through outer body guide passage 54 and through outer body opening 36. Outer body 32 is then moved along guide 40 until outer body 32 reaches the disc incision 26. At the disc incision 26 outer body 32 is compressed from the sides narrowing and elongating the outer body 32, as depicted in FIG. 5. So deformed, outer body 32 may be pushed through the annulus 22 at disc incision 26 that is smaller in diameter than the non-deformed diameter of outer body 32. The outer body 32 may be coated with a lubricious substance in order to facilitate insertion through the disc incision 26. Once through the annulus 22 at disc incision 26, exemplary outer body 32 elastically substantially resumes its original shape within the disc space 20 (see FIG. 6), and contacts both endplates 16, 18.

The next component installed is the inner body 34. Inner body 34 is placed on guide 40 by inserting the guide free end 41 through inner body guide passage 52 from the side opposite the anchor receiver 46. Inner body 34 is then moved along guide 40 until inner body 34 reaches the disc incision 26. Being smaller in diameter than the outer body 32, the inner body 34 is pushed through the similarly small disc incision 26, as shown in FIG. 6. Upon entry into the disc space 20, inner body 34 contacts outer body 32. With both the inner body 34 and the outer body 32 coaxially positioned on guide 40, inner body 34 contacts outer body 32 at the outer body opening 36. Sufficient force is applied to inner body 34 to elastically deform outer body opening 36 slightly in order to push inner body 34 through outer body opening 26 and into outer body cavity 38. Either or both outer body opening 26 and inner body 34 may be coated with a lubricious substance in order to facilitate the passage of inner body 34 through outer body opening 26.

Any fluid matter that may be within outer body cavity 38 will be displaced around guide 40, through outer body guide passage 54 or inner body guide passage 52, around inner body 34, through outer body opening 36, or through vents (not shown) positioned through the wall of outer body 32, or the inner body 34. Since guide 40 travels through both the outer body guide passage 54 and the inner body guide passage 52, the two guide passages align to form guide passage 50 (see FIG. 7).

Guide 40, and the now nested outer body 32 and inner body 34 are fixed together in the disc space 20 by sliding anchor 44 inwardly along the length of guide 40. When anchor 44 comes in contact with inner body 34, guide end cap 42 is drawn snugly against outer body 32 by pulling the guide free end 41 away from the nested prosthesis 30. At the same time anchor 44 is pushed into anchor receiver 46, thereby causing anchor 44 to lock into anchor receiver 46. In the illustrated embodiment, the anchor 44 is friction locked by an interference fit between the anchor receiver opening and the outer surface of the anchor and an interference fit between the inner surface of the anchor and the outer surface of guide 40. Guide 40 may then be cut off generally flush with anchor 44 leaving the assembled nested prosthesis 30 implanted in the disc space 20. A short segment of guide 40 that may remain after guide 40 is cut is kept from contact with the annulus 22 by being recessed in outer body opening 36.

Figure 8:
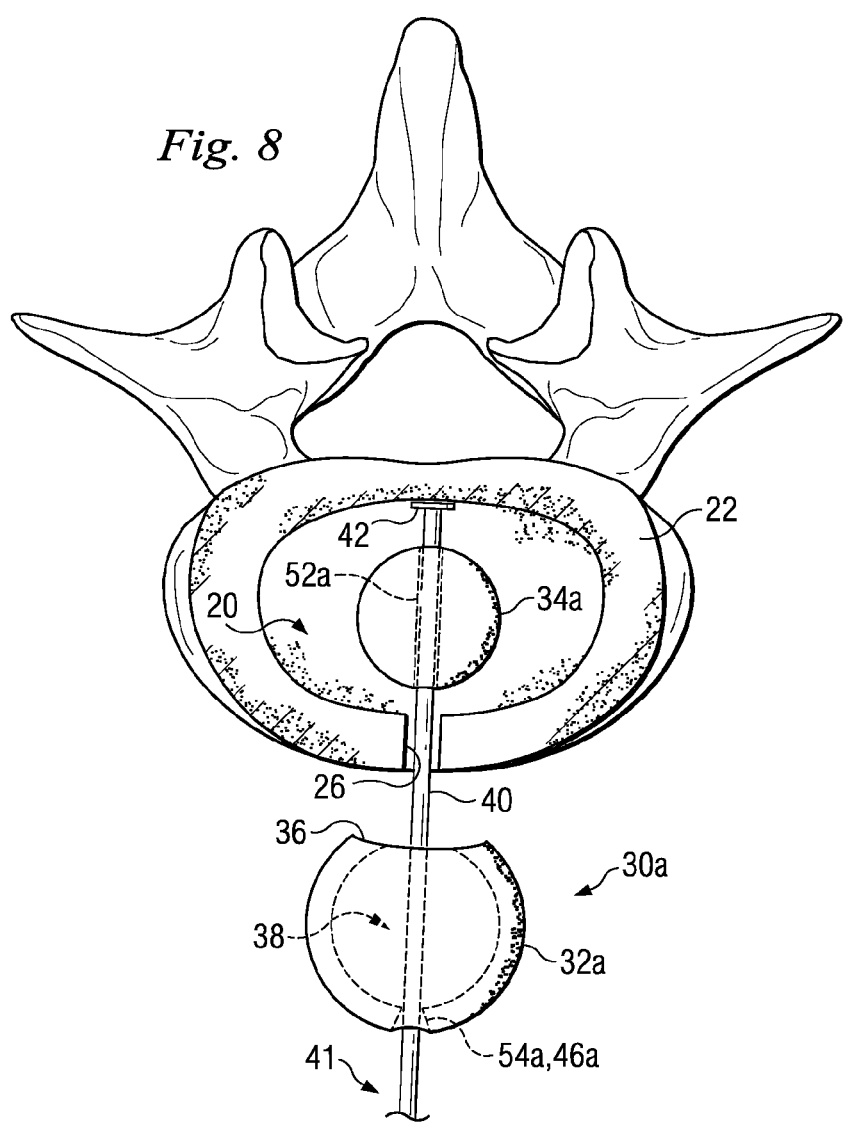
FIG. 8 depicts a first alternate embodiment of the FIG. 4 assembly useable to carry out the prosthesis insertion method shown in FIGS. 5-7.

Utilizing a first alternate prosthesis embodiment 30a, shown in FIG. 8, after the guide 40 is introduced into the disc space 20, the inner body 34a may be inserted into the disc space 20, prior to the outer body 32a. In this modification, the inner body 34a would contact the guide end cap 42, and as such would not require an anchor receiver 46. Therefore, inner body guide passage 52a may extend uniformly through the axis of inner body 34a.

With the inner body 34a inserted into the disc space 20, outer body 32a is placed on guide 40 by passing guide 40 through outer body opening 36, outer body cavity 38, and then outer body guide passage 54a. Since outer body 32a would interface with an anchor 44, the outer body guide passage 54a of outer body 32a may include an anchor receiver 46a on the end of outer body guide passage 54a that opens to the exterior of outer body 32a. So located, anchor receiver 46a, in outer body 32a, is accessible to an anchor 44a annularly placed on the guide 40 after the outer body 32a.

Similarly to the process described above, in conjunction with prosthesis 30a, outer body 32a travels the length of guide 40 until outer body 32a reaches the disc incision 26. At the disc incision 26 outer body 32a is compressed from the sides narrowing and elongating the outer body 32a. So deformed, outer body 32a may then be pushed inwardly through the disc incision 26. Upon entry into the disc space 20, outer body 32a contacts inner body 34a. With both the inner body 34a and the outer body 32a coaxially positioned on guide 40, outer body 32a contacts inner body 34a at the outer body opening 36. Sufficient force is applied to outer body 32a to elastically deform outer body opening 36 slightly in order to push inner body 34a through outer body opening 36 and into outer body cavity 38. Any fluid matter that may be within outer body cavity 38 will be displaced around guide 40, through outer body guide passage 54a or inner body guide passage 52a, around inner body 34a, through outer body opening 36, or through vents (not shown) positioned through the wall of outer body 32a, or the inner body 34a.

The components of the now nested prosthesis 30a disposed within disc space 20 are fixed together in the disc space 20 in a similar fashion as described above for prosthesis 30; by sliding anchor 44 annularly down the length of guide 40. Anchor 44 is then fixed at a specific position along the length of guide 40 by plastic deformation from forced insertion into anchor receiver 46a.

The current invention lends itself to a number of configurations for the guide 40, the interface of the guide 40 with the inner body 34 and the outer body 32, and either securing part of the guide 40 in the prosthesis or removing the guide 40 from the prosthesis. Variations in configurations equivalent to the configurations described herein are included in the current invention, and anticipated by the current disclosure. Examples of such variations are seen in the embodiments of the nested prostheses 30 and 30a, and in 30b, described immediately below.

In at least one embodiment, guide member 40 is formed of a biocompatible metal such as stainless steel or titanium. In an alternative embodiment, guide member 40 is formed of a polymer similar to the material of the implant device. Further, when formed of a radiolucent material, such as a polymer, radiopaque markers or materials may be added to the guides rod to enhance visualization. Still further, one or more of the individual components of the modular prosthesis in alternative embodiments include radiopaque elements or markers to assist in visualization during implantation. In one form, the outer body includes a first radiopaque marker and the inner body included a second radiopaque marker. When in the coupled or nested position for spacing the vertebrae, the first radiopaque marker may be aligned with the second radiopaque marker, thereby indicating proper placement. Further, more than one marker may be used on each of the inner body and the outer body.

Figure 9:
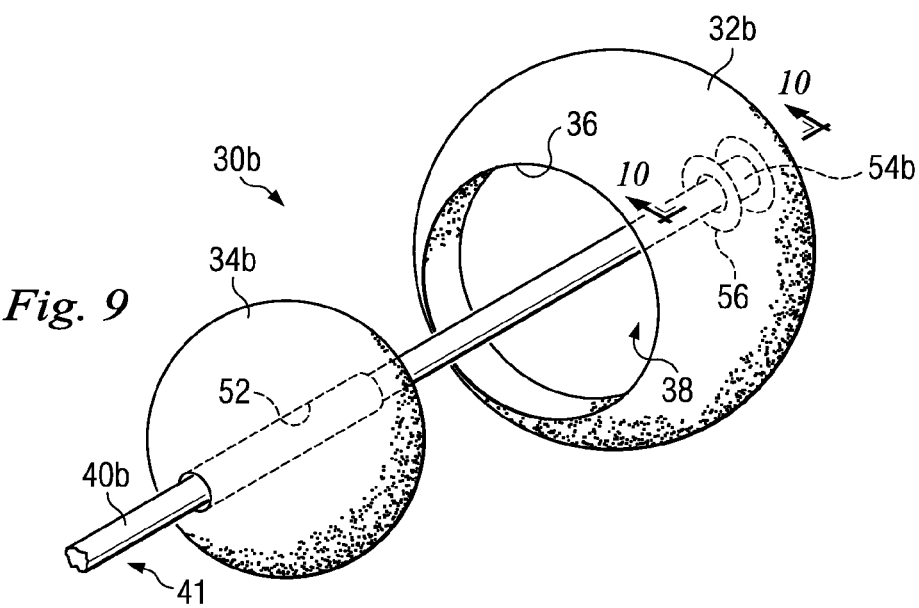
FIG. 9 is a perspective view of a second alternate embodiment of the prosthesis assembly.
Figure 10:
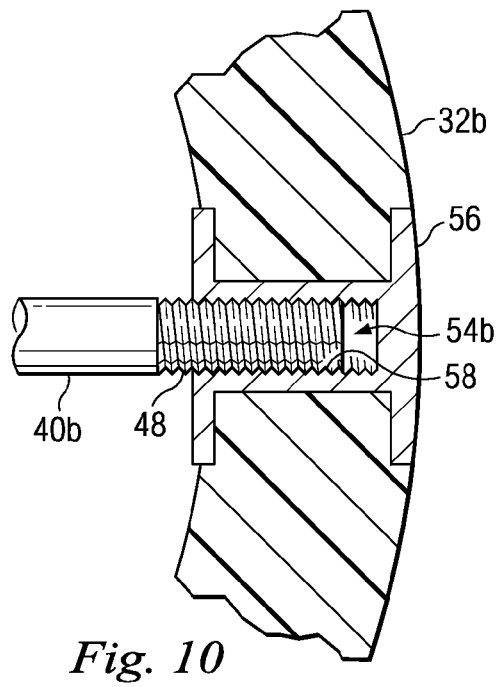
FIG. 10 is an enlarged scale, somewhat schematic, cross-sectional view taken through the FIG. 9 assembly generally along line 10-10 of FIG. 9, and illustrating the connection of one of its prosthesis modules to the assembly guide portion.

In a second alternate prosthesis embodiment 30b shown in FIGS. 9 and 10, outer body 32b has a modified outer body guide passage 54b. Outer body guide passage 54b has a guide seat 56, which in turn has seat threads 58. Modified guide 40b has guide threads 48 on one end that are complimentary to seat threads 58. To implant nested prosthesis 30b, guide 40b is first inserted through outer body opening 36 and outer body cavity 38 to be threadedly secured to outer body 32b in guide seat 56. Outer body 32b is then positioned adjacent to disc incision 26, where outer body 32b is compressed from the sides narrowing and elongating the outer body 32b. So deformed, outer body 32b may be pushed through the disc incision 26. Once through disc incision 26, outer body 32b elastically resumes it original shape within the disc space 20, and contacts both endplates 16, 18. The guide 40b remains secured to outer body 32b, and extends an operational distance through, and away from, disc incision 26.

The next component installed is the inner body 34b. Inner body 34b is then placed on the free end of guide 40b, with guide 40b passing through the inner body guide passage 52. Inner body 34 is then moved inwardly along the length of guide 40b, passing through the disc incision and outer body opening 36 to nest in the outer body cavity 38, similarly to the description above. With guide 40b positioned through outer body guide passage 54b and inner body guide passage 52, the two guide passages align to form guide passage 50b. With inner body 34 nested within outer body 32b guide 40b may be threadedly released from guide seat 56. Guide 40b may then be withdrawn from outer guide passage 50b, the disc space 20 and the disc incision 26, leaving the nested prosthesis 30b implanted in the disc space 20.

Figure 11:
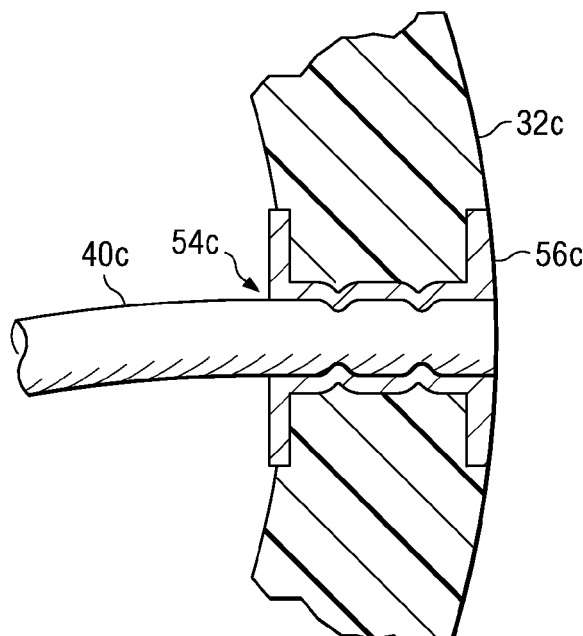
FIG. 11 is an enlarged scale, somewhat schematic, cross-sectional view of an alternate connection of one prosthesis module to an alternate assembly guide portion of those shown in FIG. 10.

Referring now to FIG. 11, an alternate outer ball 32c is integrally formed with an alternate guide seat 56c. Guide seat 56c fixedly secures an alternate flexible guide 40c within guide passage 54c. Flexible guide 40c may be comprised of monofilament cord made from suitable surgical materials such as surgical steel or plastic. Flexible guide 40c may alternatively be comprised of multiple-filament cord made from suitable surgical materials such as surgical steel or plastic, and may be configured into the cord by being braided or wound. Other metals, elements, compounds and polymers may also be understood to be suitable materials from which to construct flexible guide 40c.

Figure 12:
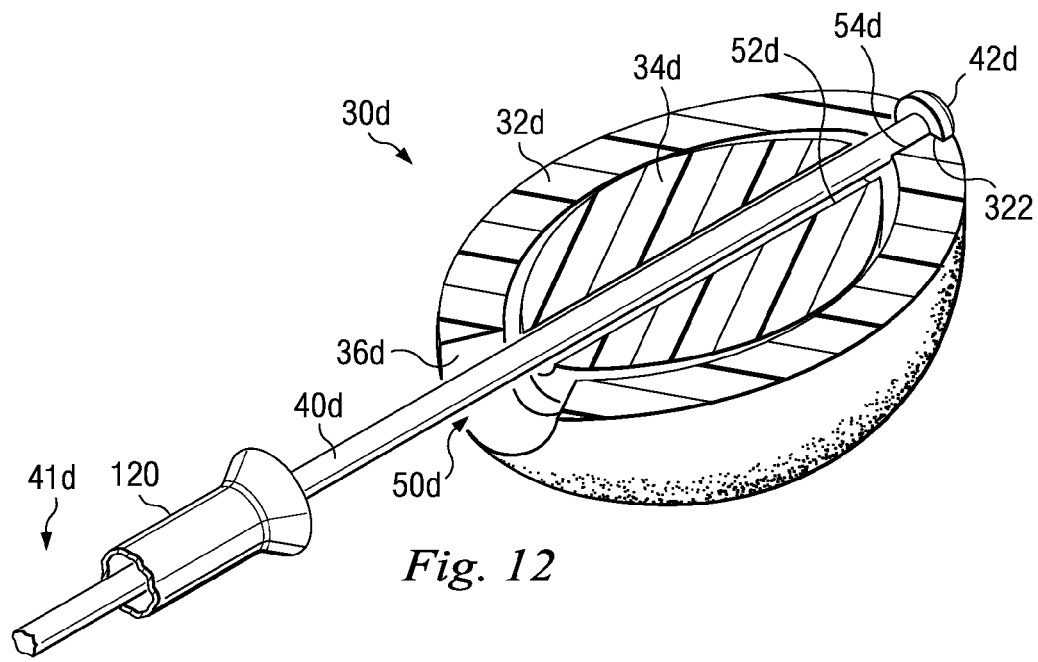
FIG. 12 is a partially cut-away perspective view of a third alternate embodiment of the FIG. 4 assembly, and a partial annular tool, useable in an associate method of inserting a prosthesis portion into the disc space shown in FIG. 2.

Referring now to FIG. 12, in third alternate embodiment 30d of the prosthesis, the outer body 32d and the inner body 34d have the general shape of complementary prolate spheroids. Outer body 32d and the inner body 34d may move along the length of guide 40d. Outer body 32d is limited to movement within the length of guide 40d by guide end cap 42, which may be recessed in guide recess 322. Guide 40d passes through outer body guide passage 54d and inner body guide passage 52d. An annular tool 120, which may be employed over guide free end 41d, may be used to apply force to inner body 34d in order to facilitate passage of inner body 34d through outer body opening 36d. With inner body 34d nested within outer body 32c, outer body guide passage 54d and inner body guide passage 52d align to form guide passage 50d. The alternate embodiment 30d is presented as an additional example of the potential modifications that may be made within the scope of the current invention. In a further embodiment, an outwardly extending rounded bulge (see FIG. 29) is formed on the exterior of the outer body 32 aligned with the guide passage 54. In some embodiments, the shape formed may approximate a human eyeball. The bulge on the spherical surface tends to orient the smooth bearing surfaces against the endplates while inhibiting bearing of the endplates adjacent guide passage 50. The shape of the components may be further varied without departing from the scope of the current invention.

Referring now to FIGS. 13A and 13B, in a fourth alternate embodiment 30e of the prosthesis, an outer body 32e, an inner body 34e and a guide 40e are structured and function similarly to the previous embodiments, however, the guide 40e incorporates a pawl interface component 45 and the inner body 34e incorporates a ratchet interface component 47 into its inner body guide passage 52e. Additionally, guide 40e has a frangible point 43 that possesses sufficient strength to survive insertion operation of guide 40e and the prosthesis components, but which will break when additional or differing force is applied, permitting the removal of the remainder of guide 40e attached to guide free end 41e.

The pawl interface component 45 and the ratchet interface component 47 are designed to complementarily cooperate to secure the components of the prostheses 30e together. As inner body 34e is inserted in to outer body 32e, ratchet interface components 47 engage pawl interface components 45, biasing against each other to restrict outward movement of inner body 34e. Once inner body 34e is secured within outer body 32e, guide 40 may be fractured at frangible point 43. The portion of guide 40e from the frangible point 43 to its connection with outer body 32e remain as part of the assembled prosthesis 30e, while the balance of guide 40e from the frangible point to the guide free end 41e may be removed.

The interaction of paw interface component 45 and ratchet interface component 47, in FIGS. 13A and 13B demonstrate one manner of securing the components of a prosthesis together in the disc space 20. The previously described alternate prosthesis component securement, comprising anchor 44 (shown in FIG. 7 above) is shown enlarged in FIGS. 14A and 14B.

Figure 14A:
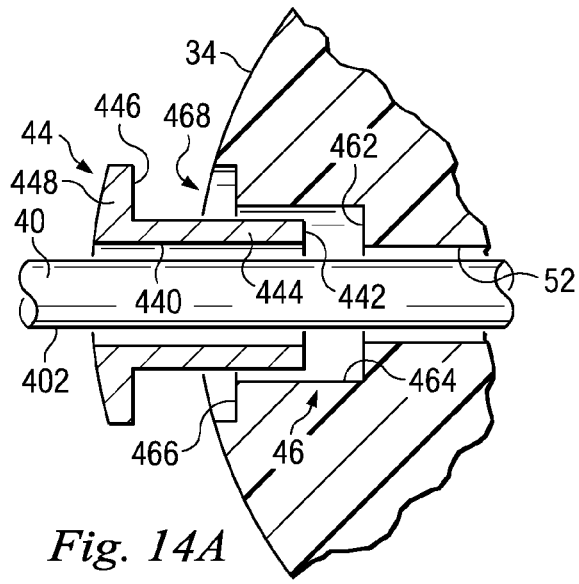
FIGS. 14A and 14B are enlarged scale, somewhat schematic, cross-sectional illustrations of the exemplary assembly and method of securing the guide, guide anchor and prosthesis module shown in FIG. 7.
Figure 14B:
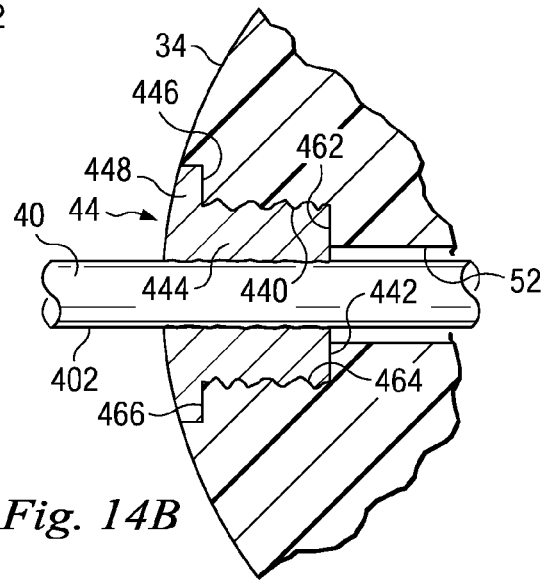

Referring now to FIGS. 14A and 14B, guide anchor 44 is situated annularly on guide 40, and moves along the length of guide 40 to be inserted into complementarily-shaped guide anchor receiver 46. Anchor 44 has an anchor shoulder 448 with an anchor shoulder face 446. Anchor 44 also has an anchor neck 444 and an anchor lead face 442. Interior to anchor 44 is an annular passage, circumferentially defined by an anchor inside surface 440, through which guide 40 passes. Anchor receiver 46 comprises an anchor well 448, having an anchor well base 462, an anchor well wall 464, and an anchor well recess base 466.

As anchor 44 is inserted into anchor receiver 46, anchor neck 444 enters anchor well 468 until anchor lead face 442 contacts anchor well base 462. Additional inward force is applied to anchor shoulder 448 until anchor shoulder 448 enters anchor well 448, with anchor shoulder face 446 in contact with anchor well recess base 466. Since the depth of anchor well 468 is less than the length of anchor neck 444, and the material of inner body 34 is sufficiently rigid, the additional force causes anchor neck 444 to buckle, biasing the anchor inside surface 440 against the guide outer surface 402. Additionally the anchor neck 444 may bias against the anchor well wall 464. Guide 40 may then be terminated adjacent to anchor 44, and the segment of guide 40 attached to the guide free end 41 may be removed.

Figure 15:
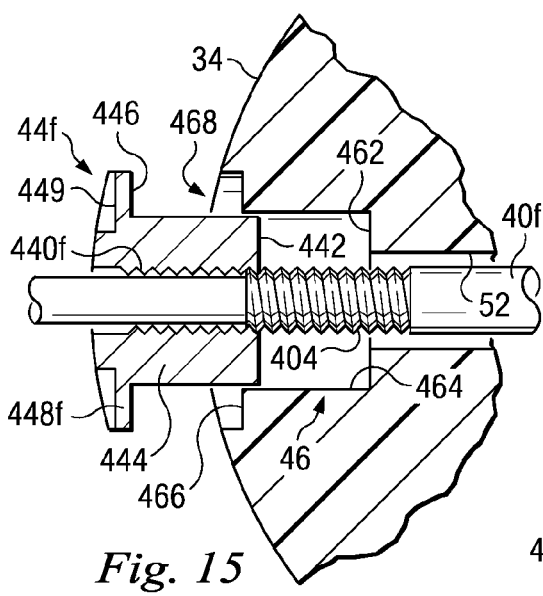
FIGS. 15 and 16 are enlarged scale, somewhat schematic, cross-sectional illustrations of alternate exemplary embodiments of assembly and method of securing guides, guide anchors and prosthesis modules to that shown in FIGS. 14A and 14B.

Referring now to FIG. 15, an alternate prosthesis component securement embodiment to that shown in FIGS. 14A and 14B may include a guide 40f that has a threaded section 404 on its outer surface. A complementary anchor 44f has a similar structure as the previously described anchor 44, except anchor inside surface 440f has threads that complement the threaded section 404. Additionally, anchor 44f may have an anchor shoulder 448f that has rotation engagement slots 449. A complementarily shaped annular tool 120 may engage rotation engagement slots 449 in order to apply rotation to anchor 44f.

In operation, anchor 44f is moved along the length of guide 40f to be inserted into guide receiver 46. Threaded section 404 may be precisely located on the length of guide 40f to interface with a complementary anchor 44f in anchor receiver 46. Anchor 44f is rotatably engaged on guide 40f to tighten against anchor well base 462 and secure the prosthesis components together. Guide 40f may then be terminated adjacent to anchor 44f, outside outer body 34, and the segment of guide 40f attached to the guide free end 41f may be removed.

Figure 16:
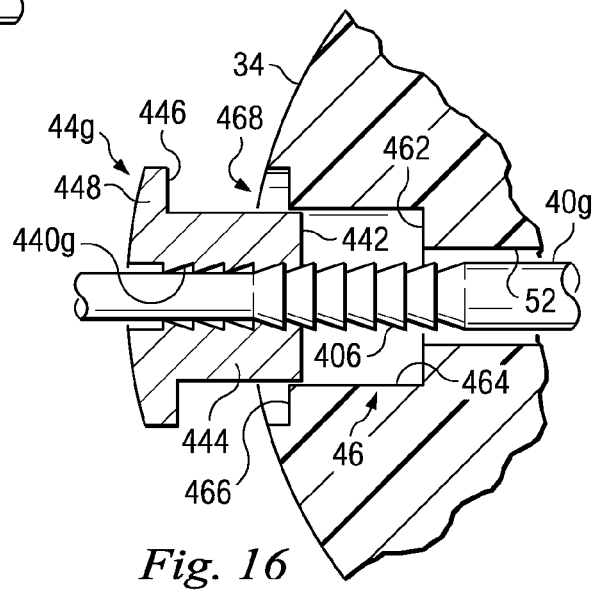
Figure 17:
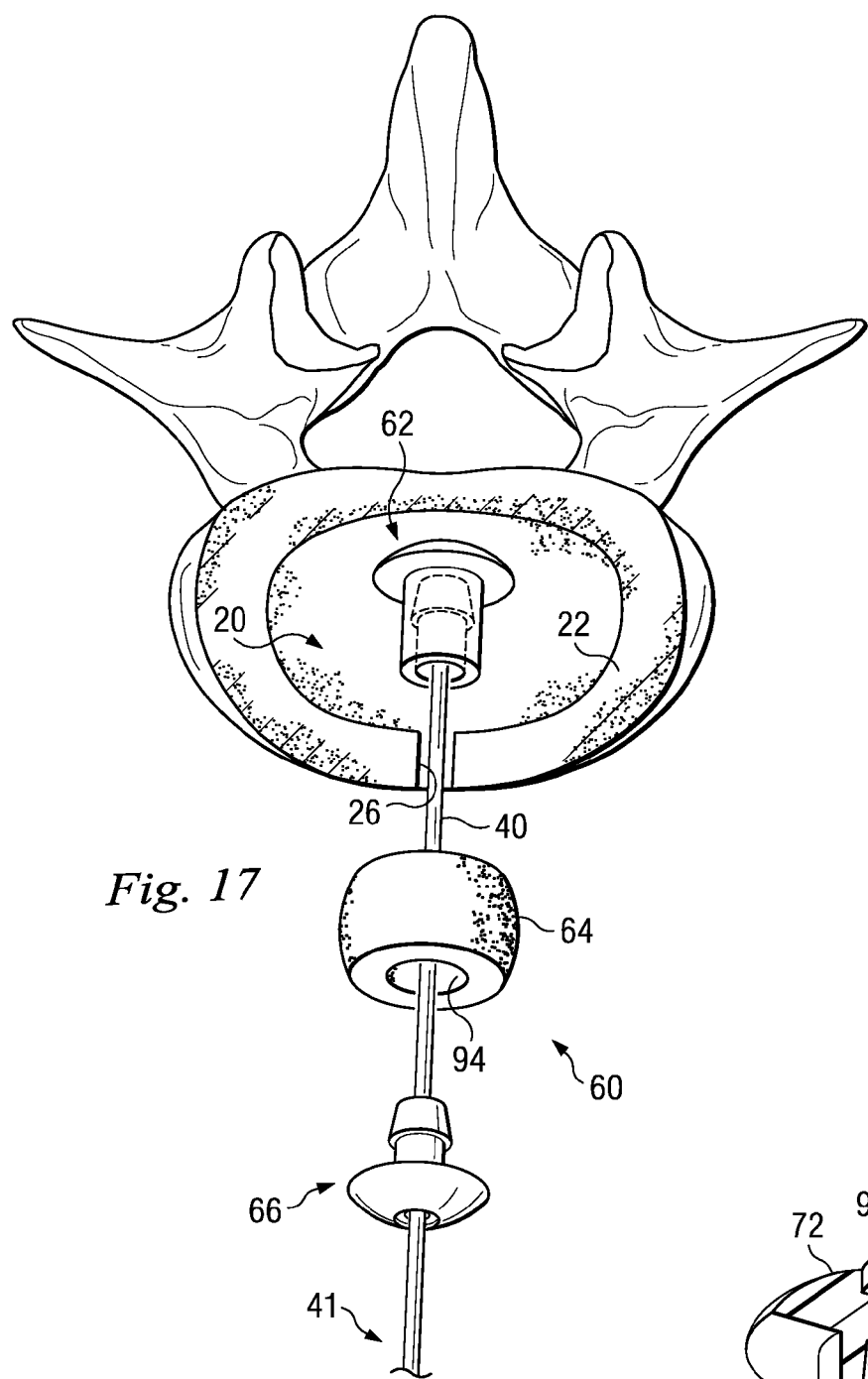
Figure 18:
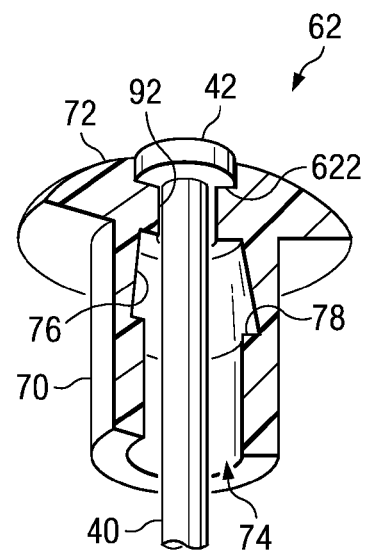

Referring now to FIG. 16, an additional alternate prosthesis component securement embodiment to that shown in FIGS. 14A and 14B may include a guide 40g that has a pawl interface section 406 on its outer surface. A complementary anchor 44g has a similar structure as the previously described anchor 44, except anchor inside surface 440g has a ratchet interface that complements the pawl interface section 406. A complementarily shaped annular tool 120 may be used to apply appropriate force to anchor 44g to adequately seat anchor 44g within anchor receiver 46.

In operation, anchor 44g is moved along the length of guide 40g to be inserted into guide receiver 46. Pawl interface section 406 may be precisely located on the length of guide 40g to interface with a complementary anchor 44g in anchor receiver 46. Anchor 44g is laterally forced along the length of guide 40g to push the anchor lead face against the anchor well base, which biases the pawl interface section 406 against the ratchet interface 440f, securing the prosthesis components together. Guide 40g may then be terminated adjacent to anchor 44g, outside outer body 34, and the segment of guide 40g attached to the guide free end 41g may be removed.

A fifth alternate prosthesis embodiment 60 is shown in FIGS. 17-20 and is comprised of more than two body components that may be assembled within the disc space 20 into a generally spherical shape. The components of the prosthesis 60 include a receiver body 62, an annular body 64, and an insert body 66.

Receiver body 62 (see FIG. 18) has a receiver neck 70, a receiver head 72, and a receiver well 74. The receiver neck 70 has a generally tubular shape and is transverse to the generally circular receiver head 72. The surface of the receiver well 74 has a receiver slope 76 at its inner end, and a strike 78 that is generally normal to the axis of the receiver neck 74. The receiver body 62 has a receiver body guide passage 92 that is generally cylindrical in shape and generally coaxial with the receiver neck 70. The receiver body guide passage 92 passes inwardly through the receiver head 72 and into the receiver well 74.

Insert body 66 (see FIG. 19) has an insert head 82 and an insert shaft 84. The insert shaft 84 has a generally cylindrical shape and is transverse to the generally circular insert head 82. The surface of the insert shaft 84 has an insert slope 86, and a latch 88 that is generally normal to the axis of the insert shaft 84. The insert body 66 has an insert body guide passage 96 that is generally cylindrical in shape and generally coaxial with the insert shaft 84. Insert body guide passage 96 passes through the insert head 82 and the insert shaft 84.

At one end of the insert body guide passage 96 is tubular anchor receiver 46h, having a slightly greater outer diameter than the diameter of the insert body guide passage 96. Anchor receiver 46h provides a recessed interface with insert body 66 for anchor 44, so that anchor 44 may rest relatively flush to the outer surface of insert body 66.

The shape of the receiver well 74 is complimentary to the shape of the insert shaft 84. The insert shaft 84 may be inserted into the receiver well 74. The shape of the insert slope 86 complements the shape of the receiver slope 76. The shape of the latch 88 compliments the shape of the strike 78. The receiver body 62 and the insert body 66 comprise material that though rigid enough to perform roles in maintaining proper disc height and vertebral support, is compressible to sufficient degree to permit insertion of the insert shaft 84 into the receiver well 74 to a point where the latch 88 engages the strike 78. The latch 88 biases against the strike 78 to prevent withdrawal of the insert shaft 84 from the receiver well 74 under conditions generally experience during the functional operation of the sandwiched prosthesis 60. The surface of the insert shaft 84 generally uniformly contacts the surface of the receiver well 74.

Receiver body 62 and the insert body 66 may be formed from a material having a relatively high modulus of elasticity. The material forming the receiver body 62 and the insert body 66 should provide rigidity and support to annular body 64, and resist compressive forces applied to the disc space 20 in order to maintain the disc height 15. A suitable material may measure around 50 Shore D. Potentially suitable materials may include a variety of polymers, such as polyethylene, polyester, and polyetheretherketone (PEEK). A suitable material may incorporate fibers, non-woven mesh, woven fabric, or braided structures.

Annular body 64 has a generally cylindrical shape, with a convex outside surface. The annular body 64 has a central axial annular guide passage 94 that is generally cylindrical in shape, and complementary to the diameter of the receiver neck 70. The receiver neck 70 may be inserted in to the annular guide passage 94, and the surface of the receiver neck 70 generally uniformly contacts the surface of the annular guide passage 94.

Annular body 64 may be formed from a material having a relatively low modulus of elasticity. In some embodiments, the material forming the annular body 64 should perform essentially similarly to the elastic properties of an intervertebral disc. For example, the material may resist deformation, yet slightly yield to distribute the encountered forces uniformly to the endplates 16, 18. A suitable material may possess a limited degree of elastic compliance or compressibility, while still being sufficiently rigid to substantially maintain the same general geometry. A suitable material may measure around 80 Shore A. Potentially suitable materials may include polyurethane, silicone, polyurethane-silicon copolymers, polyolefins, such as polyisobutylene rubber and polyisoprene rubber, neoprene rubber, nitrile rubber, vulcanized rubber, and combinations thereof.

Receiver body 62, the annular body 64 and the insert body 66 may move along the length of guide 40, from a guide free end 41 to a guide end cap 42 end. The receiver body guide passage 92, the annular guide passage 94 and the insert body guide passage 96 are alignable to form a prosthesis guide passage 90 (see FIG. 20).

After the guide 40 is introduced into the disc space 20, the receiver body 62 may be inserted into the disc space 20, prior to the annular body 64, and insert body 66. Receiver body 62 is placed on guide 40 by inserting the guide free end 41 through receiver body guide passage 92 from the receiver head 72, into the receiver well 74. Receiver body 62 is moved inwardly along the length of guide 40 until receiver body 62 reaches the disc incision 26. The receiver head 72 is smaller in diameter than the annular body 64. The receiver body 62 is manipulated through the similarly small disc incision 26, and moved along guide 40 until guide end cap 42 seats in recess 622.

With the receiver body 62 inserted into the disc space 20, annular body 64 is placed on guide 40 by passing guide 40 through annular guide passage 94. The annular body 64 is moved inwardly along the length of the guide 40 until the annular body 64 reaches the disc incision 26. The diameter of the annular body 64 is greater than the width of the disc incision 26. Annular body 64 fits loosely on guide 40, being that the diameter of annular guide passage 94 is greater than the diameter of the guide 40. As such, annular guide passage 94 may be angled to be less than perpendicular to the axis of the guide 40. Additionally, the annular body 64 may be compressed from the sides, narrowing and elongating the annular body 64. So angled and deformed, annular body 64 may be pushed through the disc incision 26. As the annular body 64 passes through disc incision 26, annular body 64 elastically expands to its original shape within the disc space 20, and contacts both endplates 16, 18. Annular body 64 is oriented such that annular guide passage 94 may receive receiver neck 70 of the receiver body 62 already within disc space 20. Annular body 64 is pushed onto receiver neck 70 until annular body 64 contacts receiver head 72.

With the receiver body 62 and annular body 64 inserted into the disc space 20, insert body 66 is placed on guide 40 by passing guide 40 through insert body guide passage 96, from the insert shaft 84 end. The insert body 66 is then moved inwardly along the length of the guide 40 until the insert body 66 reaches the disc incision 26. The insert head 82 is smaller in diameter than the annular body 64. The insert body 66 is manipulated through the similarly small disc incision 26, where insert body 66 contacts annular body 64 and receiver body 62. Since insert body 66, annular body 64 and receiver body 62 are each on common guide 40, receiver body guide passage 92, annular guide passage 94 and insert body guide passage 96 align. Insert shaft 84 is thereby positioned to insert into receiver well 74, which is positioned within annular guide passage 94.

The inserted guide 40, receiver body 62, annular body 64, and insert body 66 may be fixed together in the disc space 20 by sliding anchor 44 inwardly along the length of guide 40. When anchor 44 comes in contact with insert body 66, guide end cap 42 is drawn snugly against receiver body 62 by pulling the guide free end 41 away from the sandwiched prosthesis 60. At the same, time anchor 44 is pushed into anchor receiver 46d. Forcing anchor 44 into anchor receiver 46d causes anchor 44 to plastically deform; biased against the guide 40, fixing anchor 44 in place along the length of guide 40. Guide 40 may then be cut off generally flush with anchor 44 leaving the assembled sandwiched prosthesis 60 implanted in the disc space 20.

Alternatively, the shape of the walls of the receiver well 74 and the insert shaft 84 may be complementarily flat and parallel. Still further, receiver well 74 may be internally threaded and mate with external threads on the insert shift 84. The guide 40 and a fixed anchor 44 (such as shown in FIG. 7) may provide the primary force holding the prosthesis components together. The holding mechanisms previously disclosed for the embodiments of FIGS. 4-16 may also be applied to fix the components of FIGS. 17-20.

As a further alternative, the receiver body 62 may have a guide seat, similar to guide seat 56 in FIG. 10, and the prosthesis may be held together by the complementary shapes of its components. A guide similar to guide 40b, having guide threads opposite the guide free end 41, may be utilized, with the guide being releasable from the guide seat once the prosthesis is implanted in the disc space 20.

Referring now to FIGS. 21, 22, and 23A-C, a sixth alternate prosthesis embodiment, representatively in the form of a couplet prosthesis 100, is comprised of multiple components that may be assembled within the disc space 20 into a generally spherical shape. The components of the prosthesis 100 include two couplet components 102a, 102b. Each couplet component 102a, 102b has a couplet guide passage 116a, 116b, which upon assembly of the couplet components 102a and 102b, make a unified couplet guide passage 118 (see FIG. 23C). Couplet component 102a may have an anchor receiver 46i where its couplet guide passage 116a intersects the outer surface of couplet component 102a. Couplet component 102b may have a guide recess 1022 where its couplet guide passage 116b intersects the outer surface of couplet component 102b. The couplet guide passage 118 is a generally circular cylinder, circularly centered on the axis through the center of the assembled couplet prosthesis 100. In its assembled state, the prosthesis 100 has a spheroid configuration.

Each couplet 102a, 102b has a generally L-shaped configuration, with a first lobe 106a, 106b, and a somewhat larger second lobe 108a, 108b, which contains the couplet guide passage 116a, 116b. Each couplet 102a, 102b also has a first lobe face 112a, 112b, and a second lobe face 114a, 114b; each lobe face 112a, 112b, 114a, 114b being generally parallel with the axis through the center of the couplet prosthesis 100. Each couplet 102a, 102b also has a medial shelf 104a, 104b that is generally perpendicular to and intermediate the first lobe face 112a, 112b and the second lobe face 114a, 114b. In the exemplary embodiment the couplet guide passage 116a, 116b intersects with the general center of the medial shelf 104a, 104b. Each couplet 102a, 102b has a crown 110a, 110b that is a general area on what would be the outer surface of the assembled spherical couplet prosthesis 100, located generally the greatest distance away from both the first lobe face 112a, 112b and the second lobe face 114a, 114b.

In some exemplary alternative embodiments, the medial shelves 104a, 104b are not perpendicular to the lobe faces 112a, 112b, 114a, 114b. In these exemplary embodiments, the medial shelves are angled at an angle other than 90°. For example, in one exemplary embodiment, the shelves 104a, 104b are angled at 45°. In other exemplary embodiments the first lobe face, such as face 112a, may include a boss and the second lobe face, such as face 114b, may include a receiving pocket sized to receive the boss. The boss may have one side flush with the surface of the crown 110 and may disposed in alignment with the couplet guide passage. Such a boss and pocket may be helpful for aligning the two pieces.

Also, in some exemplary embodiments, the anchor receiver 46i or the guide recess may be noncircular, such as a square shape. These embodiments may be useable with a guide having a non-circular cross-section to inhibit rotation of the couplet 102a about the guide. Accordingly, in some embodiments, the guide may be used to turn the couplets to a desired orientation.

Figure 23B:
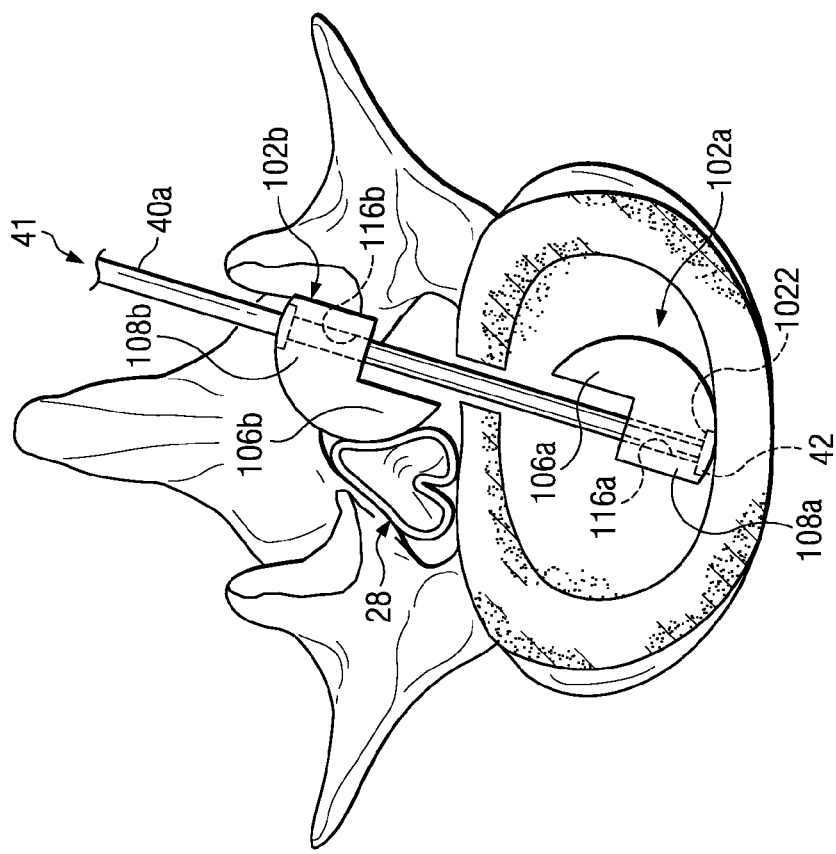
FIGS. 23A-C illustrate the sixth alternate assembly embodiment and an associated alternate method of inserting prosthesis into the disc space shown in FIG. 2.
Figure 23A:
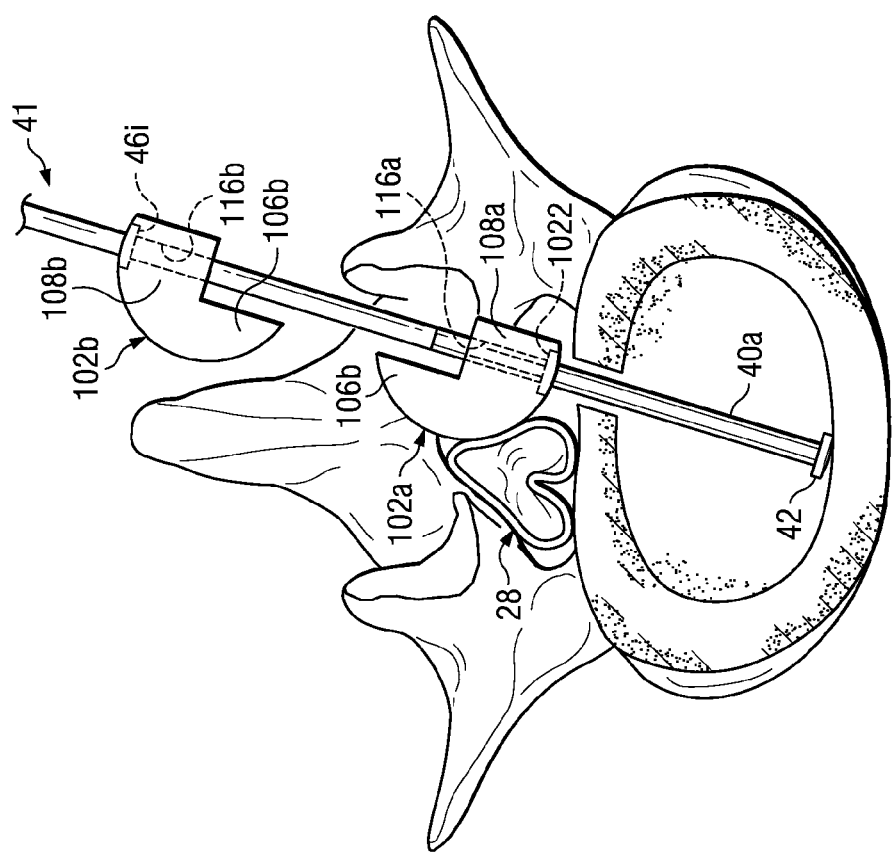
Figure 23C:
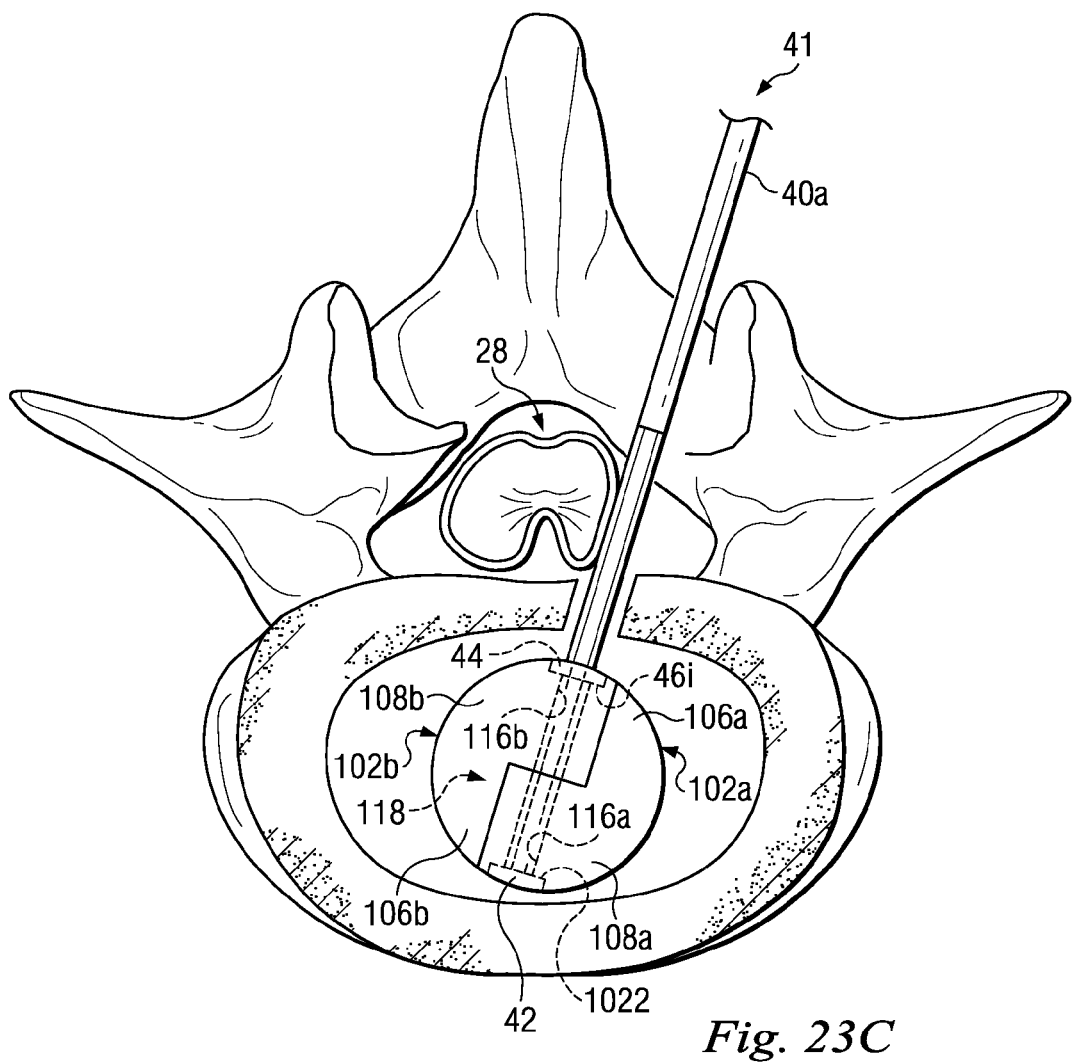

With reference now to FIGS. 23A-C, after the guide 40 is introduced into the disc space 20, the first couplet component 102b may be inserted into the disc space 20, prior to the second couplet component 102a. A generally posterior approach is shown, where the guide 40 approaches the disc space 20 through one side of the facet joint 11, but the method described may be used from other angles. From the shown angle, it may be necessary to remove a portion of the facet joint 11, in order to ease insertion of the components 102a, 102b, and also to reduce the amount of distraction. The distraction force to distract the disc space 20 may be asserted by a distraction device applied to the vertebral section.

First couplet component 102b is placed on guide 40 by inserting the guide free end 41 through couplet guide passage 116b from the outside surface of the first couplet component 102b. The first couplet component 102b in then moved inwardly along the length of guide 40 until the first couplet component 102b reaches the neural structure 28. Orienting the first couplet component 102b so that the curved surface of the second lobe 108b faces the neural structure 28 may avoid damage to the neural structure 28 that may be caused by contact with the more acute angles of the lobe faces 112b, 114b and medial shelf 104b. Alternatively, orienting the first couplet component 102b so that the narrower side of the second lobe 108b faces the neural structure 28, may permit the first couplet component 102b to pass the neural structure 28 with little or no contact.

The first couplet component 102b then approaches the disc incision 26. The first couplet component 102b is smaller in cross-section than the assembled spherically configured couplet prosthesis 100. The first couplet component 102b is manipulated through the similarly small disc incision 26, starting with the second lobe 108b. The disc incision 26 expands to accept the broadest region of the first couplet component 102b, defined by the crown 110b and the intersection of the medial shelf 104b and the second lobe face 114b. At the point the size of the first couplet component 102b begins to decrease and the first couplet component 102b moves into the disc space 20.

After the couplet component 102b is introduced into the disc space 20, the second couplet component 102a may be inserted into the disc space 20. The second couplet component 102a is placed on guide 40 by inserting the guide free end 41 through couplet guide passage 116a from the medial shelf 104a. The second couplet component 102a is then moved inwardly along the length of guide 40 until the second couplet component 102a reaches the neural structure 28. Orienting the second couplet component 102a so that the curved surface of the second lobe 108a faces the neural structure 28 may avoid damage to the neural structure 28 that may be caused by contact with the more acute angles of the lobe faces 112a, 114a and medial shelf 104a. Alternatively, orienting the second couplet component 102a so that the narrower side of the second lobe 108a faces the neural structure 28, may permit the second couplet component 102a to pass the neural structure 28 with little or no contact.

The second couplet component 102a then approaches the disc incision 26. The second couplet component 102a is the same size and general configuration as the first couplet component 102b. The second couplet component 102a is manipulated through the similarly small disc incision 26, starting with the first lobe 106a. The disc incision 26 expands to accept the broadest region of the second couplet component 102a, defined by the crown 110a and the intersection of the medial shelf 104a and the second lobe face 114a. At that point the size of the second couplet component 102a again decreases and the second couplet component 102a moves into the disc space 20. As the second couplet component 102a enters the disc space 20 the first lobe 106a of second couplet component 102a will contact the first lobe 106a of the first couplet component 102b.

Since the first couplet component 102b and the second couplet component 102a are each on common guide 40, couplet guide passages 116a, 116b align. As illustrated in FIG. 19, in the assembled prosthesis 100, the complementarily configured prosthesis components or modules 102a, 102b axially and radially overlap with one another to form the spherical prosthesis 100.

The inserted guide 40, first couplet component 102b and second couplet component 102a may be fixed together in the disc space 20 by sliding anchor 44 inwardly along the length of guide 40 (shown in FIG. 23C). When anchor 44 comes in contact with second couplet component 102a, guide end cap 42 is drawn snugly against first couplet component 102b by pulling the guide free end 41 away from the couplet prosthesis 100. At the same, time anchor 44 is pushed into anchor receiver 46i. Forcing anchor 44 into anchor receiver 46i causes anchor 44 to plastically deform, biased against the guide 40, fixing anchor 44 in place along the length of guide 40, as shown in FIGS. 14A and 14B, above. Guide 40 is then cut off generally flush with anchor 44 leaving the assembled couplet prosthesis 100 implanted in the disc space 20.

In the illustrated embodiment each of lobes 106 and 108 include spherical surfaces that when mated form a generally spherical device. It is contemplated that lobes 106 and 108 may each include only a portion of a spherical bearing surface with the remaining exterior surface forming at least one alignment projection. The alignment projection is configured to extend beyond the diameter of the spherical surface and periodically engage the endplates to maintain the spherical bearing surface in alignment with the endplate (see FIG. 28). Further, the diameter of the spherical bearing surfaces may be greater than the height of the disc space. In one embodiment, the spherical shape is truncated to reduce the height of the implant to less than the diameter but retain the larger diameter spherical bearing surfaces on the upper and lower surfaces of the device.

Figure 24:
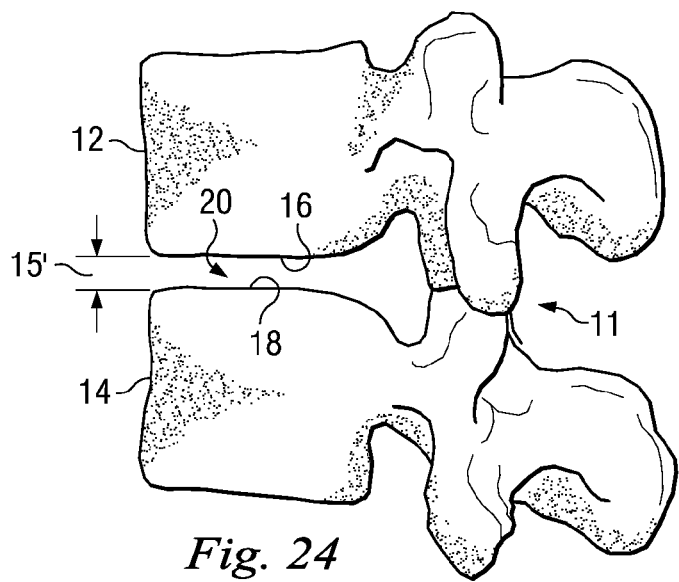
FIG. 24 is a lateral side elevation view of components of a section of a vertebral column with compressed disc space.
Figure 25:
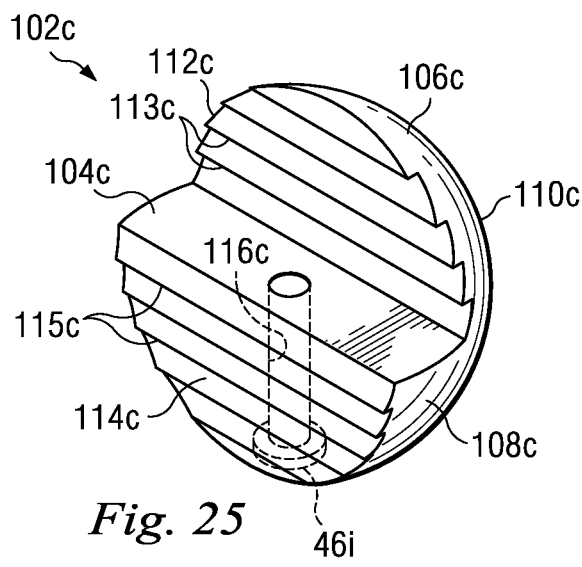
FIGS. 25, 26 and 27A-C illustrate alternative prosthesis module portions of the embodiment and an associated alternate method shown in FIGS. 21, 22 and 23A-C.
Figure 26:
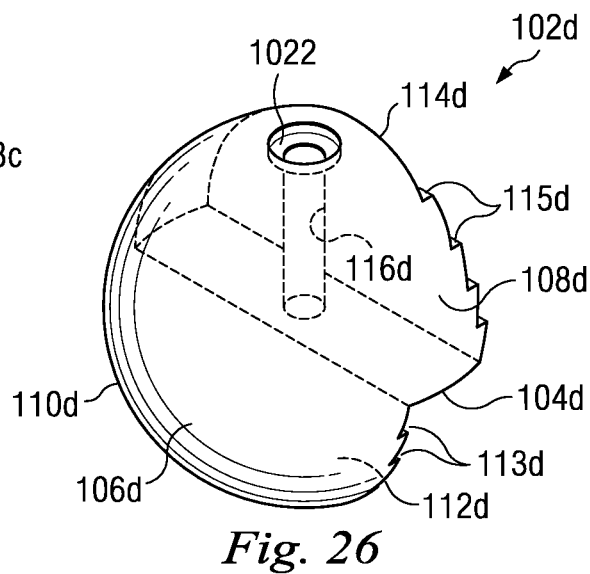

Referring now to FIG. 24, illustrates a vertebral joint section with a reduced disc height 15'. The disc is not shown in order to maintain the simplicity of the drawing, but portions of the disc may exist in the disc space 20. For any of a variety of reasons, the endplates 16, 18, have moved closer together than in a healthy vertebral joint section. The interface between the distal processes on the posterior side of the upper and lower vertebra 12, 14, creates a facet joint 11. In some embodiments, as described below, a prosthesis may be used to distract the joint section to change the height 15' to a desired greater height.

Referring now to FIGS. 25, 26, 27A-C, and 28 an alternate embodiment of the couplet prosthesis 100c, is similar to the embodiment shown in FIGS. 21, 22 and 23A-C, except that the first lobe faces 112c, 112d, and the second lobe faces 114c, 114d, comprise complementary interlocking engagements 113c, 113d, 115c, 115d. Interlocking engagements 113c, 113d, 115c, 115d have a complementary ratchet and pawl shape that provides for unidirectional lateral movement. As such, the couplet components 102c, 102d, when positioned adjacent to each other on a guide 40, bias against each other's interlocking engagements 113c, 113d, 115c, 115d to create a stable prosthesis structure 100c (see FIG. 27C). Securing a guide 40 with an anchor 44 in anchor receiver 46i secures the prosthesis 100c, with the interlocking engagements 113c, 113d, 115c, 115d engaged.

An alternate method of implanting an intervertebral prosthesis within a disc space 20, between an upper vertebra endplate 16 and a lower vertebra endplate 18 may be appreciated with prosthesis 100c. In a vertebral section with a reduced disc height 15' (see FIG. 24), couplet component 102d may be used to increase the disc height 15. A generally posterior approach is shown, where the guide 40 approaches the disc space 20 from the side of the facet joint 11, but the method may be used from any angle. It is also possible to remove a portion of the facet joint to permit a more medial approach. The separating force, to distract the disc space 20, may be asserted by direct force through the component 102d. Additionally, or alternatively, an alternate distraction device may be applied to the vertebral section.

Figure 27A:
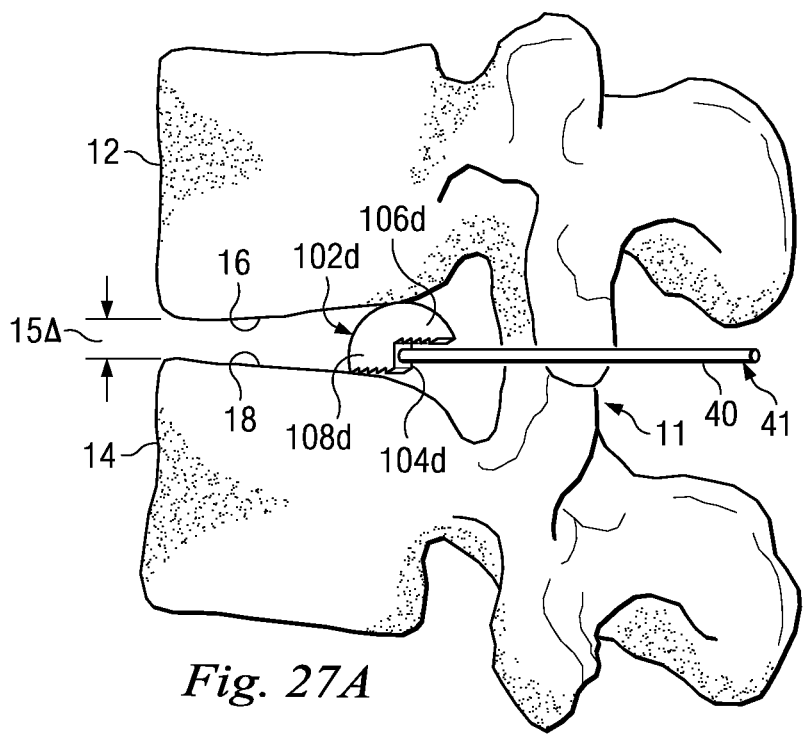
Figure 27B:
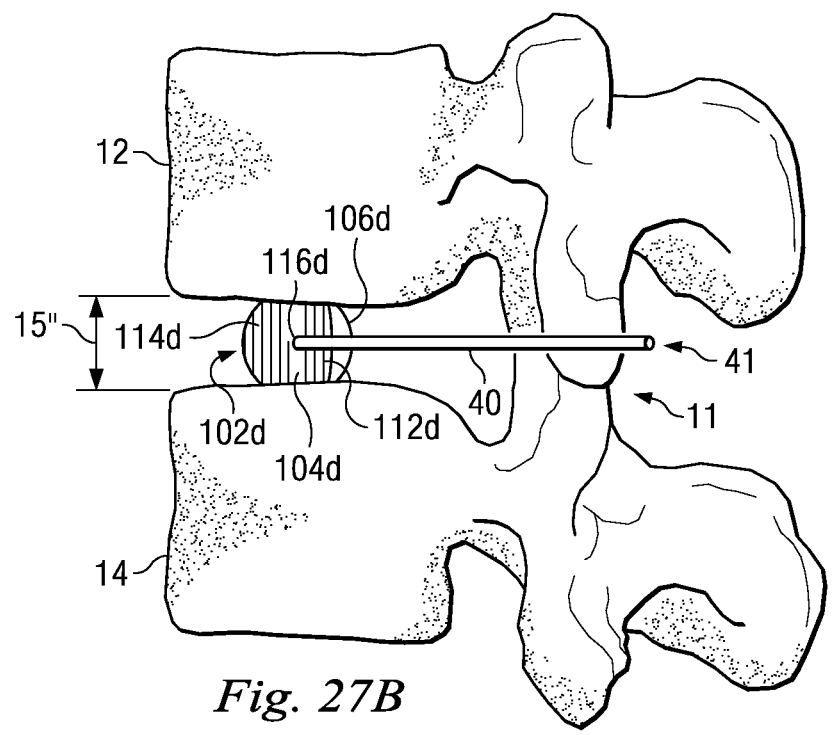
Figure 27C:
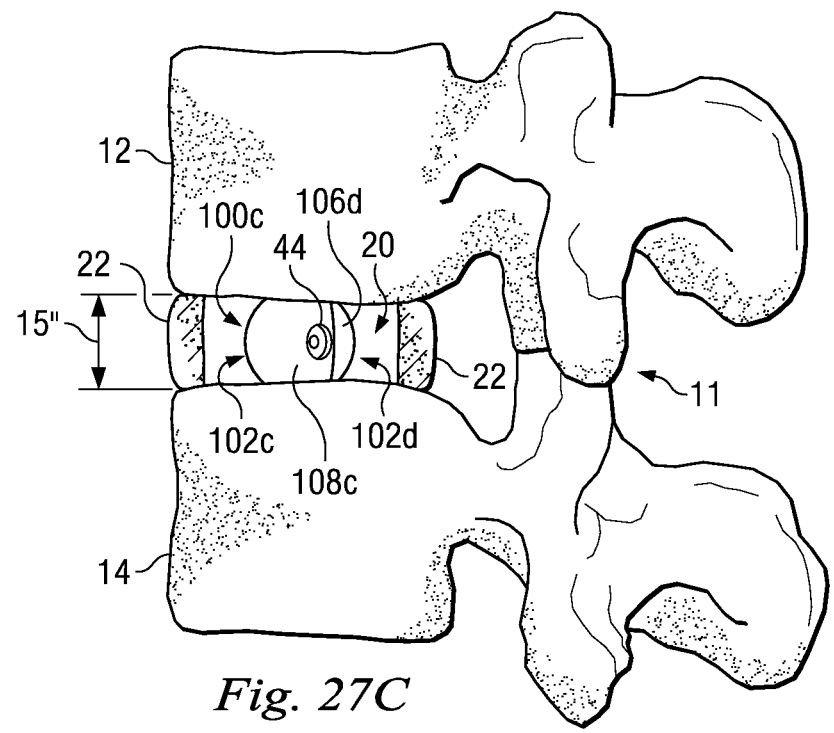

The method includes inserting the component 102d into the disc space 20, leading with second lobe 108d, such that the tapered shape may be used to separate the upper and lower endplates 16, 18, increasing the disc height 15S to at least the thickness of the component 102d, as shown in FIG. 27A. Once the component 102d is in the disc space 20, the disc height 15S can be further increased by rotating the component 102d, so that the crown 110d moves from a cranial-caudal orientation, proximate the upper endplate 16, to a lateral orientation, generally intermediate the upper and lower endplates 16, 18. Here, the rotation direction is about a longitudinal axis defined by the guide 40. So oriented, the diameter of the component 102d is oriented between the upper and lower endplates 16, 18, establishing a further increased the disc height 15", as shown in FIG. 27B. The other component 102c is then inserted into the disc space 20, and the prosthesis 100c is assembled as shown in FIG. 27C. Once secured together, the components 102c, 102d create a stable structure to maintain the increased disc height 15".

Figure 28:
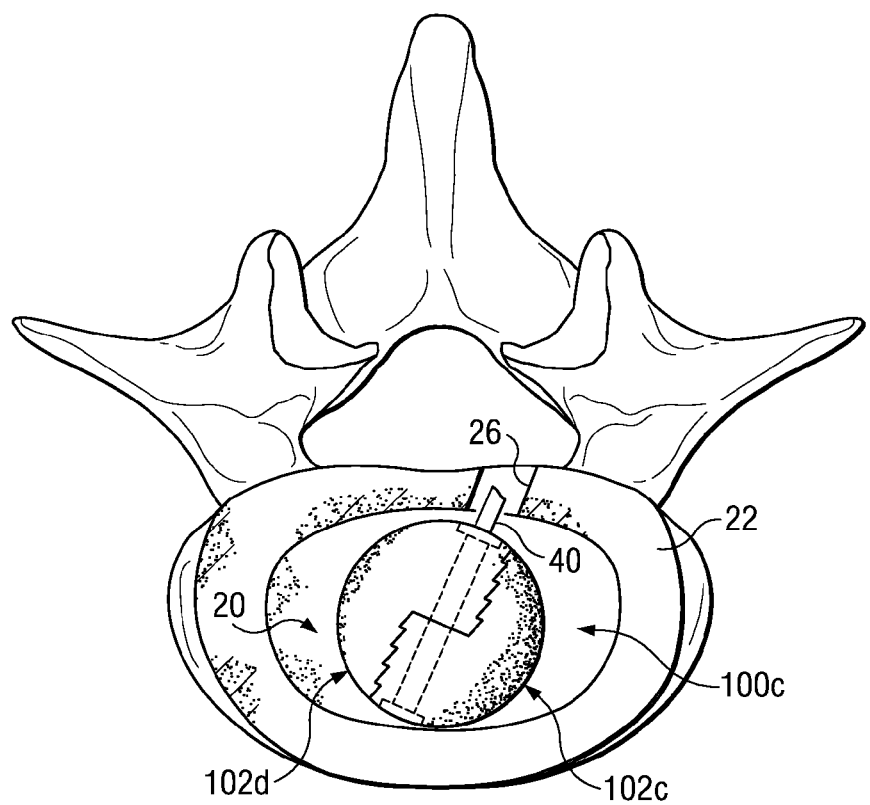
FIG. 28 a top view illustrating an the assembly of FIGS. 25 and 26 in the disc space.

FIG. 28 shows an upper view of the implanted prosthesis 100c within the disc space relative to the lower vertebral body. In this embodiment, because component 102d was used to distract the lower vertebra and upper vertebra to a desired height, both the components 102c, 102d of the prosthesis 100c act as bearing surfaces for the both upper vertebra and for the lower vertebra.

Figure 29:
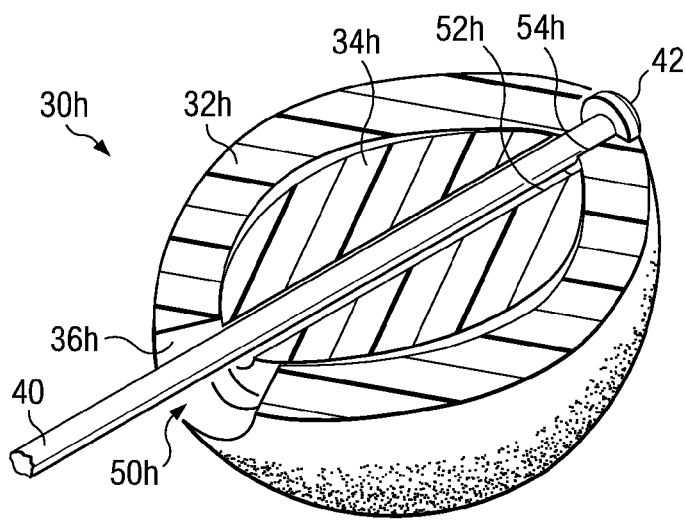
FIG. 29 is a partially cut-away perspective view of an additional alternate embodiment of the FIG. 4 assembly.

Referring now to FIG. 29, in an additional alternate embodiment, prosthesis 30h is generally similar in structure and method of insertion as the prosthesis of FIG. 12, except in prosthesis 30h the inner body 34h and the outer body 32h have a bulge or alignment projection extending outside the spherical diameter to create a generally egg-like shape. Both the inner body 34h and the outer body 32h have a generally spherical shape to their end designed to be nearest the guide end cap 42, but are elongated toward the end designed to be nearest the guide free end 41. Outer body 32h has an outer body opening 36h in the elongated end, and a guide passage 54h in the spherical end. Inner body 34h is similarly shaped, with a guide passage 52h positioned through 34h, such that guide passage 52h and guide passage 54h align to form guide passage 50h, when inner body 34h is positioned within outer body 32h. The elongated end adjacent opening 36h is adapted to engage the endplates to maintain the device orientation in the disc space such that the longitudinal axis of the guide passage 50h is substantially parallel to the generally planar surfaces of the vertebral endplates and generally transverse to the longitudinal axis of the spine. Thus, the guide opening 50h and opposite guide end cap 42 are prevented from bearing against the endplates.

FIGS. 30-33 illustrate an alternative exemplary embodiment of a prosthesis, referenced herein by the numeral 300, embodying principles of the present invention. The prosthesis 300 includes a plurality of portions or modules that include a first component or main body 302 and a second component or wing 304. These components may have complementary sized and shaped interfacing surfaces. Configured for assembly within the disc space, these components may be implanted into a disc space through an access port smaller than the assembled prosthesis 300, allowing minimal sized incisions while providing suitable support and/or articulation.

The main body 302 is shaped substantially as a spheroid, having a bearing surface 306 with an upper portion 308 configured to interface with the upper vertebral endplate and a lower portion 310 configured to interface with the lower vertebral endplate. The main body 302 also includes an instrument receiving port 312 and wing receiving portion 314. In the embodiment shown, the receiving port 312 is a round hole formed in the main body 302. About the port 312, a flat face 316 extends and may interface with an edge of an insertion instrument, as will be explained further below. In the exemplary embodiment shown, the receiving port 312 may include a non-threaded portion 318 and a threaded portion (not shown), with the threaded portion further inside the port.

Figure 32:
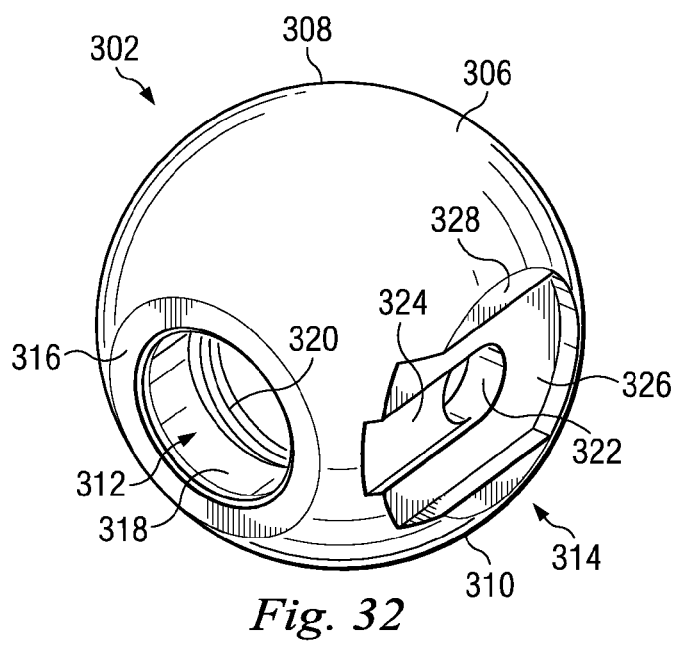

The wing receiving portion 314 may be sized and shaped to receive and secure the wing 304. Although FIG. 32 shows the wing receiving portion 314 on only one side of the main body 302, it is understood that a similar wing receiving portion 314 may be included on a side opposite the one shown. It is contemplated that some embodiments may include two wing receiving portions while other embodiments include only one. In the embodiment shown in FIG. 32, the wing receiving portion 314 is formed of an indentation in the outer surface of the main body 302 and includes a receiving indentation 322, a tab slot 324, a wing slot 326, and a peripheral flat 328.

The receiving indentation 322, in this exemplary embodiment, is formed as a round hole extending centrally into the main body 302. This indentation is shaped to receive a mating peg of the wing 304 (described below) and secure the wing 304 onto the main body. The tab slot 324 aligns with the receiving indentation 322 and guides the peg of the wing 304 to the receiving indentation 322. The wing slot 326 is shaped and sized to receive a portion of the wing and secure it against rotation about the peg of the wing 304. In this embodiment, the receiving indention 322 extends into the main body 302 deeper than the tab slot 324, which extends into the main body deeper than the wing slot 326. The peripheral flat 328 disposed on the periphery of the wing slot 326 permits the wing 304 to fit flush against the main body 302.

It is contemplated that the wing receiving portion may include other alternative features. For example, in some embodiments, the wing receiving portion may be C-shaped and sized to receive and secure a complimentary shaped portion of the wing. In addition, the wing receiving portion may include a single or multiple slots, slits, holes, or other receiving features. In some embodiments, the wing receiving portion is not a depression, but is a protrusion outwardly extending from the main body for engaging a corresponding receiving depression on the wing.

Figure 31:
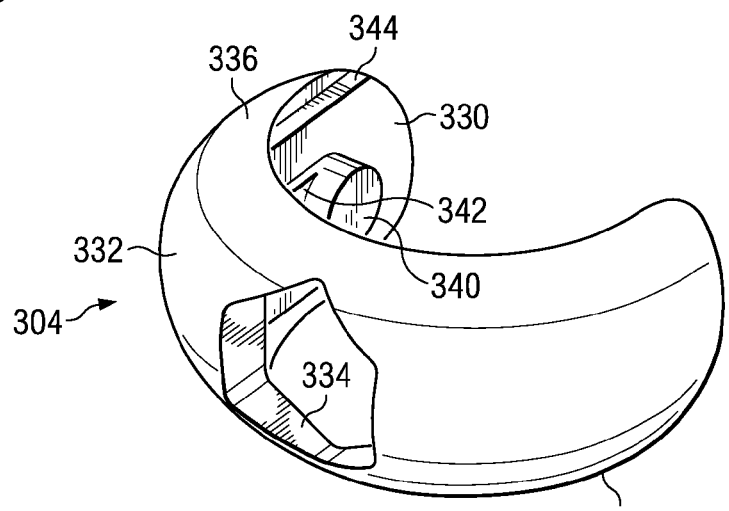
FIGS. 31 and 32 are illustrations of components of the exemplary nucleus replacement device of FIG. 30.

The wing 304, shown best in FIG. 31, is configured to securely attach to the main body 302. It extends at least partially about the spheroid of the main body 302 and prevents excessive rotation of the main body 302 within the disc space. While limited rotation of the prosthesis 300 within the disc space may provide some advantages, contact of the receiving port 312 with the upper or lower vertebral bodies may be undesirable. The wing 304 may prolong the useful life of the prosthesis 300 because it limits rotation of the prosthesis, thereby reducing any likelihood of the upper or lower vertebral bodies bearing on the receiving port 312.

Figure 30:
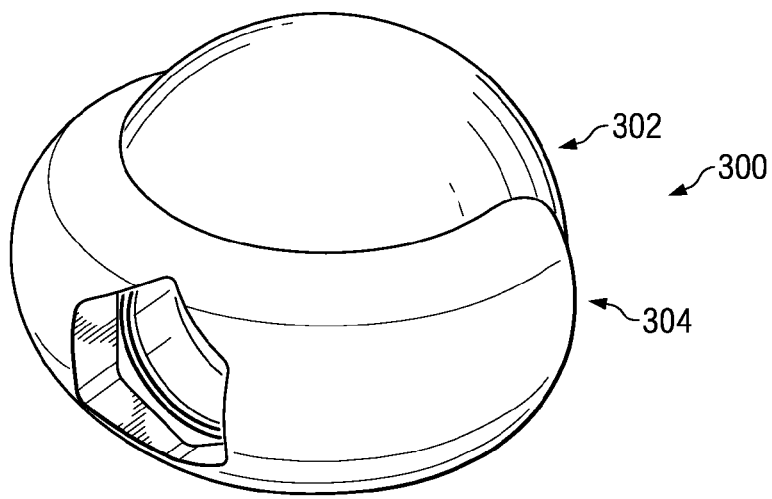
FIG. 30 is an illustration of a perspective view of another exemplary nucleus replacement prosthesis assembly embodying principles of the present invention.

The wing 304 is substantially U-shaped and includes an inner surface 330, an outer surface 332, and an opening 334 extending from the outer to the inner surface. The wing 304 also includes an upper surface 336 and a lower surface 338 configured to contact the vertebral bodies during rotation to limit the rotation of the prosthesis 300 in the disc space. As shown in FIG. 30, the wing 304 has a width greater than the width of the main body 302. Hence, it protrudes outwardly from the main body 302.

The inner surface 330 includes features sized and shaped to mate with the wing receiving portion 314 on the main body 302. Referring to FIG. 31, these features include a peg 340, a tab 342, and a protruding bar element 344. When fully assembled, the peg 340 of the wing 304 fits within the receiving indentation 322 of the main body 302. This inhibits inadvertent removal of the wing 304 from the main body 302. In addition, the tab 342 fits within the tab slot 324 and the bar 344 fits within the wing slot 326. A flush fit between the tab 342 and the tab slot 324 and/or the bar 344 and the wing slot 326 inhibits pivoting of the wing 304 about the peg 340 in the receiving indentation 322. Thus, the wing 304 is secured to cover the receiving port 312 of the main body 302.

In the exemplary embodiment shown, the opening 334 in the wing 304 is non-circular and here is shaped with a hexagonal shape. This allows an associated instrument to rotationally fix the wing 304 with the instrument. Accordingly, the instrument may be used to easily orient the wing 304, and as described below, may allow the instrument to secure the assembled prosthesis against rotation while additional insertion tools are removed. As shown in FIG. 30, in this exemplary embodiment, when in place on the main body, the opening 334 of the wing 304 aligns with the receiving port 312 of the main body 302.

Figure 33:
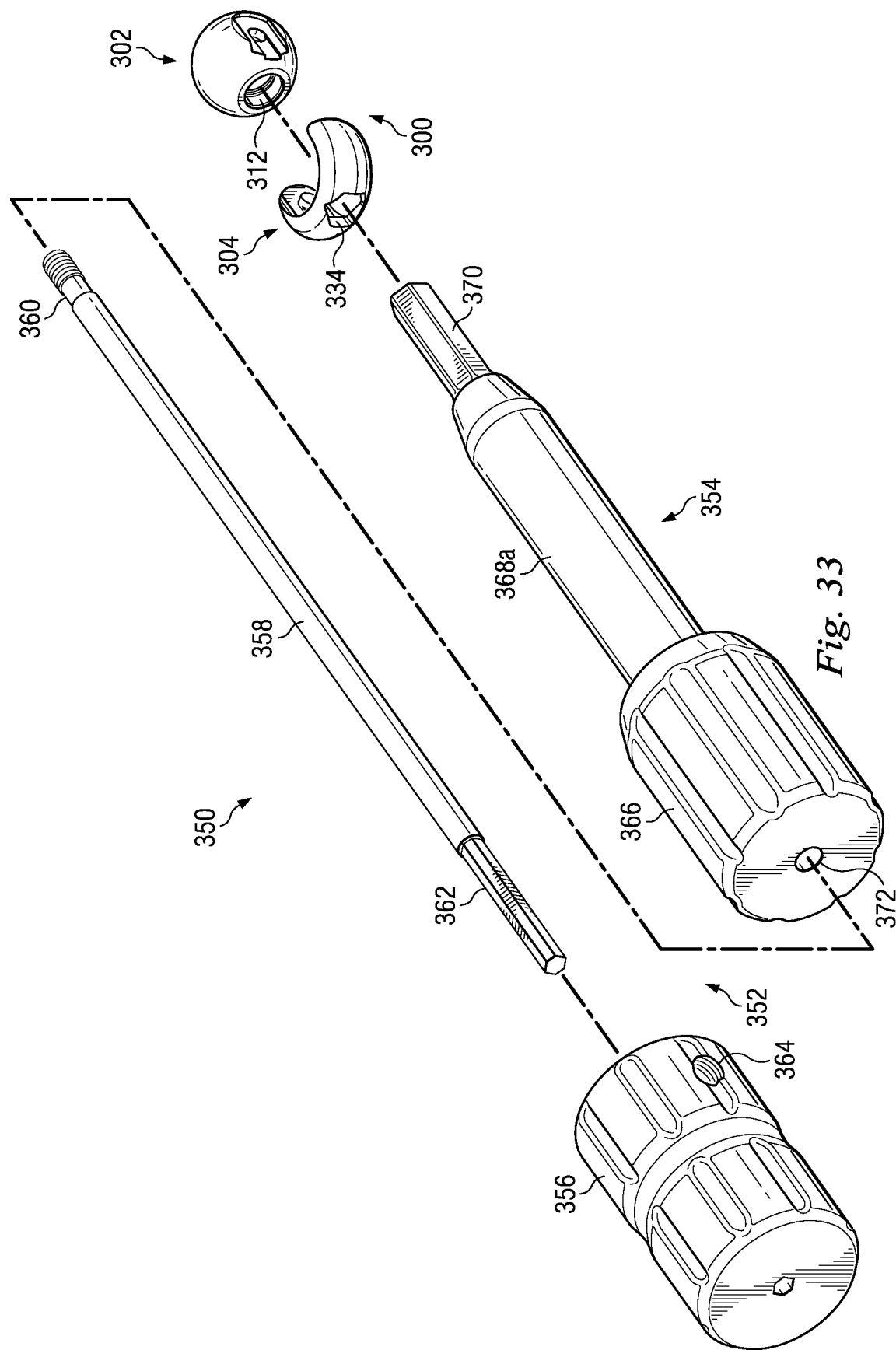
FIG. 33 is an illustration of an insertion tool for inserting the exemplary nucleus replacement device of FIG. 30.

FIGS. 33-36 show the exemplary prosthesis 300 with associated insertion tools and a method of insertion into the vertebral space. Referring first to FIG. 33, the prosthesis 300 is shown as a part of an exemplary implant system 350. The exemplary system 350 includes a body inserter 352 and a wing inserter 354. The body inserter 352 includes a handle portion 356 and a guide or shaft portion 358. The shaft portion 358 includes a threaded end 360 sized to be threaded to the main body 302 and includes a hexagonal end 362 receivable in a receiving hole in the handle portion 356.

The handle portion 356 may be sized and shaped for gripping, twisting, and/or pounding. For example, it may include gripping aids, such as indentations, knurling, or other features, and may include a flat end configured to be pounded with a mallet. In addition, the handle portion 356 may include a shaft securing feature 364 that allows selective securing to the shaft portion 358. In this exemplary embodiment, the shaft securing feature 364 is shown as a hole that may receive a spring plunger that may cooperate with a feature on the handle end (here, the hexagonal end 362) of the shaft portion 358. Other securing features also may be used.

The wing inserter 354 includes a handle portion 366, a shaft portion 368, and a wing mating portion 370. A central lumen 372, sized to receive the shaft portion 358 of the body inserter 352, extends through the wing inserter 354. In this exemplary embodiment, the wing mating portion 370 is a hexagonal shaped portion that is configured to removably fit into the opening 334 on the wing 304.

Figure 34:
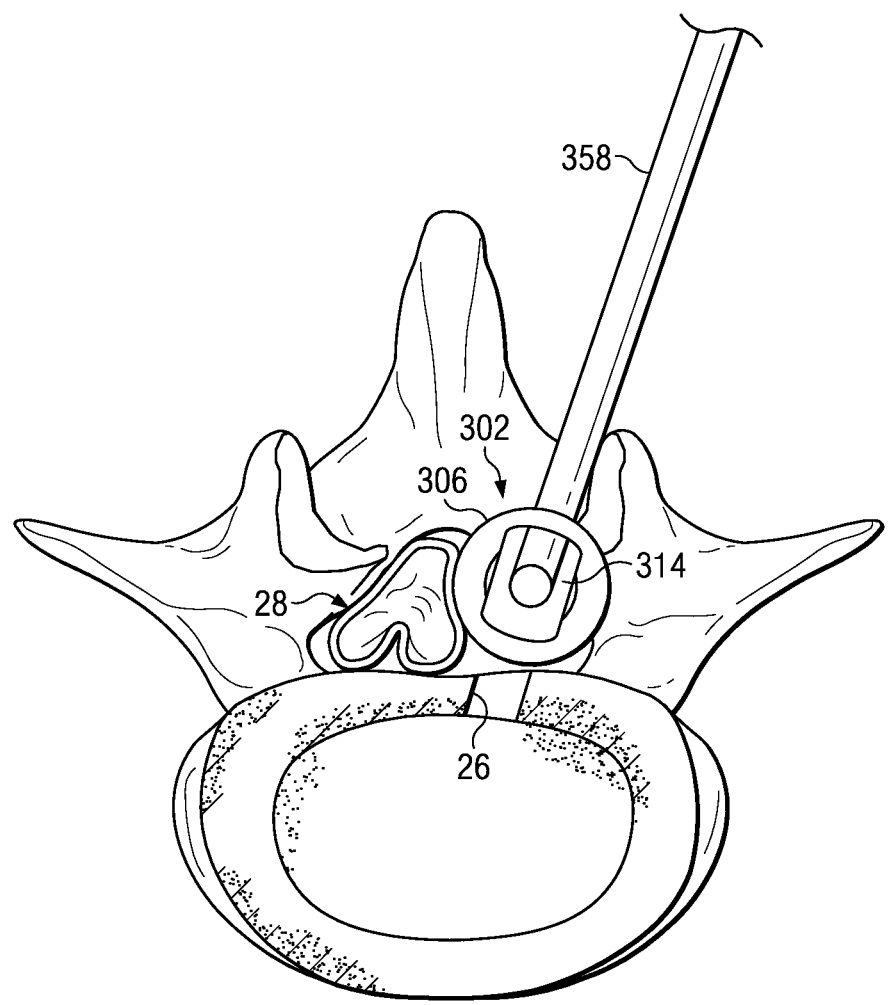
FIGS. 34-36 illustrate an assembly and implantation method of inserting a prosthesis into the disc space.
Figure 35:
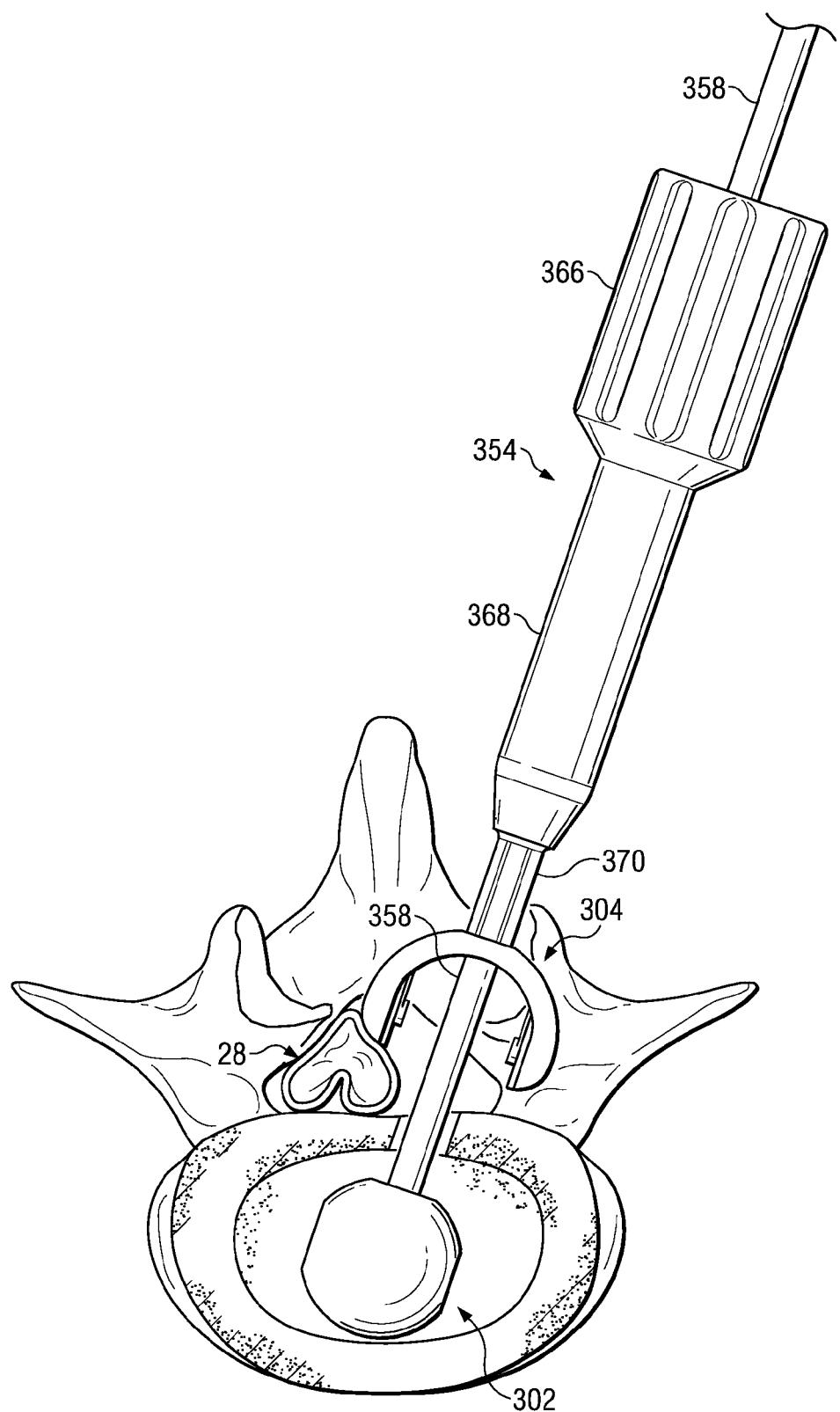

One exemplary method of implanting the prosthesis 300 will be described with reference to FIGS. 34-36. Prior to introducing the main body 302 to the disc space, the shaft portion 358 of the body inserter 352 is threaded into the main body 302. Likewise, the handle portion 356 is attached to the shaft portion 358 and secured using the shaft securing feature 364. Turning to FIG. 34, the main body 302 is introduced to the disc space. In this example, the main body 302 is introduced using a posterior approach, although any other approach also may be used. Further, any of the preparation steps described above with respect to FIGS. 23A-C or other method descriptions also may be performed.

The main body 302 may be moved inwardly toward the disc incision 26. In order to avoid contacting neural structure 28 with edges formed at the wing receiving portion 314, the main body 302 may be rotated a sufficient amount during insertion (for example, 90 degrees as shown) so that only the rounded portion of the bearing surface 306 contacts the neural structure 28, if any contact occurs. During implantation, the disc incision 26 may expand to allow passage of the main body 302. In some embodiments, the handle portion 356 (not shown in FIG. 34) may be contacted with a mallet or hammer to nudge the main body 302 into the disc space. Once in the disc space, the main body may be rotated back so that the upper and lower portions 308, 310 are in contact with the upper and lower vertebral bodies. Then, the handle portion 356 may be removed from the shaft portion 358, leaving the shaft portion 358 connected to the main body 302.

Once the main body 302 is introduced, the wing 304 may be introduced to the disc space. In the embodiment shown, the wing 304 may be attached to the wing inserter 354 by introducing the wing mating portion 370 to the opening 334 in the wing 304. Once attached, the wing 304 and wing inserter 354 may be slid over the shaft portion 358 of the body inserter 352. The wing 304 may be turned or rotated about the shaft portion 358 to advance it past the neural structure 28 and into the disc space. Once there, it may be advanced over the main body 302 so that the peg 340, tab 342, and/or bar 344 on the wing 304 fit into and connect with the receiving portions 314 on the main body 302. In some exemplary embodiments, the wing 304 is at least partially elastically deformable. Accordingly, in these embodiments, the wing 304 may elastically deflect as it is advanced over the main body 302 and then may snap into place. Materials suitable for this may include, among others, polymers such as those in the PAEK family including PEEK, metals, including Ti, CoCr, and SS, and shape memory alloys.

Figure 36:
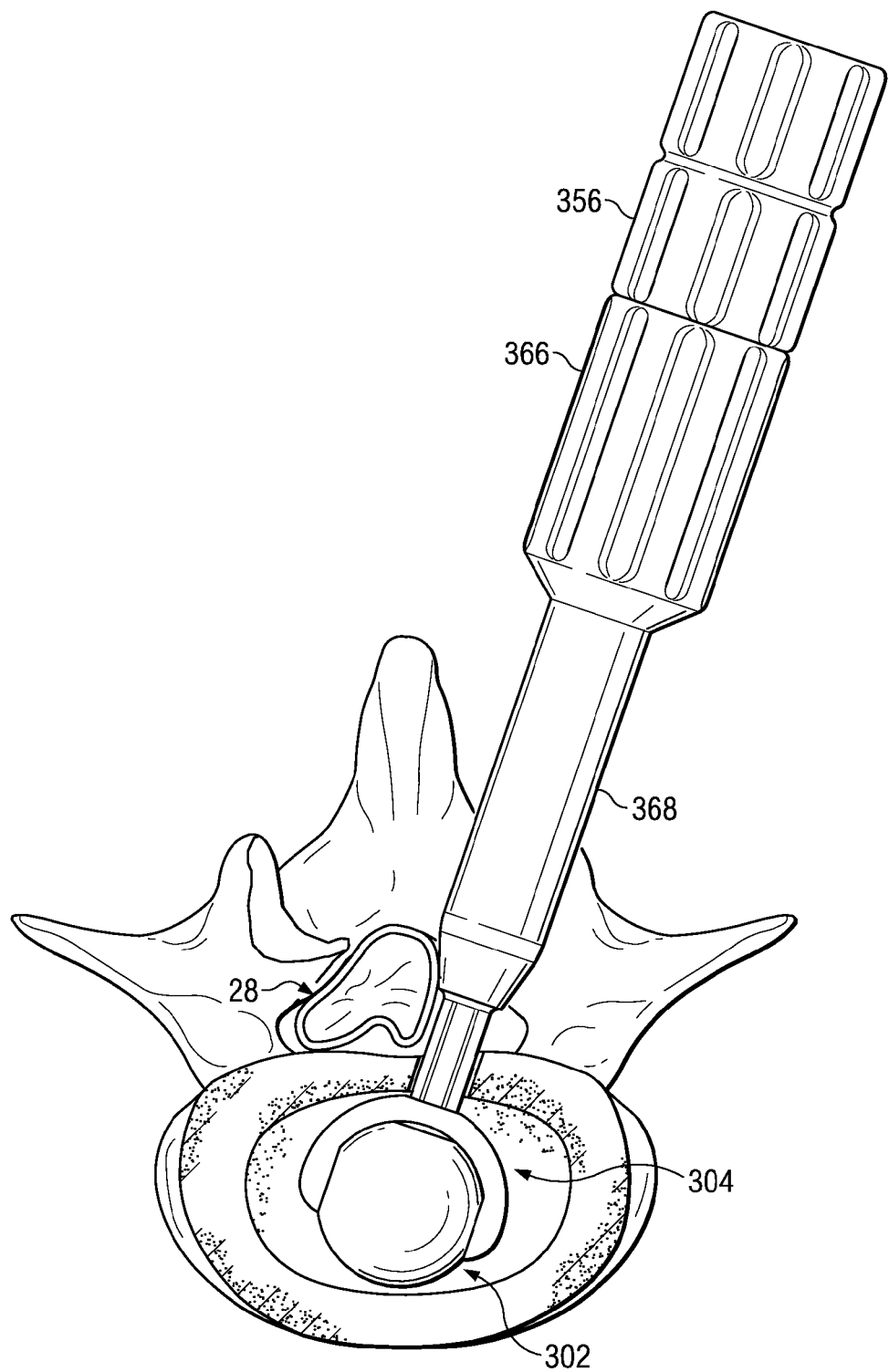
Figure 37:
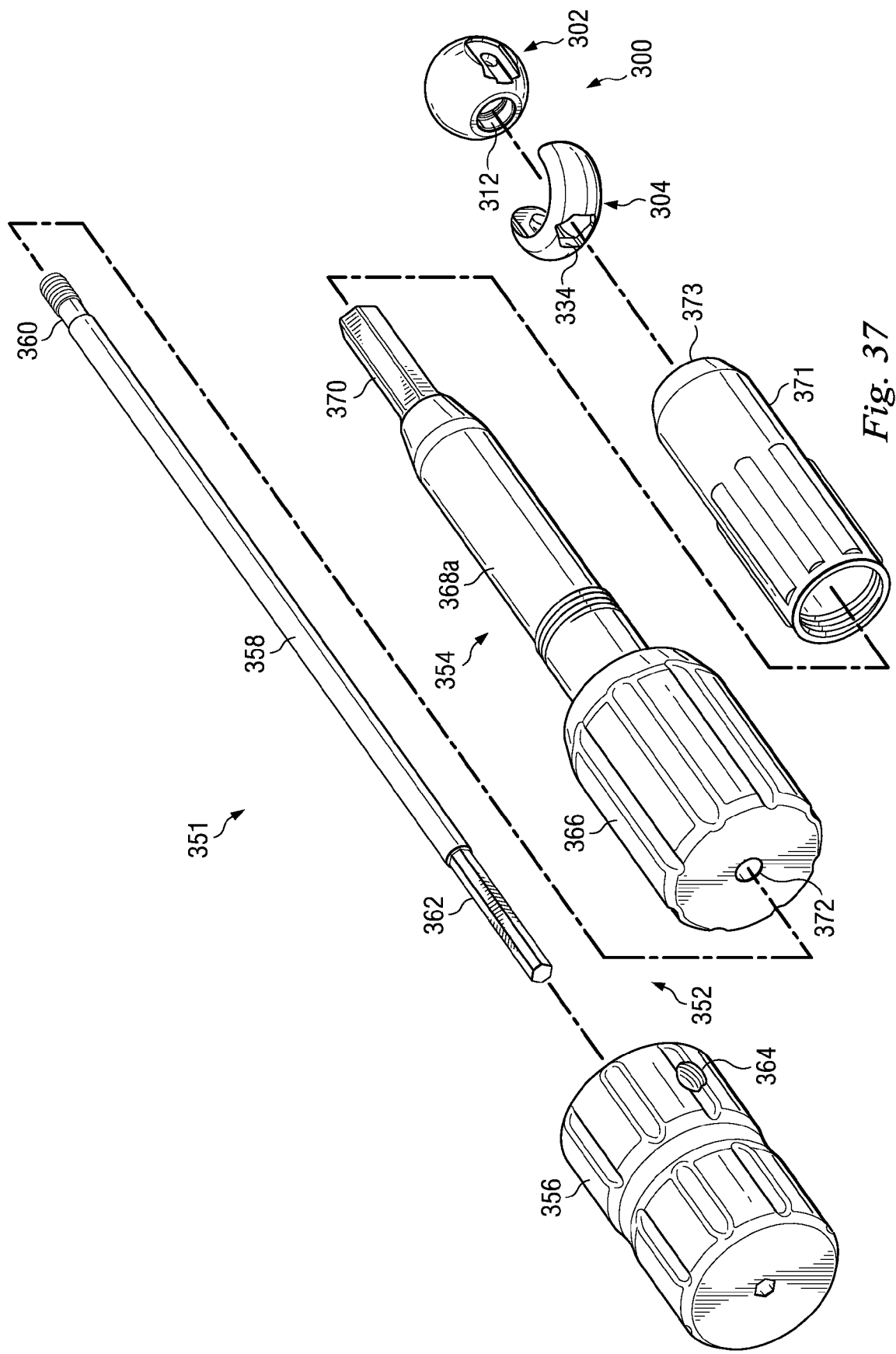
FIGS. 37-39 are illustrations of another exemplary nucleus replacement prosthesis assembly embodying principles of the present invention.
Figure 38:
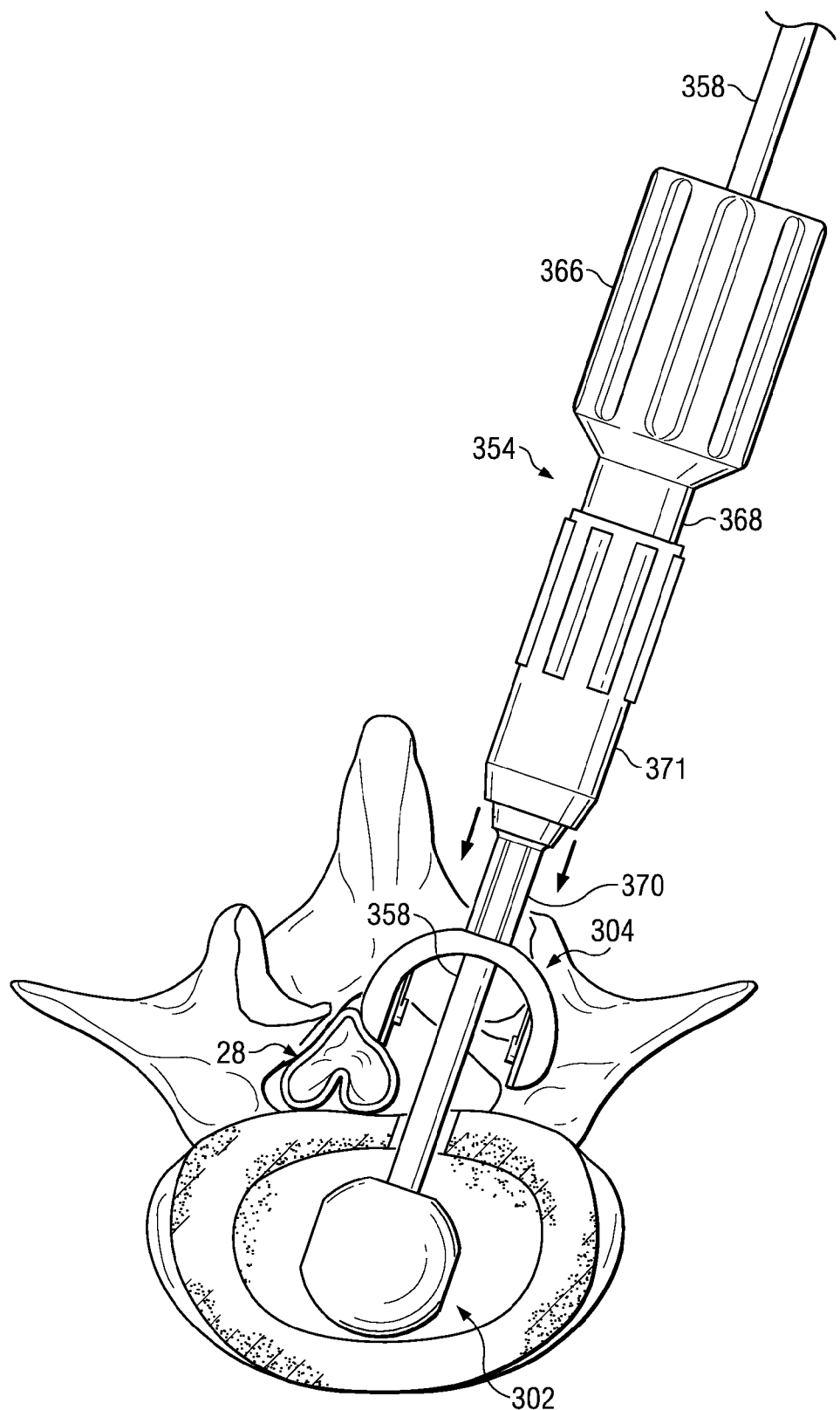
Figure 39:
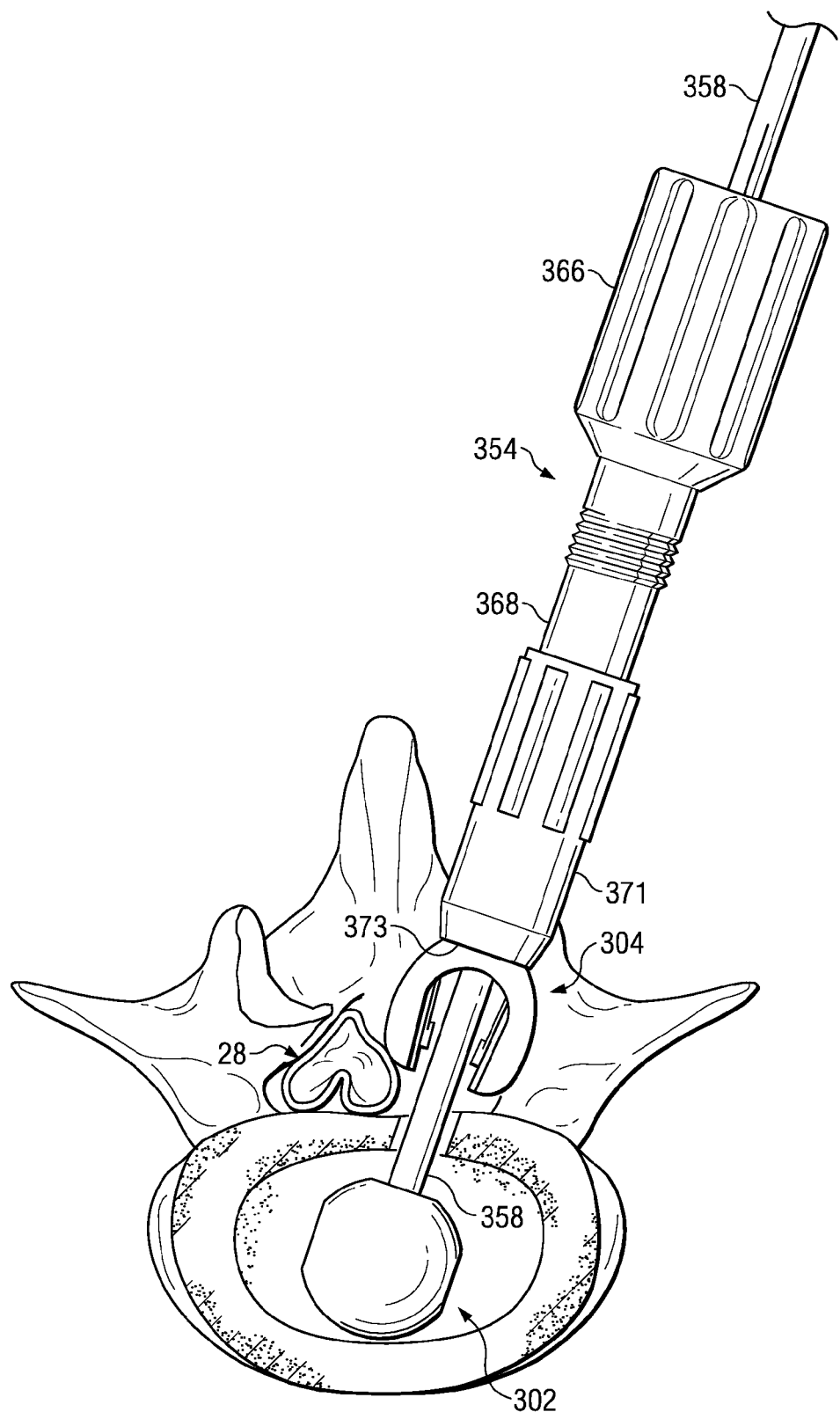
Figure 40:
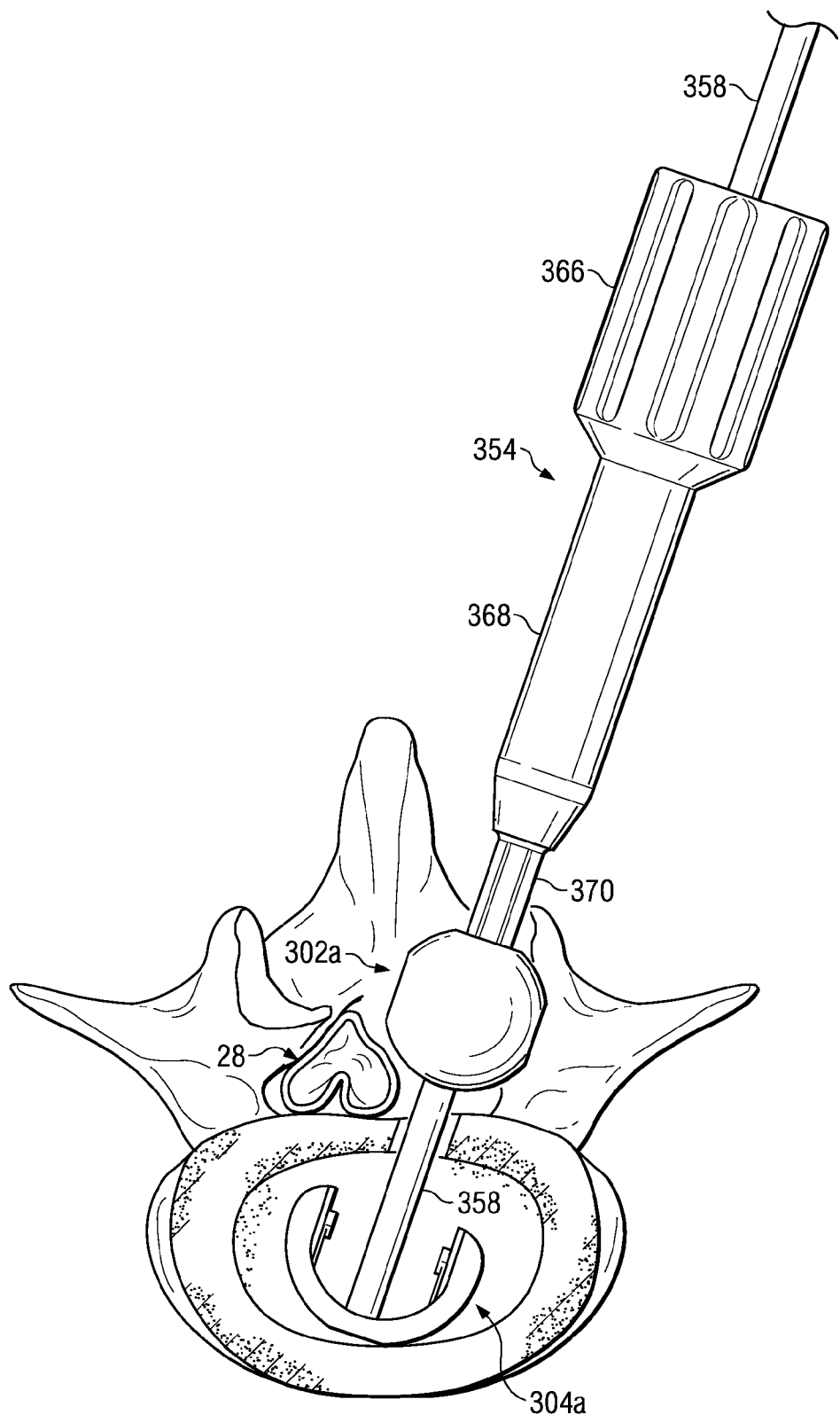
FIGS. 40-42 are illustrations of another exemplary nucleus replacement prosthesis assembly embodying principles of the present invention.
Figure 41:
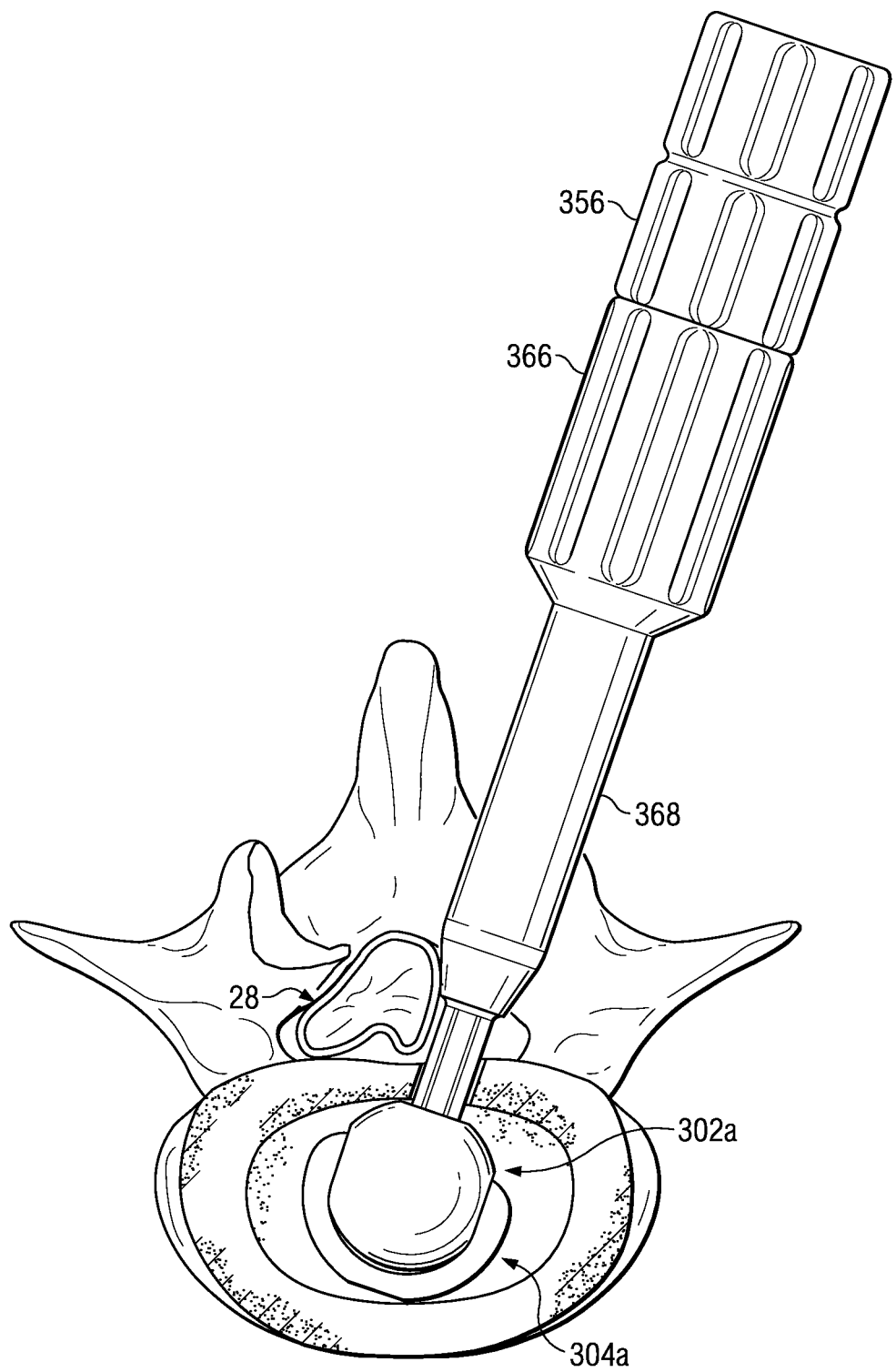

Once the main body 302 and wing 304 are connected within the disc space, as shown in FIG. 36, the insertion instruments may be removed. In some embodiments, the handle portion 356 of the body inserter 352 may be reintroduced onto the shaft portion 358. Once there, the hand portion 356 may be turned to rotate the shaft portion 358 relative to the wing inserter 354. The wing inserter 354 may inhibit turning of the connected wing 304 and main body 302 so that the shaft portion 358 unscrews from the main body 302. Once free of the main body 302, the shaft portion 358 may be removed from the wing inserter 354. The wing inserter 354 also may then be removed from the wing 304 simply by backing it out of the opening 334 and out of the disc space, leaving the combined main body 302 and wing 304 in the disc space.

In one alternative embodiment, the wing and the wing inserter are configured with a break off connection. In some embodiments, the wing is formed integrally with the wing inserter while in other embodiments, the wing and wing inserter are mechanically attached, such as by a cement or adhesive. In one such embodiment, the wing is formed so that once in place, it may break-off from the wing inserter, allowing the inserter to be removed while leaving the wing in place. In some exemplary embodiments, the break-off may be formed by a narrowing of the material at or near the wing and/or may be formed to be relatively brittle at the desired break-off location. Other methods also are contemplated.

In other alternative embodiments, the wing receiving portions formed in the main body may be shaped to secure removal of the wing from the main body or alternatively, may be shaped to inhibit movement about the main body. In one exemplary embodiment, the wing receiving portions are formed as C shaped indentations extending along sides of the main body. The wing may include a portion having a complementary C shape that fits into the C-shape of the main body. This shape allows removal of the wing from the main body in only a single direction, as the C-shaped indentation would secure the wing to, and in some embodiments partially within, the main body. In this embodiment, removal of the body inserter and wing inserter from the main body and wing may be accomplished by rotating the inserter device until the wing contacts the upper and/or lower vertebra. Using the vertebra to stabilize the prosthesis, further rotation of the inserters would unscrew or disengage the main body or wing.

Figure 42:
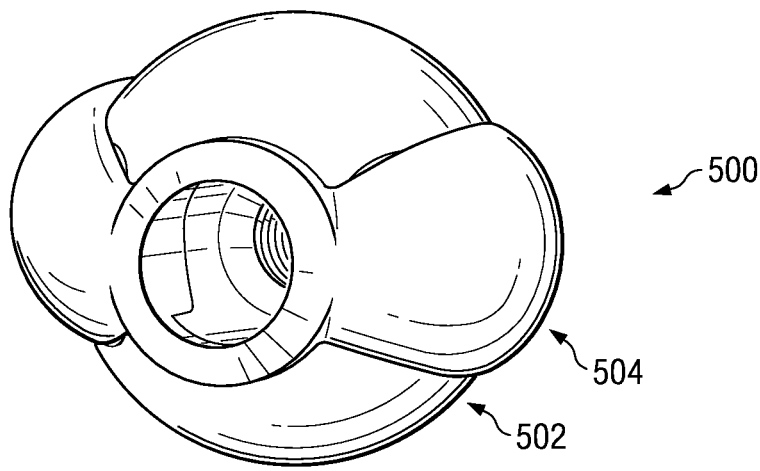
Figure 43:
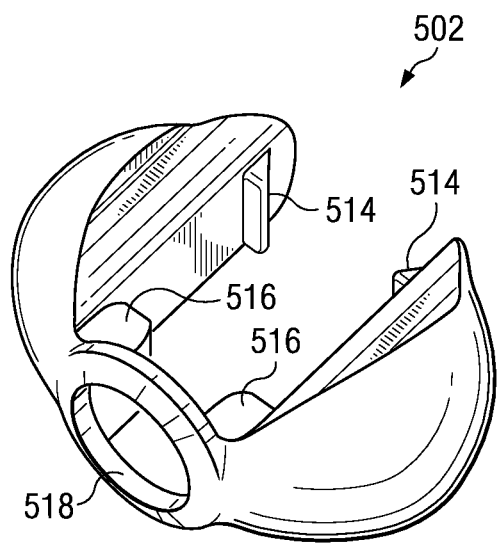
FIGS. 43 and 44 are illustrations of an insertion tool for inserting the exemplary nucleus replacement device of FIGS. 40-42.
Figure 44:
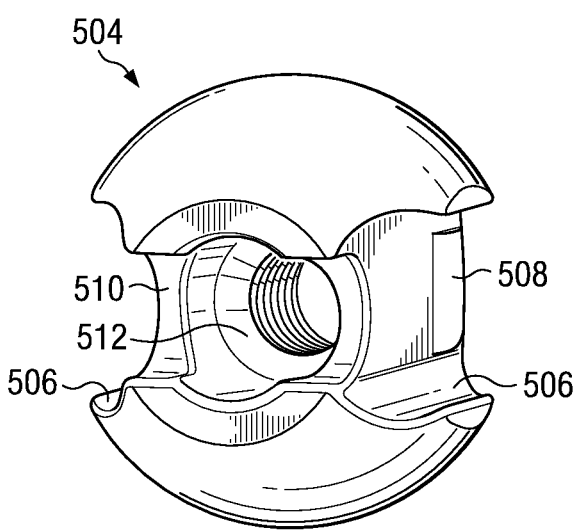

Additional alternative embodiments of intervertebral prostheses are described in FIGS. 37-47. FIGS. 42-44 show an alternative embodiment of an intervertebral prosthesis, referenced herein by the numeral 500. Referring to these figures, the prosthesis 500 includes a main body 502 and a wing 504. As best seen in FIGS. 42-44, the main body 502 includes a wing receiving portion 506 formed on opposing sides as a C-shaped slot having a receiving indentation 508 formed thereon. In addition, the main body includes a front cut-out 510 about an opening 512.

The wing 504 is sized and shaped to advance onto the main body 502 and into the wing receiving portion 506 and into the cut-outs 510. The wings 504 include tabs 514 that are configured to fit within the receiving indentation 508 and includes projections 516 that are configured to fit within the cut-outs 510 to secure the wing 504 to the main body 502. Here, the wing 504 includes a ring-like section 518. Here, the ring-like section 518 reduces the profile and the amount of material for implantation. Accordingly, in this exemplary embodiment, as shown in FIG. 42, the wing protrudes from the main body on two opposing sides, as the ring like section 518 may lie flush with the surface of the main body. In some embodiments, the wing 504 includes an inwardly protruding cylindrical ring that fits within the corresponding body opening 512 in the main body 502.

In other exemplary embodiments, the wing may attach to the main body using a fastening system. For example, a fastener, such as a screw may be inserted through the opening in the wing and thread into the opening in the main body, thereby securing the wing to the main body in cooperation with, or as an alternative to, the tabs and receiving indentions. In some examples, the fastener may include a washer configured to fit about the screw. In some embodiments, the washer may be shaped to fit past the screw threads in one orientation, but not fit past the screw threads in a different orientation. Accordingly, the washer may be assembled onto the screw in advance, and then introduced to the prosthesis with the screw during implantation. In some embodiments the screw shank may be sized with a diameter near the head that allows the washer to rotate freely about the shank when the washer is adjacent the head. In such an embodiment, the screw may include a longitudinal slot along its shank that fits a tab on the washer allowing the washer to be moved along the shank when aligned but that when not aligned, does not allow the washer to be removed from the screw. In some embodiments, the washer may include a non-circular exterior circumference that may be shaped to fit the opening in the wing. In some embodiments, the screw may be configured to break-off the inserter, leaving the screw behind in the prosthesis.

Figure 45:
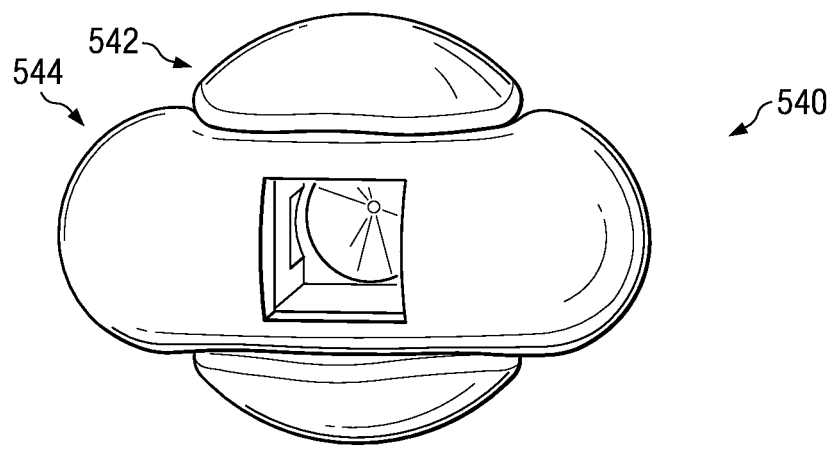
FIGS. 45-47 are illustrations of another exemplary nucleus replacement prosthesis assembly embodying principles of the present invention.
Figure 46:
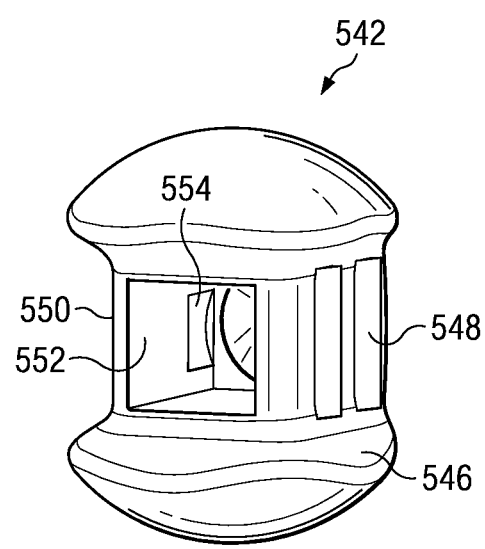
Figure 47:
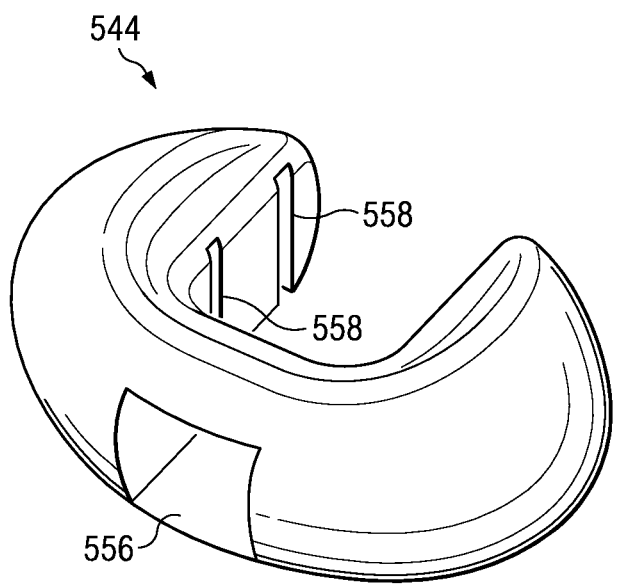

FIGS. 45-47 show yet another exemplary alternative embodiment of an intervertebral prosthesis, referenced herein by the numeral 540. Referring to these figures, the prosthesis 540 includes a main body 542 and a wing 544. As best seen in FIG. 46, the main body 542 includes a wing receiving portion 546, but instead of having a receiving indentation, includes a protruding wing engagement portion 548. In addition, the main body 542 includes a front cutout 550 that together with the wing receiving portions, forms a C-shape about the main body 452. The front cutout includes an opening 552 formed therein. Here, the opening 552 is a square pocket and the main body 502 may be inserted using a square shaped end on an associated insertion tool. Within the opening 552, the opening sidewall includes a cut 554, having for example, a crescent shape, that is shaped and sized to cooperate with an insertion tool, described below. In some embodiments, each surface in the square opening 552 includes a corresponding cut.

The wing 544 is shaped and sized to be generally flush with the spherically shaped outer surface of the main body 542 along the front face, so that the wing 544 protrudes from the main body 542 primarily along the opposing sides. In some embodiments, the wing 544 is configured so that it protrudes on three sides of the main body 542, but protrudes more on opposing sides than on the non-opposing side. Here, the wing 544 includes a square opening 556 and includes receiving indentations 558 sized and shaped to receive the protruding wing engagement portions 548 on the main body 542.

Figure 48:
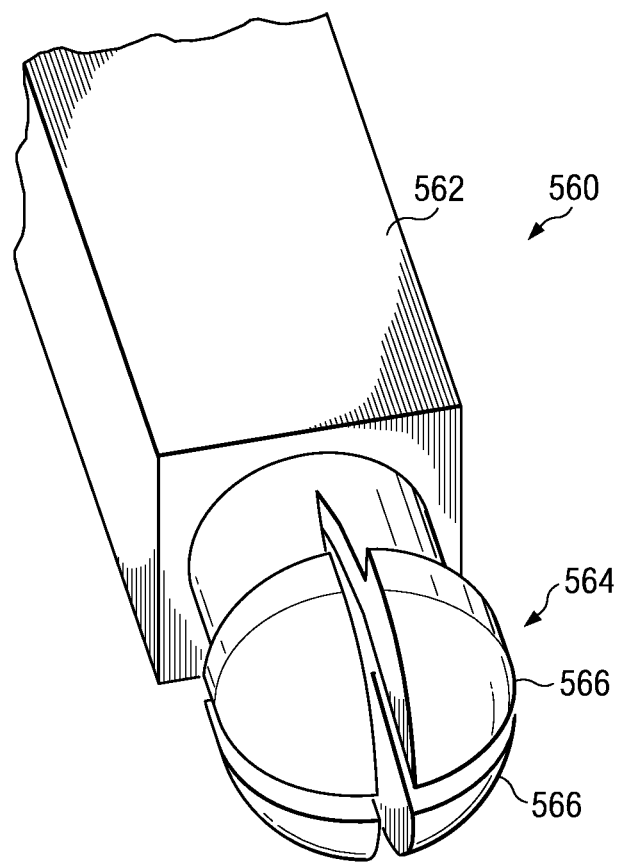
FIGS. 48-51 are illustrations of another exemplary nucleus replacement prosthesis embodying principles of the present invention.
Figure 49:
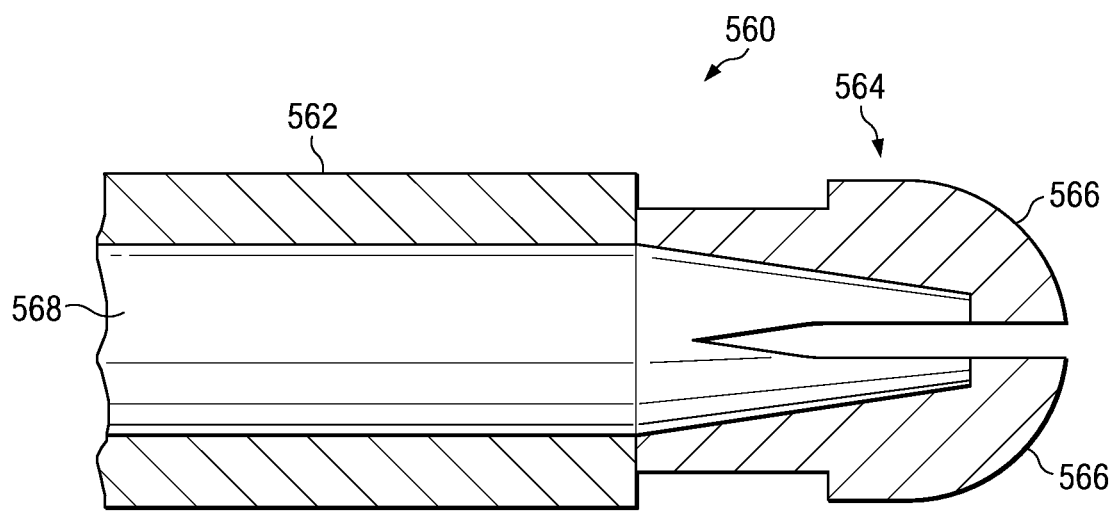

An end of an exemplary insertion tool 560 for implanting the prosthesis 540 is shown in FIGS. 48 and 49. The insertion tool 560 has a profile along a shaft portion 562 that may be sized and shaped for insertion into the openings 552, 556 in the main body 542 and the wing 544. A tip 564 at the end of the shaft portion 562 may be configured to selectively attach to the main body 542. The tip 564 includes splay portions 566 configured to splay outwardly to engage the main body 542.

The insertion tool 560 has a hollow longitudinal lumen 568 that tapers to a smaller diameter as it approaches the tip 564. A rod (not shown) may be advanced through the lumen 568 until it reaches the taper. In some embodiments, the rod has a rounded tip and runs the length of the inserter. Once there, further advancing of the rod acts on the taper to force the splay portions 566 apart, increasing the overall diameter of the tip 564. The splay portions 566 are sized and shaped to project into the crescent cut 554 within the opening 552 in the main body 542, thereby engaging the main body 542 and securing it to the inserter. The square shaft portion 562 shown in FIGS. 48 and 49 engage the square openings 552, 556 of the main body 542 and wing 544 and allow an implanting physician to rotate them in the disc space.

To implant the prosthesis 540, the main body 542 may be first introduced to the disc space on its sides, and then rotated up 90° using the insertion tool 560 to distract the vertebral bodies. The wing 544 may then be introduced to engage the main body 542.

Figure 50:
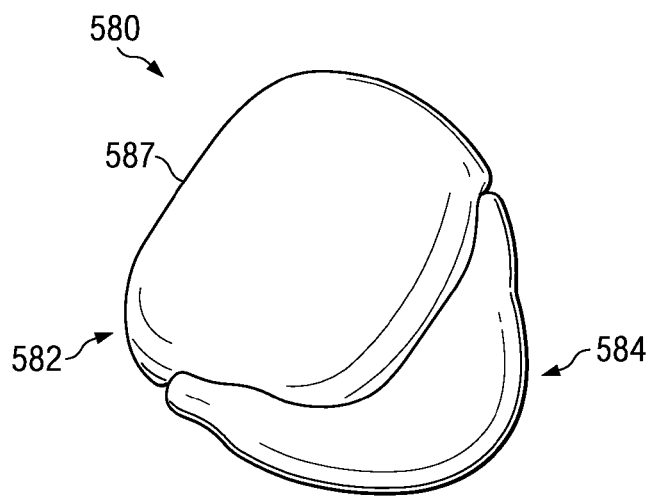
Figure 51:
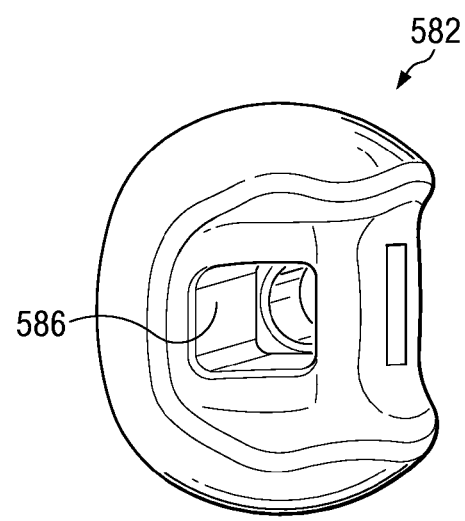
Figure 52:
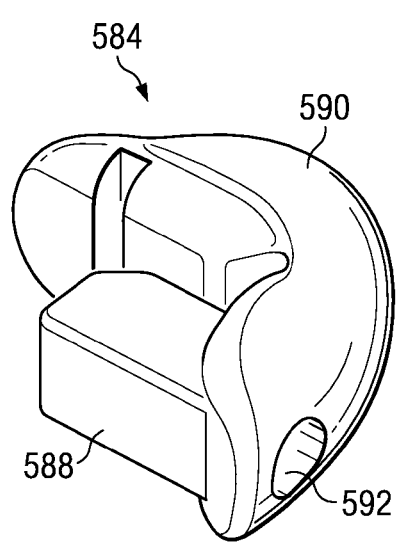
FIGS. 52-55 are sequential illustrations showing an exemplary process of implanting the exemplary prosthesis of FIG. 48 in a disc space.
Figure 53:
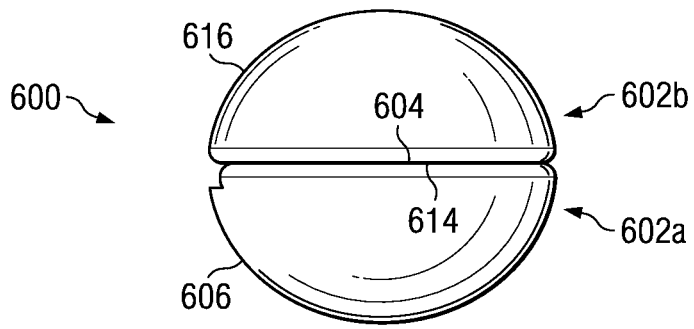
Figure 54:
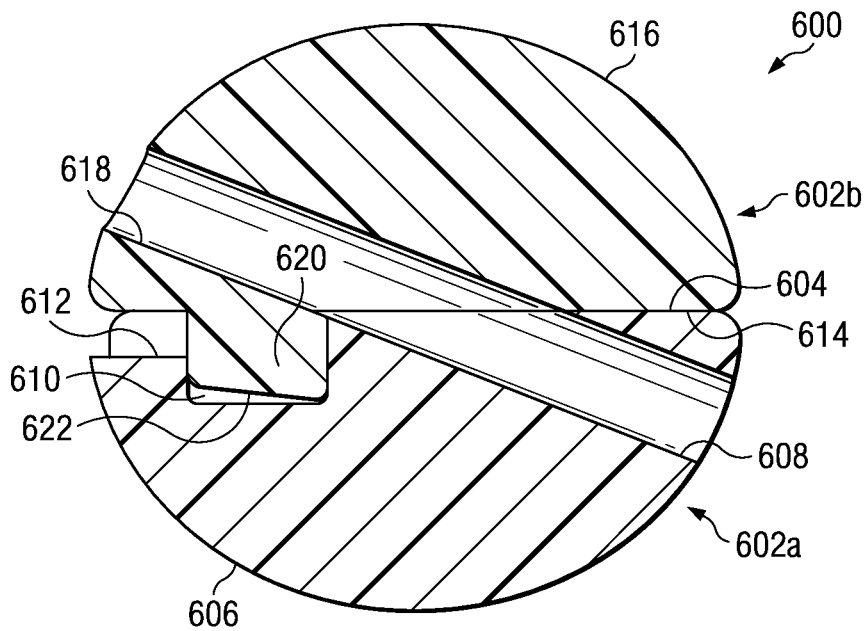
Figure 55:
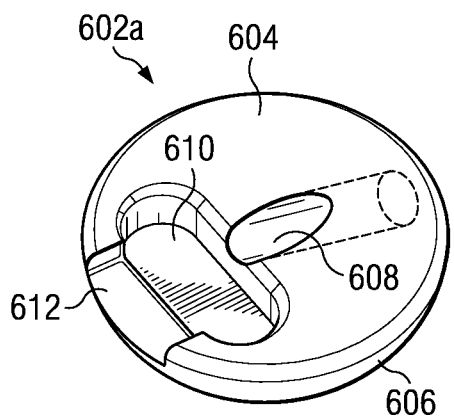
Figure 56:
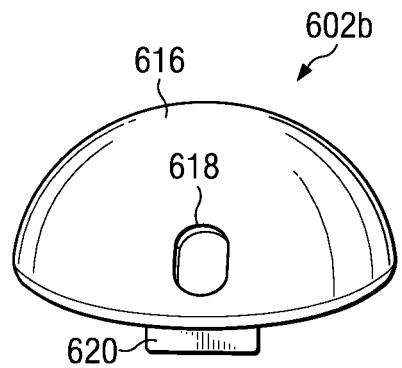
FIGS. 56-58 are illustrations of another exemplary nucleus replacement prosthesis assembly embodying principles of the present invention.

FIGS. 50-52 show yet another exemplary alternative embodiment of an intervertebral prosthesis, referenced herein by the numeral 580. Referring to these figures, the prosthesis 580 includes a main body 582 and a wing 584. As best seen in FIG. 51, the main body 582 includes a wing receiving portion 586 that extends along two adjacent sides. On a side opposing the wing 584, the main body 582 is formed with a flat 587 that helps reduce the insertion profile. In this exemplary embodiment, the prosthesis 580 may be implanted along a guide, as described in some of the exemplary embodiments above. Accordingly, the opening in the main body 582 may be shaped and sized to receive the guide. In addition, the opening 586 in the main body 582 may be shaped and sized to receive a leg portion 588 of the wing 584, thereby securing the wing 584 to the main body 582.

The wing 584 includes the leg portion 588 and an outer body portion 590. In this exemplary embodiment, the leg portion 588 is configured to fit within the opening 586 in the main body 582. An opening 592 in the wing 584 extends through the leg portion and is configured to receive the guide, allowing the wing 584 to be inserted and slid along the guide and aligned to connect with the main body 582.

In this embodiment, the main body 582 may be inserted along the guide and rotated to distract the endplates. The wing 584 may then be inserted and the leg portion 588 may be directed into the opening 586. The leg portion 588 and the receiving indentation on the outer body portion 590 may cooperate to secure the wing 584 to the main body 582.

In some embodiments, the distance between the upper and lower surfaces of the wing is less than the distance between the upper and lower endplates, allowing the vertebral bodies to articulate without simultaneously contacting both the upper and lower surfaces of the wing. In other embodiments, the distance between the upper and lower surfaces of the wing is substantially equivalent to the distance between the upper and lower endplates. In yet other embodiments, the distance is slightly less than the distance between the upper and lower vertebral endplates so that during articulation, the vertebral endplates come into and out of simultaneous contact with the upper and lower surfaces of the wing. Thus, the wing may in some embodiments, cushion or dampen the articulation of the vertebral bodies.

Referring now to FIGS. 53-60, another alternate prosthesis embodiment, referenced herein by the numeral 600 includes multiple components that may be assembled within the disc space 20. These components may have complementary sized and shaped interfacing surfaces. Configured for assembly within the disc space, these components may be implanted into a disc space through an access port smaller than the assembled prosthesis, allowing minimal sized incisions while providing suitable support and/or articulation.

The prosthesis 600 includes a first couplet component 602a and a second couplet component 602b. In this exemplary embodiment, the first and second couplet components are each semi-spherically shaped, but together, do not form a true sphere. Instead, the assembled prosthesis has a width at the interfacing surfaces greater than its height. This may provide a larger surface area in contact with the vertebral endplates. Other embodiments however, include couplet components that form a sphere or other shape or configuration.

The first couplet component 602a includes a couplet interfacing surface 604 and an outer surface 606. The outer surface 606 may be configured to interface directly with the upper or lower vertebral endplates, and may include a bearing surface portion. In this exemplary embodiment, a couplet guide passage 608 extends from the outer surface 606 to the interfacing surface 604. In this exemplary embodiment, the guide passage 608 angles relative to the interfacing surface at an angle within the range of 10-40 degrees, and more particularly, within the range of 25-35 degrees. In other embodiments however, the guide passage 608 angles relative to the interfacing surface 604 at angles outside these ranges, including perpendicular to the interfacing surface 604.

In this exemplary embodiment, the guide passage 608 is formed as a cylindrical bore. Although not shown in the example of FIGS. 53-60, some embodiments of the couplet component 602a include an anchor receiver where the couplet guide passage 608 intersects the outer surface 606. In addition, some embodiments include a guide recess (not shown) formed adjacent the couplet guide passage 608 where the guide passage 616b intersects the outer surface 606. Such a guide recess may be sized to keep a guide wire end from protruding beyond the outer surface 606.

In the exemplary embodiment shown, the couplet 602a includes a pocket 610 formed in the interfacing surface 604 and includes a guide slot 612 formed in the interfacing surface 604 and extending from the outer surface 606 to the pocket 610. The pocket and guide slot aid during implantation and during assembly of the prosthesis 600.

The second couplet component 602b includes an interfacing surface 614 and an outer surface 616. As with the first couplet component 602a, the outer surface 616 may be configured to interface directly with the upper or lower vertebral endplates, and may include a bearing surface portion. A couplet guide passage 618 extends from the outer surface 616 to the interfacing surface 614. The guide passage 618 of the second couplet component 602b may be angled to fall within the same range as the guide passage 608 of the first couplet component 602a. In some embodiments, the guide passages 608, 618 have the same angle. In the exemplary embodiment shown in FIG. 54, the guide passage 618 is formed as a slot, instead of being formed as a cylindrical hole. This may provide additional mobility during implantation along a guide wire. However, in other embodiments, the guide passage 618 is cylindrical. It should be noted that in some embodiments, the guide passages 608, 618 are formed to have a different shape, including for example, triangular, square, oval or other shape.

The second couplet 602b includes a boss 620 extending from the interfacing surface 614. The boss 620 may be sized to fit within the pocket 610 in the first couplet 602a when assembled. In the embodiment shown, the boss 620 is relatively rectangular shaped, and includes a boss surface 622 that is tapered relative to the interfacing surface 614. The tapered boss surface may aid during assembly by minimizing the amount of over-distraction required when fitting the second couplet component 602b to the first couplet component 602a in the disc space. In addition, the boss 620 is sized and shaped to fit and slide along the guide slot 612 to help guide it to the pocket 610. The boss 620 may have any shape, including square, cylindrical, or any others. Further, the boss surface 622 need not be tapered, but may be parallel to the interfacing surface or may include a chamfer or rounded edge.

When assembled, as shown in the cross-sectional view of FIG. 49, the guide passages 608, 618 may align to form a single passage extending through the prosthesis 600. This helps guide the first and second components 602a, 602b during implantation and assembly within the disc space. One example of implantation and assembly is set out below with reference to FIGS. 52-54.

We note that some of the method steps described with respect to previous embodiments, such as FIGS. 23A-C and others, will not be repeated here. Nevertheless, it is understood that any of the method steps of any of the embodiments may be used in any of the methods described with other embodiments. Further, it is contemplated that any of the features of any of the embodiments described herein may be applied to any other of the embodiments.

Figure 57:
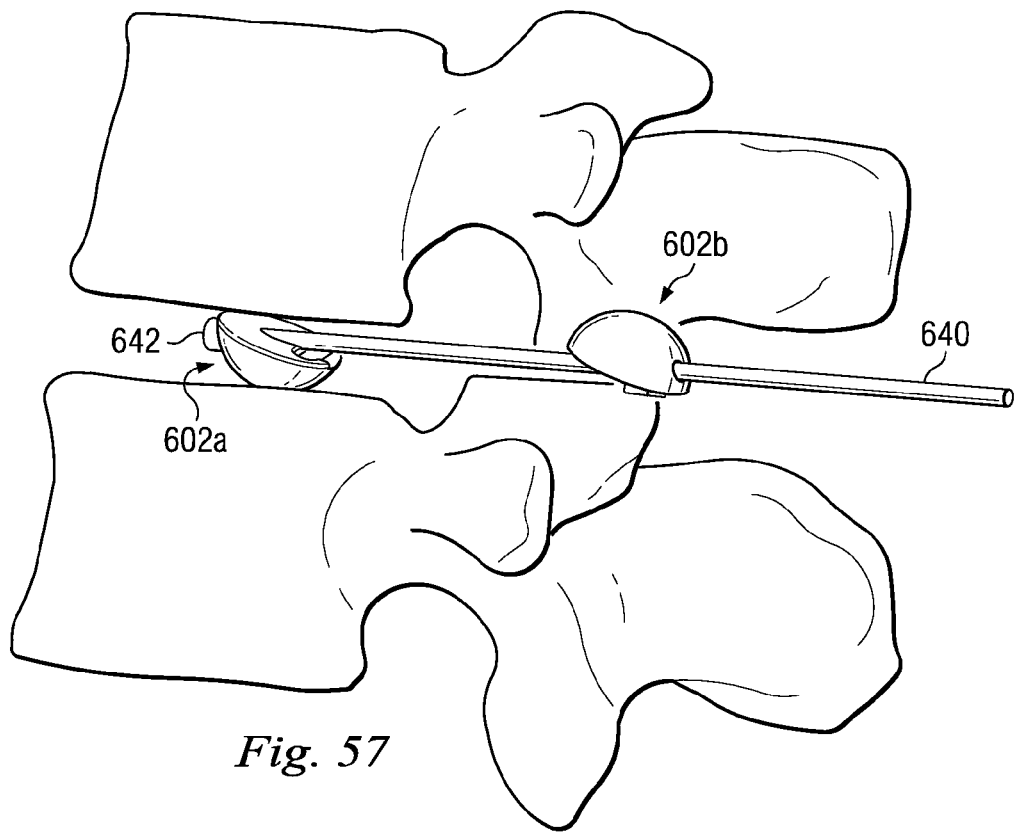

Turning first to FIG. 57, the first couplet component 602a is introduced to the disc space along a guide 640 having a diameter slightly less than that of the guide passages 608, 618. This may include rotating the couplet component 602a so that its outer surface faces any neural structure. As shown and as described previously, the guide 640 includes a guide end cap 642 that is greater in diameter than the guide 640. This guide end cap 642 inhibits the first couplet component 602a from moving off the length of the guide 640.

Figure 58:
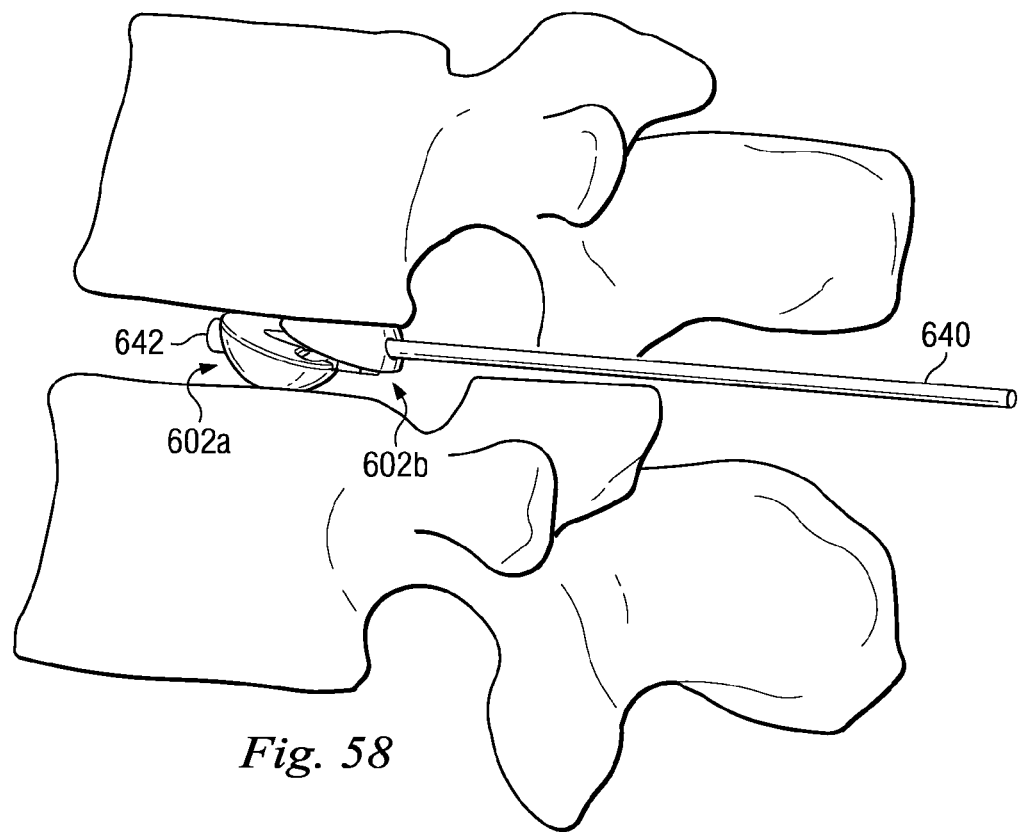
Figure 59:
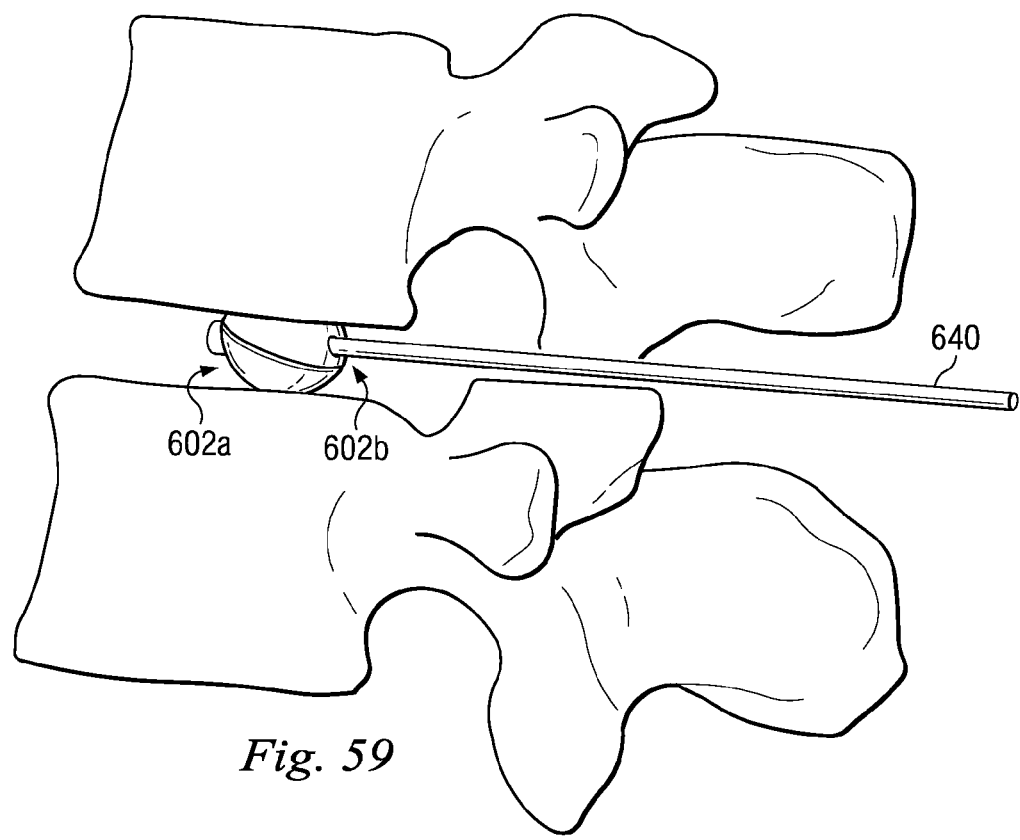
FIGS. 59 and 60 are illustrations of another exemplary nucleus replacement prosthesis assembly embodying principles of the present invention.

After properly introducing the first couplet component 602a to the disc space, the second couplet component 602b may be advanced toward the disc space over the guide 640, as shown in FIGS. 58 and 59. Within the disc space, the second couplet component 602b may be oriented so that its interfacing surface 614 faces the interfacing surface 604. Further advancement may cause distraction of the vertebral bodies as the interfacing surfaces 604, 614 slide against each other. The boss 620 may enter the guide slot 612 and advance toward the pocket 610. The guide passage 618 in the second couplet component 602b, shaped as a slot, may provide some additional clearance for the guide 640, allowing the second couplet component 602b to lie a little more flat as it advances onto the first couplet component 602a. Further, the tapered boss surface 622 and the guide slot 612 also may allow the second couplet component 602b to lie more flat as it advances onto the first couplet component 602b. The guide slot 612 helps orientate the couplet components and reduces the potential of over distraction during implantation and mating.

Figure 60:
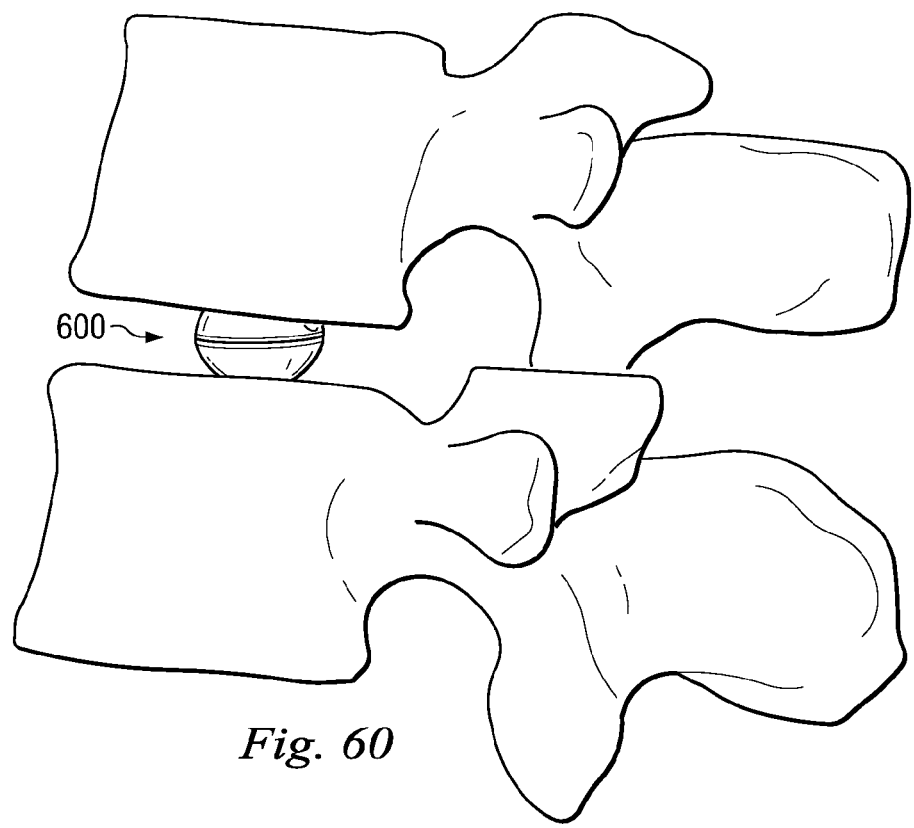

FIG. 59 shows the first and second couplet components 602a, 602b in place together. The couplet components 602a, 602b cooperated to distract the vertebrae a suitable amount. The guide 640 may then be cut-off, snapped off, or removed entirely from the prosthesis 600, leaving the prosthesis 600 intact as shown in FIG. 60.

Other examples of the prosthesis 600 may include a boss shaped as half of a cylinder, lying on its side. A matching capsule-shaped pocket may receive the cylindrical boss. Further, some embodiments do not include the guide slot for guiding the boss.

Figure 61:
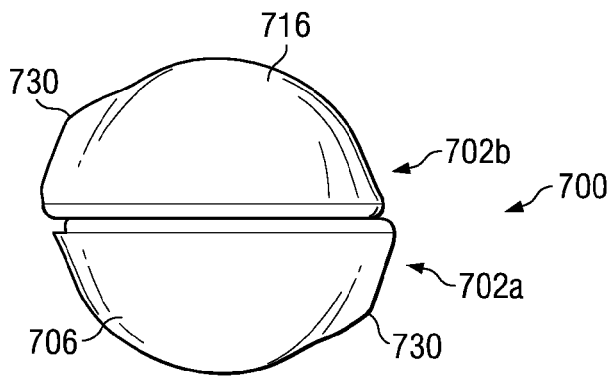
FIG. 61 is a side view of one embodiment of a prosthesis, in accordance with the principles of the present disclosure.
Figure 62:
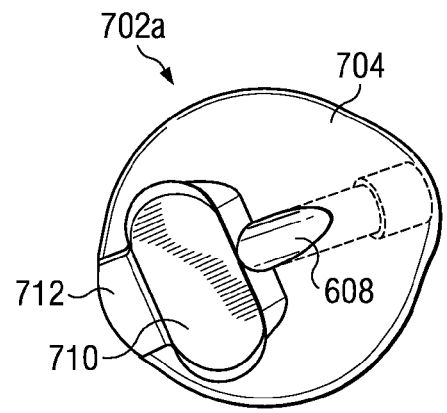
FIG. 62 is a top view of a component of the prosthesis shown in FIG. 61.
Figure 63:
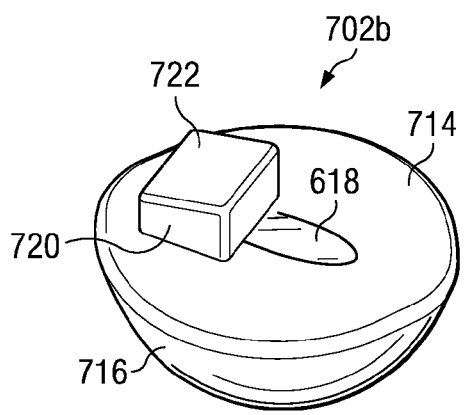
FIG. 63 is a perspective view of a component of the prosthesis shown in FIG. 61.

FIGS. 61-63 show yet another exemplary embodiment of an implantable prostheses, reference herein by the numeral 700. This embodiment includes many of the features of the prosthesis 600 described above. The prosthesis 700 includes first and second couplet components 702a, 702b with respective interfacing surfaces 704, 714, with respective outer surfaces 706, 716, and with respective guide passages 608, 618 (shown in FIGS. 62 and 63). In this embodiment however, the outer surfaces 706, 716 include bumps 730 formed around openings to the guide passages 708, 718. The bumps 730 inhibit the implant from rolling within the disc space to an orientation where the vertebral endplates bear on the openings, which aids in reducing a chance of the openings rubbing on the endplates and causing wear, subsidence, or fusion.

In this exemplary embodiment, the bumps 730 protrude from otherwise spherical shaped outer surfaces 706, 716. However, it is contemplated that the outer surfaces may be shaped other than spherical. As shown in FIGS. 62 and 63, the second couplet component 702b includes a rectangular boss 720 with a slightly angled boss surface 722. The first couplet component 702a includes a pocket 710 to accept the boss 720, and also includes a guide slot 712.

Figure 64:
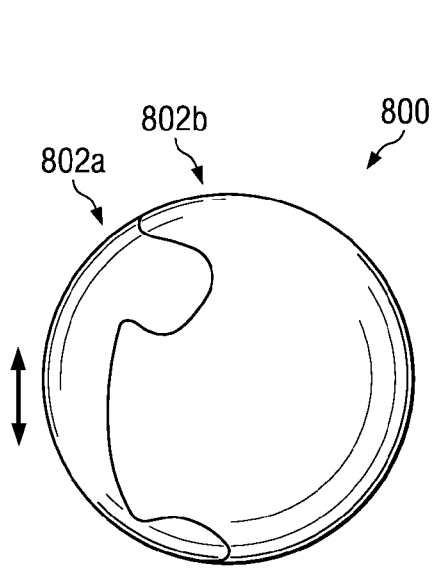
FIG. 64 is a side view of one embodiment of a prosthesis, in accordance with the principles of the present disclosure.
Figure 65:
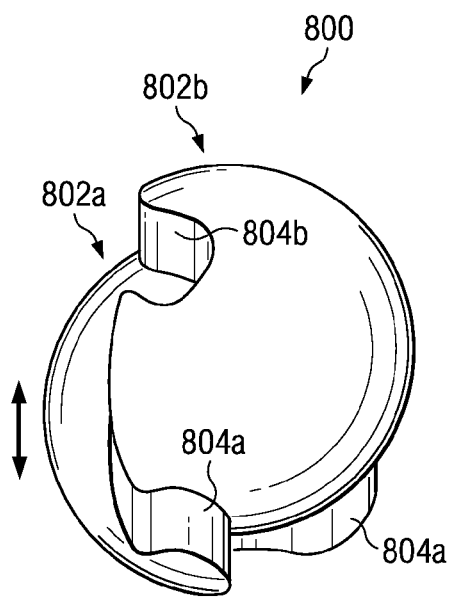
FIG. 65 is a perspective view of a component of the prosthesis shown in FIG. 64.

Yet another exemplary embodiment of a prosthesis is disclosed in FIGS. 64 and 65 and referenced herein by the numeral 800. As described above, this embodiment includes first and second couplet components, referenced herein by the numbers 802a and 802b. FIG. 65 shows couplet components 802a, 802b in a final condition and FIG. 65 shows the couplet components 802a, 802b in an offset condition. In this exemplary embodiment, the couplet components 802a, 802b, include respective lobes 804a, 804b forming an baseball-like design on the outer surface. The lobes 804a of the component 802a cooperate to form a receiving portion that receives a lobe 804b on the component 802b. Accordingly, the components 802a, 802b may slide together and apart as indicated by FIG. 65.

The disclosed devices facilitate a method of implanting an intervertebral prosthesis within a disc space 20, between an upper vertebra endplate 12 and a lower vertebra endplate 14. In an exemplary method, a multi-component prosthesis may be inserted as individual components into the disc space 20 and then assembled, such that the components present an upper load bearing surface and a lower load bearing surface. The upper load-bearing surface is slidably engageable with the upper vertebra endplate 12, and the lower load-bearing surface is slidably engageable with the lower vertebra endplate 14. As such, the prosthesis forms a unitary body that may articulate with the upper and lower vertebra, and reestablish or maintain the disc height 15 of the disc space 20.

In some exemplary prostheses, both the upper and the lower load-bearing surfaces that engage the bone surface of the respective upper and lower vertebral endplate 12, 14 may be present in one component. In other exemplary prostheses, the upper and the lower load-bearing surfaces that engage the bone surface of the respective upper and lower vertebral endplate 12, 14 may be present in multiple components. The load-bearing surfaces may be in multiple components, individual components, or in combination, such as when a load-bearing surface is formed on a boundary between multiple components.

Elements included in this disclosure, and their relationships, may be described in a variety of ways. For example, in some aspects, the present disclosure may be directed to an intervertebral prosthesis apparatus implantable within a disc space, disposed between upper and lower vertebral endplates, via an opening in the annulus extending around the disc space, comprising a plurality of prosthesis modules insertable in a direction through the opening into the disc space. The modules may have at least one set of complementarily-shaped and sized surfaces. The surfaces may be configured to engage within the disc space in a manner that the modules form an assembled prosthesis of a size substantially preventing it from being outwardly expelled from the disc space through the opening. The modules may have bearing surfaces slidably engageable with the endplates to permit articulation between upper and lower vertebral endplates.

The prosthesis, may have individually or in varied combination, that the modules are sequentially insertable; the plurality of modules include a first prosthesis module being laterally compressible for insertion through the opening; that the plurality of modules include a first prosthesis module comprising a material having a relatively low modulus of elasticity, and a second prosthesis module comprising a material having a relatively high modulus of elasticity; that the plurality of modules include a first prosthesis module having a cavity sized to contain a second prosthesis module such that the surface of the cavity complements the shape and size of the exterior surface of the second prosthesis module; that the first prosthesis module has an orifice extending into the cavity, and the orifice is sized to resist passage of the second prosthesis module outwardly therethrough; that the plurality of modules include a third prosthesis module comprising a material having a relatively high modulus of elasticity, the second prosthesis module and the third prosthesis module have a coupling interface, and the guide passage of the first prosthesis module sized to encircle the coupling interface such that the interior surface of the guide passage of the first prosthesis module generally uniformly contacts with the surface of the exterior of the coupling interface; that the coupling interface further comprises a receiver body having a receiver neck, with a receiver well disposed therein, an insert body having an insert shaft, and the insert shaft and the receiver well complementarily sized such that the insert shaft is insertable into the receiver well such that the surface of the insert shaft generally uniformly contacts the surface of the receiver well; that the coupling interface further comprises the insert shaft has an insert slope and a latch, the receiver well has a receiver slope that complements the insert slope, and a strike, and the latch and the strike are complementarily designed to engage upon insertion of the insert shaft into the receiver well, and then to bias against each other to prevent removal of the insert shaft from the receiver well; that the modules are generally similarly shaped and configurable to form a generally spherical prosthesis; that each prosthesis module has a first lobe and a slightly larger second lobe; that the guide passage of each module is contained within its second lobe; that each prosthesis module having an interface surface; and adjacent interface surfaces having complementary interlocking engagements; that the modules are semi-spherical; that the complementarily shaped and sized surfaces comprise interfacing surfaces, and wherein the modules comprise a guide passage extending therethrough, angled relative to the interfacing surfaces; that the guide passages are angled within a range of 10-40 degrees relative to the interfacing surfaces; that a first module of the plurality of modules includes a boss and a second module of the plurality of modules includes a pocket shaped and sized to receive the boss; that includes a guide slot; that a first module of the plurality of modules includes a guide passage and a second module of the plurality of modules includes a guide passage, the guide passages being sized differently; that the second guide passage is formed as a slot; that the first and second guide passages extend from an outer surface to the complementary sized and shaped surfaces; that the module together form a shape oval in cross-section; that a first module of the plurality of modules includes a guide passage forming an opening at a spherical outer surface portion and extending inwardly from the outer surface portion, and a second module of the plurality of modules includes a guide passage forming an opening at the outer surface portion and extending inwardly from the outer surface, the outer surfaces being formed to have bumps protruding from the spherical outer surface portions; that a first module of the plurality of modules includes first lobes and a second module of the plurality of modules includes a second lobe, the second lobe being receivable between the first lobes; that the plurality of prosthesis modules includes a main body having an outer surface including a bearing surface configured to interface with the upper and lower vertebral endplates; and a wing portion attachable to the main body and configured to limit rotation of the main body relative to the upper and lower vertebrae to a range of motion; that the main body includes a receiving indentation configured to receive a portion of the wing portion to attach the main body and the wing portion; that the receiving indentation comprises a C-shape configured to receive a portion of the wing portion; that the wing comprises a ring-like section configured to fit flush against the main body; that the wing portion includes an opening extending therethrough for receiving a guide, and wherein the main body includes an opening formed therein for receiving the guide; that comprises an attachment mechanism for attaching the wing to the main body, the attachment mechanism extending through the opening in the wing portion; that the opening in the wing portion is square shaped; that the wing extends about two sides of the main body.

In some aspects, the present disclosure may be directed to an intervertebral prosthesis apparatus implantable within a disc space between two vertebra endplates, comprising a plurality of prosthesis modules each having a guide passage extending therethrough along an axis. The modules may be configured to be assembled within the disc space, to form the prosthesis, in a nested relationship in which the guide passages are coaxially aligned with one another.

In other aspects the modules are sequentially insertable into the disc space; the plurality of modules include a first prosthesis module being laterally compressible for insertion into the disc space; the plurality of modules include a first prosthesis module comprising a material having a relatively low modulus of elasticity, and a second prosthesis module comprising a material having a relatively high modulus of elasticity; the plurality of modules include a first prosthesis module having a cavity sized to contain a second prosthesis module such that the surface of the cavity generally uniformly contact the surface of the second prosthesis module upon being nested within the cavity; the first prosthesis module has an orifice extending into the cavity; and the orifice is sized to resist passage of the second prosthesis module outwardly therethrough; the plurality of modules include a third prosthesis module comprising a material having a relatively high modulus of elasticity; the second prosthesis module and the third prosthesis module have a coupling interface; and the guide passage of the first prosthesis module sized to encircle the coupling interface such that the interior surface of the guide passage of the first prosthesis module generally uniformly contacts with the surface of the exterior of the coupling interface; the coupling interface further comprises a receiver body having a receiver neck, with a receiver well disposed therein; an insert body having an insert shaft; and the insert shaft and the receiver well complementarily shaped and sized such that the insert shaft is insertable into the receiver well such that the surface of the insert shaft generally uniformly contacts the surface of the receiver well; the coupling interface further comprises the insert shaft has an insert slope and a latch; the receiver well has a receiver slope that complements the insert slope, and a strike; and the latch and the strike are complementarily designed to engage upon insertion of the insert shaft into the receiver well, and then to bias against each other to prevent removal of the insert shaft from the receiver well; the modules are generally similarly shaped and configurable to form a generally spherical prosthesis; each prosthesis module has a first lobe and a slightly larger second lobe; the guide passage of each module is contained within its second lobe; each prosthesis module having an interface surface; and adjacent interface surfaces having complementary interlocking engagements.

In some aspects, the present disclosure may be directed to a system for implantation of an intervertebral prosthesis within a disc space, between a first vertebra endplate and a second vertebra endplate, via an opening in the annulus extending around the disc space, comprising a plurality of prosthesis modules insertable in a direction through the opening into the disc space. The modules may have at least one set of complementarily-shaped and sized surfaces. The modules may be configured to engage at least one set of complementarily-shaped and sized surfaces within the disc space to form an assembled prosthesis of a size substantially preventing it from being outwardly expelled from the disc space through the opening. The modules may have bearing surfaces slidably engageable with the endplates; and an elongated guide for inserting the modules into the disc space.

In some aspects, the modules are sequentially insertable; the plurality of modules include a first prosthesis module being laterally compressible for insertion through the opening; the plurality of modules include a first prosthesis module comprising a material having a relatively low modulus of elasticity; and a second prosthesis module comprising a material having a relatively high modulus of elasticity; the plurality of modules include a first prosthesis module having a cavity sized to contain a second prosthesis module such that the surface of the cavity complements the shape and size of the exterior surface of the second prosthesis module; the first prosthesis module has an orifice extending into the cavity; and the orifice is sized to resist passage of the second prosthesis module outwardly therethrough; the plurality of modules include a third prosthesis module comprising a material having a relatively high modulus of elasticity; the second prosthesis module and the third prosthesis module have a coupling interface; and the guide passage of the first prosthesis module sized to encircle the coupling interface such that the interior surface of the guide passage of the first prosthesis module generally uniformly contacts with the surface of the exterior of the coupling interface; the coupling interface further comprises a receiver body having a receiver neck, with a receiver well disposed therein; an insert body having an insert shaft; and the insert shaft and the receiver well complementarily sized such that the insert shaft is insertable into the receiver well such that the surface of the insert shaft generally uniformly contacts the surface of the receiver well; the coupling interface further comprises the insert shaft has an insert slope and a latch; the receiver well has a receiver slope that complements the insert slope, and a strike; and the latch and the strike are complementarily designed to engage upon insertion of the insert shaft into the receiver well, and then to bias against each other to prevent removal of the insert shaft from the receiver well; the modules are generally similarly shaped and configurable to form a generally spherical prosthesis; each prosthesis module has a first lobe and a slightly larger second lobe; the guide passage of each module is contained within its second lobe; each prosthesis module having an interface surface; and adjacent interface surfaces having complementary interlocking engagements; guide passages through the modules; and the guide insertable into the guide passages; the guide is rigid; the guide is flexible; a guide anchor for securing the guide to the prosthesis; the guide anchor is plastically deformable to bias against the guide; the guide anchor threadedly engages a threaded section of the guide; the interface between the guide and the guide anchor comprises a ratchet and pawl configuration; the guide is secured to a first prosthesis module; the guide is threadedly secured to the guide passage of the first prosthesis module; the guide is integrally formed with the material of the first prosthesis module; the elongated guide has a frangible point and a removable part; the frangible point is constructed to survive installation forces, and fail upon the application of a termination force; and the removable part is removable from the disc space upon failure of the frangible point; the modules are semi-spherical; the complementarily shaped and sized surfaces comprise interfacing surfaces, and wherein the modules comprise a guide passage extending therethrough, angled relative to the interfacing surfaces; the guide passages are angled within a range of 10-40 degrees relative to the interfacing surfaces; a first module of the plurality of modules includes a boss and a second module of the plurality of modules includes a pocket shaped and sized to receive the boss; further including a guide slot; a first module of the plurality of modules includes a guide passage and a second module of the plurality of modules includes a guide passage, the guide passages being sized differently; the second guide passage is formed as a slot; the first and second guide passages extend from an outer surface to the complementary sized and shaped surfaces; the module together form a shape oval in cross-section; a first module of the plurality of modules includes a guide passage forming an opening at a spherical outer surface portion and extending inwardly from the outer surface portion, and a second module of the plurality of modules includes a guide passage forming an opening at the outer surface portion and extending inwardly from the outer surface, the outer surfaces being formed to have bumps protruding from the spherical outer surface portions; a first module of the plurality of modules includes first lobes and a second module of the plurality of modules includes a second lobe, the second lobe being receivable between the first lobes; the plurality of prosthesis modules includes a main body having an outer surface including a bearing surface configured to interface with the upper and lower vertebral endplates; and a wing portion attachable to the main body and configured to limit rotation of the main body relative to the upper and lower vertebrae to a range of motion; the main body includes a receiving indentation configured to receive a portion of the wing portion to attach the main body and the wing portion; the receiving indentation comprises a C-shape configured to receive a portion of the wing portion; the wing comprises a ring-like section configured to fit flush against the main body; the wing portion includes an opening extending therethrough for receiving a guide, and wherein the main body includes an opening formed therein for receiving the guide; comprising an attachment mechanism for attaching the wing to the main body, the attachment mechanism extending through the opening in the wing portion; the opening in the wing portion is square shaped; the wing extends about two sides of the main body.

In another exemplary aspect, the present disclosure is directed to a system for implantation of an intervertebral prosthesis within a disc space, between two vertebra endplates, comprising a plurality of prosthesis modules each having a guide passage extending therethrough along an axis. The modules may be configured to be assembled within the disc space, to form the prosthesis, in a nested relationship in which the guide passages are coaxially aligned with one another. The system also may comprise an elongated guide for inserting the modules into the disc space.

In some aspects, the modules are sequentially insertable into the disc space; the plurality of modules include a first prosthesis module being laterally compressible for insertion into the disc space; the plurality of modules include a first prosthesis module comprising a material having a relatively low modulus of elasticity; and a second prosthesis module comprising a material having a relatively high modulus of elasticity; the plurality of modules include a first prosthesis module having a cavity sized to contain a second prosthesis module such that the surface of the cavity generally uniformly contact the surface of the second prosthesis module upon being nested within the cavity; the first prosthesis module has an orifice extending into the cavity; and the orifice is sized to resist passage of the second prosthesis module outwardly therethrough; the plurality of modules include a third prosthesis module comprising a material having a relatively high modulus of elasticity; the second prosthesis module and the third prosthesis module have a coupling interface; and the guide passage of the first prosthesis module sized to encircle the coupling interface such that the interior surface of the guide passage of the first prosthesis module generally uniformly contacts with the surface of the exterior of the coupling interface; the coupling interface further comprises a receiver body having a receiver neck, with a receiver well disposed therein; an insert body having an insert shaft; and the insert shaft and the receiver well complementarily shaped and sized such that the insert shaft is insertable into the receiver well such that the surface of the insert shaft generally uniformly contacts the surface of the receiver well; the coupling interface further comprises the insert shaft has an insert slope and a latch; the receiver well has a receiver slope that complements the insert slope, and a strike; and the latch and the strike are complementarily designed to engage upon insertion of the insert shaft into the receiver well, and then to bias against each other to prevent removal of the insert shaft from the receiver well; the modules are generally similarly shaped and configurable to form a generally spherical prosthesis; each prosthesis module has a first lobe and a slightly larger second lobe; the guide passage of each module is contained within its second lobe; each prosthesis module having an interface surface; and adjacent interface surfaces having complementary interlocking engagements; further comprising guide passages through the modules; and the guide insertable into the guide passages; the guide is rigid; the guide is flexible; further comprising a guide anchor for securing the guide to the prosthesis; the guide anchor is plastically deformable to bias against the guide; the guide anchor threadedly engages a threaded section of the guide; the interface between the guide and the guide anchor comprises a ratchet and pawl configuration; the guide is secured to a first prosthesis module; the guide is threadedly secured to the guide passage of the first prosthesis module; the guide is integrally formed with the material of the first prosthesis module; the elongated guide has a frangible point and a removable part; the frangible point is constructed to survive installation forces, and fail upon the application of a termination force; and the removable part is removable from the disc space upon failure of the frangible point; the modules are semi-spherical; the complementarily shaped and sized surfaces comprise interfacing surfaces, and wherein the modules comprise a guide passage extending therethrough, angled relative to the interfacing surfaces; the guide passages are angled within a range of 10-40 degrees relative to the interfacing surfaces; a first module of the plurality of modules includes a boss and a second module of the plurality of modules includes a pocket shaped and sized to receive the boss; further including a guide slot; a first module of the plurality of modules includes a guide passage and a second module of the plurality of modules includes a guide passage, the guide passages being sized differently; the second guide passage is formed as a slot; the first and second guide passages extend from an outer surface to the complementary sized and shaped surfaces; the modules together form a shape oval in cross-section; a first module of the plurality of modules includes a guide passage forming an opening at a spherical outer surface portion and extending inwardly from the outer surface portion, and a second module of the plurality of modules includes a guide passage forming an opening at the outer surface portion and extending inwardly from the outer surface, the outer surfaces being formed to have bumps protruding from the spherical outer surface portions; a first module of the plurality of modules includes first lobes and a second module of the plurality of modules includes a second lobe, the second lobe being receivable between the first lobes; the plurality of prosthesis modules includes a main body having an outer surface including a bearing surface configured to interface with the upper and lower vertebral endplates; and a wing portion attachable to the main body and configured to limit rotation of the main body relative to the upper and lower vertebrae to a range of motion; the main body includes a receiving indentation configured to receive a portion of the wing portion to attach the main body and the wing portion; the receiving indentation comprises a C-shape configured to receive a portion of the wing portion; the wing comprises a ring-like section configured to fit flush against the main body; the wing portion includes an opening extending therethrough for receiving a guide, and wherein the main body includes an opening formed therein for receiving the guide; comprising an attachment mechanism for attaching the wing to the main body, the attachment mechanism extending through the opening in the wing portion; the opening in the wing portion is square shaped; the wing extends about two sides of the main body.

In an exemplary aspect, the present disclosure is directed to a method of implanting an intervertebral prosthesis within a disc space, between an upper vertebra endplate and a lower vertebra endplate, comprising inserting a first end of a guide into the disc space; positioning a portion of a prosthesis module about the guide; guiding a first prosthesis module into the disc space along the guide; and guiding a second prosthesis module into the disc space along the guide.

In some aspects, the inserting step is performed by inserting the first end of the guide into the disc space prior to the insertion of a first prosthesis module; inserting the first end of the guide further comprises inserting a first prosthesis module into the disc space with the first end of the guide; guiding at least one prosthesis module further comprises inserting a free end of the guide through a guide passage in the at least one prosthesis module; the method further comprises securing at least a portion of the guide to the prosthesis; removing at least a portion of the guide from the disc space; guiding at least one prosthesis module into the disc space further includes passing the at least one prosthesis module inwardly through an opening into the disc space; and assembling the prosthesis in the disc space such that the assembled prosthesis is of a size substantially preventing the prosthesis from being outwardly expelled from the disc space through the opening; further comprising guiding a first prosthesis module into the disc space that has bearing surfaces slidably engageable with the endplates to maintain a desired disc height; guiding a first prosthesis module that is laterally compressible into the disc space; guiding a first prosthesis module that comprises a material having a relatively low modulus of elasticity into the disc space; and guiding a second prosthesis module that comprises a material having a relatively high modulus of elasticity into the disc space; guiding a first prosthesis module that has a cavity sized to contain a second prosthesis module, such that the surface of the cavity generally uniformly contacts with the exterior surface of the second prosthesis module nested therein; guiding the first prosthesis module into the disc space, wherein the first prosthesis module has an orifice extending into the cavity and the orifice is sized to resist passage of the second prosthesis module outwardly therethrough; guiding a third prosthesis module that comprises a material having a relatively high modulus of elasticity into the disc space, the second prosthesis module and the third prosthesis module having a coupling interface, and a guide passage of the first prosthesis module sized to encircle the coupling interface such that the interior surface of the guide passage of the first prosthesis module generally uniformly contacts with the surface of the exterior of the coupling interface; guiding a third prosthesis module that comprises a material having a relatively high modulus of elasticity into the disc space, the second prosthesis module and the third prosthesis module having a coupling interface, a guide passage of the first prosthesis module sized to encircle the coupling interface such that the interior surface of the guide passage of the first prosthesis module generally uniformly contacts with the surface of the exterior of the coupling interface, the coupling interface further comprises a receiver body having a receiver neck, with a receiver well disposed therein, an insert body having an insert shaft, and the insert shaft and the receiver well complementarily sized such that the insert shaft is insertable into the receiver well such that the surface of the insert shaft generally uniformly contacts the surface of the receiver well; the coupling interface further comprises guiding a third prosthesis module that comprises a material having a relatively high modulus of elasticity into the disc space, the second prosthesis module and the third prosthesis module having a coupling interface, a guide passage of the first prosthesis module sized to encircle the coupling interface such that the interior surface of the guide passage of the first prosthesis module generally uniformly contacts with the surface of the exterior of the coupling interface, the coupling interface further comprises a receiver body having a receiver neck, with a receiver well disposed therein, an insert body having an insert shaft, the insert shaft and the receiver well complementarily sized such that the insert shaft is insertable into the receiver well such that the surface of the insert shaft generally uniformly contacts the surface of the receiver well, the insert shaft having an insert slope and a latch, the receiver well having a receiver slope that complements the insert slope, and a strike, and the latch and strike complementarily designed to engage upon insertion of the insert shaft into the receiver well, and then to bias against each other to prevent removal of the insert shaft from the receiver well; guiding at least one prosthesis module into the disc space further includes passing the at least one prosthesis module inwardly through an opening into the disc space; and assembling the prosthesis in the disc space, the prosthesis comprising a first and a second prosthesis modules of generally similar shape, such that the assembled prosthesis is of a size substantially preventing the prosthesis from being outwardly expelled from the disc space through the opening, and the prosthesis has a generally spherical shape; guiding at least one prosthesis module into the disc space further includes passing the at least one prosthesis module inwardly through an opening into the disc space; and assembling the prosthesis in the disc space, the prosthesis comprising a first and a second prosthesis modules of generally similar shape, such that the assembled prosthesis is of a size substantially preventing the prosthesis from being outwardly expelled from the disc space through the opening, the prosthesis has a generally spherical shape, and each prosthesis module having a first lobe and a slightly larger second lobe; guiding at least one prosthesis module into the disc space further includes passing the at least one prosthesis module inwardly through an opening into the disc space; and assembling the prosthesis in the disc space, the prosthesis comprising a first and a second prosthesis modules of generally similar shape, such that the assembled prosthesis is of a size substantially preventing the prosthesis from being outwardly expelled from the disc space through the opening, the prosthesis has a generally spherical shape, each prosthesis module having a first lobe and a slightly larger second lobe, and each guide passage contained within the respective second lobe; guiding at least one prosthesis module into the disc space further includes passing the at least one prosthesis module inwardly through an opening into the disc space; and assembling the prosthesis in the disc space, the prosthesis comprising a first and a second prosthesis modules of generally similar shape, such that the assembled prosthesis is of a size substantially preventing the prosthesis from being outwardly expelled from the disc space through the opening, the prosthesis has a generally spherical shape, each prosthesis module having an interface surface, and adjacent interface surfaces having complementary interlocking engagements; guiding at least one prosthesis module into the disc space further includes passing the at least one prosthesis module inwardly through an opening into the disc space, the guide being elongated and passable through a guide passage in the at least one prosthesis module; and assembling the prosthesis in the disc space such that the assembled prosthesis is of a size substantially preventing the prosthesis from being outwardly expelled from the disc space through the opening; guiding at least one prosthesis module into the disc space further includes passing the at least one prosthesis module inwardly through an opening into the disc space, the guide being elongated and rigid, and passable through a guide passage in the at least one prosthesis module; and assembling the prosthesis in the disc space such that the assembled prosthesis is of a size substantially preventing the prosthesis from being outwardly expelled from the disc space through the opening; guiding at least one prosthesis module into the disc space further includes passing the at least one prosthesis module inwardly through an opening into the disc space, the guide being elongated and flexible, and passable through a guide passage in the at least one prosthesis module; and assembling the prosthesis in the disc space such that the assembled prosthesis is of a size substantially preventing the prosthesis from being outwardly expelled from the disc space through the opening; securing the assembled prosthesis modules with a guide anchor; securing the assembled prosthesis modules with a guide anchor, wherein the guide anchor is plastically deformable to bias against the guide; securing the assembled prosthesis modules with a guide anchor, wherein the guide anchor threadedly engages a threaded section of the guide; securing the assembled prosthesis modules with a guide anchor, wherein the interface between the guide and the guide anchor comprises a ratchet and pawl configuration; securing the elongated guide to a first prosthesis module; securing the elongated guide threadedly to the guide passage of the first prosthesis module; forming the elongated guide integrally with the material of the first prosthesis module; guiding at least one prosthesis module into the disc space further includes passing the at least one prosthesis module inwardly through an opening into the disc space, wherein the guide is elongated and passable through a guide passage in the at least one prosthesis module, the guide has a frangible point and a removable part, wherein the frangible point is constructed to survive installation forces, and fail upon the application of a termination force, and the removable part is removable from the disc space upon failure of the frangible point; and assembling the prosthesis in the disc space such that the assembled prosthesis is of a size substantially preventing the prosthesis from being outwardly expelled from the disc space through the opening; inserting a first end of the guide includes accessing the disc space from a one of a posterior and posterior lateral approach; the guiding at least one prosthesis includes contacting the upper vertebra endplate and the lower vertebra endplate with the portion of the prosthesis module, the method further including distracting the upper vertebra endplate and the lower vertebra endplate with the portion of the prosthesis module to change a height between the upper and lower vertebra endplates from a first height to a second greater height; contacting the upper and lower vertebra endplates includes contacting with a tapered tip portion of the portion of the prosthesis module; including rotating the portion of the prosthesis module to distract the upper vertebra endplate and the lower vertebra endplate with the portion of the prosthesis module to change a height between the upper and lower vertebra endplates from a first height to a second greater height; the rotating the portion of the prosthesis module includes rotating the portion of the prosthesis module about a longitudinal axis defined by the guide.

In another exemplary aspect, the present disclosure is directed to method of providing separation and relative movement within a disc space between a first vertebra endplate and an adjacent second vertebra endplate, comprising inserting multiple components for assembly into a prosthesis in the disc space; assembling the components into the prosthesis, wherein the prosthesis has a first load-bearing surface, for slideable engagement with the first vertebra endplate, and a second, generally opposed, load-bearing surfaces, for slideable engagement with the second vertebra endplate.

In some aspects, the method further comprises providing a first component having both the first load-bearing surface and the second load-bearing surface; providing a first component having the first load-bearing surface and a second component having the second load-bearing surface; the step of inserting includes guiding the multiple components into the disc space with a guide within a guide passage that is at least partially contained in each of the multiple components.

In yet another exemplary aspect, the present disclosure is directed to a method of implanting an intervertebral prosthesis between upper and lower vertebral endplates, comprising introducing a first module through an opening in an annulus extending around the disc space, the first module having a bearing surface configured to allow sliding of one of the upper and lower endplates along the bearing surface; introducing a second module through the opening in the annulus, the first and second modules having complementary surfaces; engaging the complimentary surface of the first module with the complementary surface of the second module to form an assembled prosthesis of a size substantially preventing it from being outwardly expelled from the disc space through the opening so that the one of the upper and lower endplates slides along the bearing surface.

In some aspects, introducing the first module includes rotating the module with an insertion tool so that a smooth side of the first module faces neural structure within the patient; further including after introducing the first module removing a handle portion from a shaft portion of an insertion tool used to introduce the first module, and wherein introducing the second module includes advancing the second module over the shaft portion; engaging the complementary surfaces includes engaging protruding features on one of the first and second modules with corresponding receiving features on the other of the first and second modules; further including securing the first and second modules together with a fastener; further including manipulating an insertion tool connected to the second module to break off the second module from the insertion tool; including removing a first insertion tool from the first module while maintaining position of the second module with a second insertion tool.

Although only a few exemplary embodiments have been described in detail above, those skilled in the art will readily appreciate that many modifications are possible in the exemplary embodiments without materially departing from the novel teachings and advantages of this disclosure. An example of such a modification would be adapting an egg-like shaped outer body to receive a generally spherical inner body. An additional example would be to alter the orientation of the guide passage such that it does not pass through the center of a prosthesis component.

Accordingly, all such adjustments and alternatives are intended to be included within the scope of the invention, as defined exclusively in the following claims. Those skilled in the art should also realize that such modifications and equivalent constructions or methods do not depart from the spirit and scope of the present disclosure, and that they may make various changes, substitutions, and alternations herein without departing from the spirit and scope of the present disclosure. Furthermore, as used herein, the terms components and modules may be interchanged. It is understood that all spatial references, such as "anterior," "posterior," "inward," "outward," and "sides" are for illustrative purposes only and can be varied within the scope of the disclosure.

We claim:

1. An intervertebral prosthesis apparatus implantable within a disc space, disposed between upper and lower vertebral endplates, via an opening in the annulus extending around the disc space, comprising:
   a first module comprising a generally L-shaped configuration comprising at least three planar surfaces; and
   a second module comprising a generally L-shaped configuration comprising at least three planar surfaces;
   wherein the first and second modules are insertable through the opening into the disc space, the at least three planar surfaces of the first module and the at least three planar surfaces of the second module being complementarily-shaped and sized and configured to engage within the disc space in a manner that the first and second modules form an assembled prosthesis of a size substantially preventing it from being outwardly expelled from the disc space through the opening, the first and second modules having bearing surfaces slidably engageable with the endplates to permit articulation between upper and lower vertebral endplates.

2. The intervertebral prosthesis of claim 1 wherein:
the first and second modules are sequentially insertable.

3. The intervertebral prosthesis of claim 1 wherein the plurality of modules includes:
   a first prosthesis module being laterally compressible for insertion through the opening.

4. The intervertebral prosthesis of claim 1 wherein the plurality of modules includes:
   a first prosthesis module comprising a material having a relatively low modulus of elasticity; and a second prosthesis module comprising a material having a relatively high modulus of elasticity.

5. The intervertebral prosthesis of claim 1 wherein the plurality of modules includes:
   a first prosthesis module having a cavity sized to contain a second prosthesis module such that the surface of the cavity complements the shape and size of the exterior surface of the second prosthesis module.

6. The intervertebral prosthesis of claim 4 wherein the plurality of modules further includes:
   a third prosthesis module comprising a material having a relatively high modulus of elasticity, wherein the second prosthesis module and the third prosthesis module has a coupling interface; and
   wherein the first prosthesis module has a guide passage sized to encircle the coupling interface such that the interior surface of the guide passage of the first prosthesis module generally uniformly contacts with the surface of the exterior of the coupling interface.

7. The intervertebral prosthesis of claim 6, wherein the coupling interface further comprises:
   a receiver body having a receiver neck, with a receiver well disposed therein; and
   an insert body having an insert shaft; the insert shaft and the receiver well being complementarily sized such that the insert shaft is insertable into the receiver well such that the surface of the insert shaft generally uniformly contacts the surface of the receiver well.

8. The intervertebral prosthesis of claim 1 wherein:
the first and second modules are generally similarly shaped and configurable to form a generally spherical prosthesis.

9. The intervertebral prosthesis of claim 8 wherein:
each prosthesis module has a first lobe and a slightly larger second lobe.

10. The intervertebral prosthesis of claim 9 wherein:
the guide passage of each module is contained within its second lobe.

11. The intervertebral prosthesis of claim 1, wherein the plurality of prosthesis modules includes:
   a main body having an outer surface including a bearing surface configured to interface with the upper and lower vertebral endplates; and
   a wing portion attachable to the main body and configured to limit rotation of the main body relative to the upper and lower vertebrae to a range of motion.

12. The intervertebral prosthesis of claim 11, wherein the main body includes a receiving indentation configured to receive a portion of the wing portion to attach the main body and the wing portion, the receiving indentation being a portion of the set of complementarily-shaped and sized surfaces.

13. The intervertebral prosthesis of claim 1, wherein the complementarily shaped and sized surfaces comprise interfacing surfaces, and wherein a first module of the plurality of modules and a second module of the plurality of modules each comprise a guide passage extending therethrough, angled within a range of about 10-40 degrees relative to the interfacing surfaces.

14. The inervertebral prosthesis of claim 1, wherein the first module includes a boss and the second module includes a pocket shaped and sized to receive the boss.

15. The inervertebral prosthesis of claim 1, wherein a first module of the plurality of modules includes a guide passage forming an opening at a first spherical outer surface portion, and a second module of the plurality of modules includes a guide passage forming an opening at the a spherical outer surface portion, at least one of the outer surfaces portions being formed to have a bump protruding therefrom.

16. A system for implantation of an intervertebral prosthesis within a disc space, between a first vertebral endplate and a second vertebral endplate, via an opening in the annulus extending around the disc space, comprising:

a first module comprising a generally L-shaped configuration comprising at least three planar surfaces; and a second module comprising a generally L-shaped configuration comprising at least three planar surfaces; and an elongated guide for inserting the first and second modules into the disc space;

the first and second modules being insertable in a direction through the opening into the disc space; the at least three planar surfaces of the first module and the at least three planar surfaces of the second module being complementarily-shaped and sized; the at least three planar surfaces of the first module being configured to engage the at least three planar surfaces of the second module within the disc space to form an assembled prosthesis of a size substantially preventing it from being outwardly expelled from the disc space through the opening; the first and second modules having bearing surfaces slidably engageable with the endplates.

17. The intervertebral prosthesis of claim 1, wherein the at least three planar surfaces of the first module and the at least three planar surfaces of the second module each comprise a medial shelf, the shelf having a first lobe extending perpendicularly from a first side surface of the shelf and a second lobe extending perpendicularly from a second side surface of the shelf opposite the first side surface.

18. The system of claim 16, wherein the at least three planar surfaces of the first module and the at least three planar surfaces of the second module each comprise a medial shelf, the shelf having a first lobe extending perpendicularly from a first side surface of the shelf and a second lobe extending perpendicularly from a second side surface of the shelf opposite the first side surface.

* * * * *